United States Patent
Colca

(10) Patent No.: US 11,931,345 B2
(45) Date of Patent: Mar. 19, 2024

(54) THIAZOLIDINEDIONE ANALOGS FOR THE TREATMENT OF NAFLD AND METABOLIC DISEASES

(71) Applicant: Cirius Therapeutics, Inc., San Diego, CA (US)

(72) Inventor: Gerard R. Colca, San Diego, CA (US)

(73) Assignee: Cirius Therapeutics, Inc., San Diego, CA (US)

( * ) Notice: Subject to any disclaimer, the term of this patent is extended or adjusted under 35 U.S.C. 154(b) by 712 days.

(21) Appl. No.: 17/052,791

(22) PCT Filed: May 3, 2019

(86) PCT No.: PCT/US2019/030723
§ 371 (c)(1),
(2) Date: Nov. 3, 2020

(87) PCT Pub. No.: WO2019/213611
PCT Pub. Date: Nov. 7, 2019

(65) Prior Publication Data
US 2021/0361629 A1 Nov. 25, 2021

Related U.S. Application Data

(60) Provisional application No. 62/667,259, filed on May 4, 2018.

(51) Int. Cl.
*A61K 31/426* (2006.01)
*A61K 38/26* (2006.01)
*A61P 1/16* (2006.01)

(52) U.S. Cl.
CPC ............ *A61K 31/426* (2013.01); *A61K 38/26* (2013.01); *A61P 1/16* (2018.01)

(58) Field of Classification Search
CPC .................................................. A61K 31/426
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 2006/0178375 A1 | 8/2006 | Ohtake et al. |
| 2008/0227846 A1 | 9/2008 | Singh et al. |
| 2009/0312246 A1* | 12/2009 | Baron .................... A61K 38/26 514/1.1 |
| 2012/0026424 A1 | 2/2012 | Youk et al. |
| 2013/0281414 A1 | 10/2013 | Colca et al. |
| 2015/0258054 A1 | 9/2015 | Mizuguchi et al. |
| 2016/0051529 A1 | 2/2016 | Colca et al. |
| 2017/0049762 A1 | 2/2017 | Dewitt |
| 2018/0133204 A1 | 5/2018 | DeWitt |
| 2019/0099147 A1 | 4/2019 | Ghosh et al. |
| 2021/0361629 A1 | 11/2021 | Colca |
| 2022/0031667 A1 | 2/2022 | Colca et al. |

FOREIGN PATENT DOCUMENTS

| | | |
|---|---|---|
| WO | 2010015818 A1 | 2/2010 |
| WO | 2011133611 A1 | 10/2011 |
| WO | WO-2011133611 A1 | 10/2011 |
| WO | WO-2019213611 A1 | 11/2019 |
| WO | WO-2020146810 A1 | 7/2020 |
| WO | 2021092496 A1 | 5/2021 |
| WO | 2021212054 A1 | 10/2021 |

OTHER PUBLICATIONS

Xu et al., SIRT1 Mediates the Effect of GLP-1 Receptor Agonist Exenatide on Ameliorating Hepatic Steatosis, Diabetes, vol. 63, pp. 3637-3646 (2014).*
Al-Muhammed et al. In-vivo studies on dexamethasone sodium phosphate liposomes. J Microencapsul. 13(3):293-306 (1996).
Berge et al. Pharmaceutical Salts. Journal of Pharmaceutical Sciences 66(1):1-19 (Jan. 1977).
Chonn et al. Recent advances in liposomal drug-delivery systems. Curr Opin Biotechnol. 6(6):698-708(1995).
Colca et al. Treating fatty liver disease by modulating mitochondrial pyruvate metabolism. HepatorI Commun 1(3):193-197 (2017).
Colca et al., Identification of a mitochondrial target of thiazolidinedione insulin sensitizers (mTOT)—relationship to newly identified mitochondrial pyruvate carrier proteins. PLoS One 8(5):e61551. doi: 10.1371/journal.pone.0061551 (2013).
Eyles et al. Oral delivery and fate of poly(lactic acid) microsphere-encapsulated interferon in rats. J Pharm Pharmacol. 49(7):669-74 (1997).
Gao et al. Controlled release of a contraceptive steroid from biodegradable and injectable gel formulations: in vitro evaluation. Pharm Res. 12(6):857-63 (1995).
Mcgill et al. The past and present of serum aminotransferases and the future of liver injury biomarkers. EXCLI j 15:817-828 (2016).
Munson et al. Ligand: a versatile computerized approach for characterization of ligand-binding systems. Anal Biochem. 107(1):220-239 (1980).
Ostro et al. Use of Liposomes as Injectable-Drug Delivery Systems. Am J Hosp Pharm 46(8):1576-1587 (Aug. 1989).
PCT/US2019/030723 International Search Report and Written Opinion dated Sep. 13, 2019.
PCT/US2019/030723 Invitation to Pay Additional Fees dated Jun. 26, 2019.
Rao. Recent developments of collagen-based materials for medical applications and drug delivery systems. J Biomater Sci Polym Ed. 7(7):623-45 (1995).
Sherwani et al. Significance of HbA1c Test in Diagnosis and Prognosis of Diabetic Patients. Biomark Insights 11:95-104 (2016).
PCT/US2020/013203 International Search Report and Written Opinion dated Apr. 22, 2020.
PCT/US2020/013203 Invitation to Pay Additional Fees dated Feb. 24, 2020.

(Continued)

*Primary Examiner* — Deepak R Rao
(74) *Attorney, Agent, or Firm* — Honigman LLP

(57) ABSTRACT

Provided herein are thiazolidinedione analogues that are useful for treating non-alcoholic fatty liver disease (NAFLD), non-alcoholic steatohepatitis (NASH), diabetes, and other metabolic inflammation-mediated disease and disorders.

26 Claims, 13 Drawing Sheets

(56) References Cited

OTHER PUBLICATIONS

Pubchem CID 25230266 https://pubchem.ncbi.nlm.nih.gov/compound/25230266 (2009).
Aghamohammadzadeh et al., The effect of pioglitazone on weight, lipid profile and liver enzymes in type 2 diabetic patients. Ther Adv Endocrinol Metab. 6(2):56-60 (2015).
CDC COVID-19 Response Team. Preliminary Estimates of the Prevalence of Selected Underlying Health Conditions Among Patients with Coronavirus Disease 2019—United States, Feb. 12-Mar. 28, 2020. MMWR Morb Mortal Wkly Rep. 69(13):382-386 (Apr. 3, 2020).
Colca et al. NASH (nonalcoholic steatohepatitis), diabetes, and macrovascular disease: multiple chronic conditions and a potential treatment at the metabolic root. Expert Opin Investig Drugs. 29(2):191-196 (2020).
Drucker. Diabetes, obesity, metabolism, and SARS-CoV-2 infection: the end of the beginning. Cell Metabolism 33(3):479-498 (2021).
Fadini et al. Prevalence and impact of diabetes among people infected with SARS-CoV-2. J Endocrinol Invest. 43(6):867-869 (2020).
Gordon et al. A SARS-CoV-2-Human Protein-Protein Interaction Map Reveals Drug Targets and Potential Drug-Repurposing. Nature 583:459-468 (2020).
Guo et al. Diabetes is a risk factor for the progression and prognosis of COVID-19. Diabetes Metab Res Rev. 36(7):e3319 (2020).
Hoffmann et al. SARS-CoV-2 Cell Entry Depends on ACE2 and TMPRSS2 and Is Blocked by a Clinically Proven Protease Inhibitor. Cell 181:271-280 (2020).
Luzi et al. Influenza and obesity: its odd relationship and the lessons for COVID-19 pandemic. Acta Diabetol. pp. 1-6 (2020).
Moseley et al. Peroxisome proliferator-activated receptor and AMP-activated protein kinase agonists protect against lethal influenza virus challenge in mice. Influenza Other Respir Viruses. 4(5):307-11 (2010).
PCT/US2021/27803 International Search Report and Written Opinion dated Aug. 13, 2021.
Phend. COVID-19: Abnormal Clotting Common in More Severe Disease—Chinese clinicians on the early front lines argue for anticoagulation. Infectious Disease Mar. 24, 2020.
Aithal et al., Randomized, placebo-controlled trial of pioglitazone in nondiabetic subjects with nonalcoholic steatohepatitis. Gastroenterology 135:1176-1184 (2008).
Armstrong et al., Liraglutide safety and efficacy in patients with non-alcoholic steatohepatitis (LEAN): a multicentre, double-blind, randomised, placebo-controlled phase 2 study. Lancet 387:679-690 (2016).
Bedossa et al., Histopathological algorithm and scoring system for evaluation of liver lesions in morbidly obese patients. Hepatology 56:1751-1759 (2012).
Belfort et al., A placebo-controlled trial of pioglitazone in subjects with nonalcoholic steatohepatitis. New England Journal of Medicine 355:2297-2307 (2006).
Brunt et al., Nonalcoholic steatohepatitis: a proposal for grading and staging the histological lesions. Am J Gastroenterol 94:2467-2474 (1999).
Campos et al., A clinical scoring system for predicting nonalcoholic steatohepatitis in morbidly obese patients. Hepatology 47:1916-1923 (2008).
Chalasani et al., The diagnosis and management of nonalcoholic fatty liver disease: Practice guidance from the American Association for the Study of Liver Diseases. Hepatology 67:328-357 (2018).
Cusi et al., Long-term pioglitazone treatment for patients with nonalcoholic steatohepatitis and prediabetes or type 2 diabetes mellitus: a randomized trial. Ann Intern Med 165:305-315 (2016).
Davison et al., Lack of reliability of liver biopsies in nonalcoholic steatohepatitis (NASH) clinical trials—potential implications for developing new therapies for NASH. In: The International Liver Congress. London, UK (2020).
European Medicines Agency, Reflection paper on regulatory requirements for the development of medicinal products for chronic non-infectious liver diseases (PBC, PSC, NASH). https://www.ema.europa.eu/en/documents/scientific-guideline/reflection-paper-regulatory-requirements-development-medicinal-products-chronic-non-infectious-liver_en.pdf (2018).
FDA Draft Guidance: Noncirrhotic Nonalcoholic Steatohepatitis With Liver Fibrosis: Developing Drugs for Treatment Guidance for Industry. In: U.S. Department of Health and Human Services Food and Drug Administration Center for Drug Evaluation and Research (CDER). https://www.fda.gov/media/119044/download (2018).
Fracanzani et al., Risk of severe liver disease in nonalcoholic fatty liver disease with normal aminotransferase levels: a role for insulin resistance and diabetes. Hepatology 48:792-798 (2008).
Friedman et al., A randomized, placebo-controlled trial of cenicriviroc for treatment of nonalcoholic steatohepatitis with fibrosis. Hepatology 67:1754-1767 (2018).
Georgescu et al., Angiotensin-receptor blockers as therapy for mild-to-moderate hypertension-associated non-alcoholic steatohepatitis. World J Gastroenterol 15:942-954 (2009).
Gomez-Dominguez et al., Transient elastography: a valid alternative to biopsy in patients with chronic liver disease. Aliment Pharmacol Ther 24:513-518 (2006).
Hadizadeh et al., Nonalcoholic fatty liver disease: Diagnostic biomarkers. World J Gastrointest Pathophysiol 8:11-26 (2017).
Harrison et al., A randomized, placebo-controlled trial of emricasan in patients with NASH and F1-F3 fibrosis. J Hepatol 72(5):816-827 (2020).
Harrison et al., Insulin sensitizer MSDC-0602K in nonalcoholic steatohepatitis: a randomized, double-blind, placebo-controlled phase 2b study. J Hepatol 72(4):613-626 (2020).
Harrison et al., Prospective liver biopsy-based prevalence of non-alcoholic fatty liver disease and steatohepatitis among a large middle-aged population utilizing FibroScan, LiverMultiscan and magnetic resonance elastography to guide liver biopsy. J Hepatol 70:E770-E771 (2019).
Harrison et al., Resmetirom (MGL-3196) for the treatment of non-alcoholic steatohepatitis: a multicentre, randomised, double-blind, placebo-controlled, phase 2 trial. Lancet 394:2012-2024 (2019).
Hernaez et al., Diagnostic accuracy and reliability of ultrasonography for the detection of fatty liver: a meta-analysis. Hepatology 54:1082-1090 (2011).
Idilman et al., A comparison of liver fat content as determined by magnetic resonance imaging-proton density fat fraction and MRS versus liver histology in non-alcoholic fatty liver disease. Acta Radiol 57:271-278 (2016).
Kleiner et al., Association of histologic disease activity with progression of nonalcoholic fatty liver disease. JAMA Network Open 2:e1912565 (2019).
Kleiner et al., Design and validation of a histological scoring system for nonalcoholic fatty liver disease. Hepatology 41:1313-1321 (2005).
Leuschner et al., High-dose ursodeoxycholic acid therapy for non-alcoholic steatohepatitis: a double-blind, randomized, placebo-controlled trial. Hepatology 52:472-479 (2010).
Lichtinghagen et al., The enhanced liver fibrosis (ELF) score: normal values, influence factors and proposed cut-off values. J Hepatol 59:236-242 (2013).
Loomba et al., The global NAFLD epidemic. Nat Rev Gastroenterol Hepatol 10:686-690 (2013).
Machado et al., Non-invasive diagnosis of non-alcoholic fatty liver disease. A critical appraisal. J Hepatol 58:1007-1019 (2013).
Maximos et al., The role of liver fat and insulin resistance as determinants of plasma aminotransferase elevation in nonalcoholic fatty liver disease. Hepatology 61:153-160 (2015).
Mccommis et al., Targeting the mitochondria! pyruvate carrier attenuates fibrosis in a mouse model of nonalcoholic steatohepatitis. Hepatology 65(5):1543-1556 (2017).
Mofrad et al., Clinical and histologic spectrum of nonalcoholic fatty liver disease associated with normal ALT values. Hepatology 37:1286-1292 (2003).

(56) References Cited

OTHER PUBLICATIONS

Munson et al. Ligand: a versatile computerized approach for characterization of ligand-binding systems. Analyt. Biochem. 107:220-239 (1980).

Neuschwander-Tetri et al., Farnesoid X nuclear receptor ligand obeticholic acid for non-cirrhotic, non-alcoholic steatohepatitis (FLINT): a multicentre, randomised, placebo-controlled trial. Lancet 385:956-965 (2015).

Nogueira et al., Omega-3 polyunsaturated fatty acids in treating non-alcoholic steatohepatitis: A randomized, double-blind, placebo-controlled trial. Clin Nutr 35:578-586 (2016).

Nonalcoholic Steatohepatitis Clinical Research Network (NASH). NIDDK Central Repository. https://repository.niddk.nih.gov/studies/nash/ (2019).

PCT/US2020/059548 International Search Report and Written Opinion dated Feb. 26, 2021.

Ratziu et al., Diagnostic value of biochemical markers (FibroTest-FibroSURE) for the prediction of liver fibrosis in patients with non-alcoholic fatty liver disease. BMC Gastroenterol 6:6 (2006).

Ratziu et al., Elafibranor, an agonist of the peroxisome proliferator-activated receptor-alpha and -delta, induces resolution of nonalcoholic steatohepatitis without fibrosis worsening. Gastroenterology 150:1147-1159 e1145 (2016).

Ratziu et al., One-year results of the global phase 2b randomized placebocontrolled ARREST trial of aramchol, a stearoyl CoA desaturase modulator in NASH patients. In: The Liver Meeting. San Francisco, CA, USA http://www.natap.org/2018/AASLD/AASLD_222.htm (2018).

Ratziu et al., Rosiglitazone for nonalcoholic steatohepatitis: one-year results of the randomized placebo-controlled fatty liver improvement with rosiglitazone therapy (FLIRT) Trial. Gastroenterology 135:100-110 (2008).

Ratziu et al., Sampling variability of liver biopsy in nonalcoholic fatty liver disease. Gastroenterology 128:1898-1906 (2005).

Rinella et al., The globalization of nonalcoholic fatty liver disease: Prevalence and impact on world health. Hepatology 64:19-22 (2016).

Sanyal et al., Pioglitazone, vitamin E, or placebo for nonalcoholic steatohepatitis. New England Journal of Medicine 362:1675-1685 (2010).

Seeff et al., Complication rate of percutaneous liver biopsies among persons with advanced chronic liver disease in the HALT-C trial. Clin Gastroenterol Hepatol 8:877-883 (2010).

Sheka et al., Nonalcoholic steatohepatitis: a review. JAMA 323:1175-1183 (2020).

Sorbi et al., The ratio of aspartate aminotransferase to alanine aminotransferase: potential value in differentiating nonalcoholic steatohepatitis from alcoholic liver disease. Am J Gastroenterol 94:1018-1022 (1999).

Vallet-Pichard et al., FIB-4: an inexpensive and accurate marker of fibrosis in HCV infection. comparison with liver biopsy and fibrotest. Hepatology 46:32-36 (2007).

Verma et al., Predictive value of ALT levels for non-alcoholic steatohepatitis (NASH) and advanced fibrosis in non-alcoholic fatty liver disease (NAFLD). Liver Int 33:1398-1405 (2013).

Viechtbauer W., Conducting meta-analyses in r with the metafor package. Journal of Statistical Software 36(3):1-48 (2010).

Youden, W.J. (1950). "Index for rating diagnostic tests". Cancer. 3: 32-35. doi:10.1002/1097-0142(1950)3:1&32::aid-cncr28200301063.0.co;2-3.

Younossi et al., Burden of illness and economic model for patients with nonalcoholic steatohepatitis in the United States. Hepatology 69:564-572 (2019).

Younossi et al., Global burden of NAFLD and NASH: trends, predictions, risk factors and prevention. Nat Rev Gastroenterol Hepatol 15:11-20 (2018).

Younossi et al., Nonalcoholic steatohepatitis is the fastest growing cause of hepatocellular carcinoma in liver transplant candidates. Clin Gastroenterol Hepatol 17:748-755 e743 (2019).

Younossi et al., Obeticholic acid for the treatment of non-alcoholic steatohepatitis: interim analysis from a multicentre, randomised, placebo-controlled phase 3 trial. Lancet 394:2184-2196 (2019).

\* cited by examiner

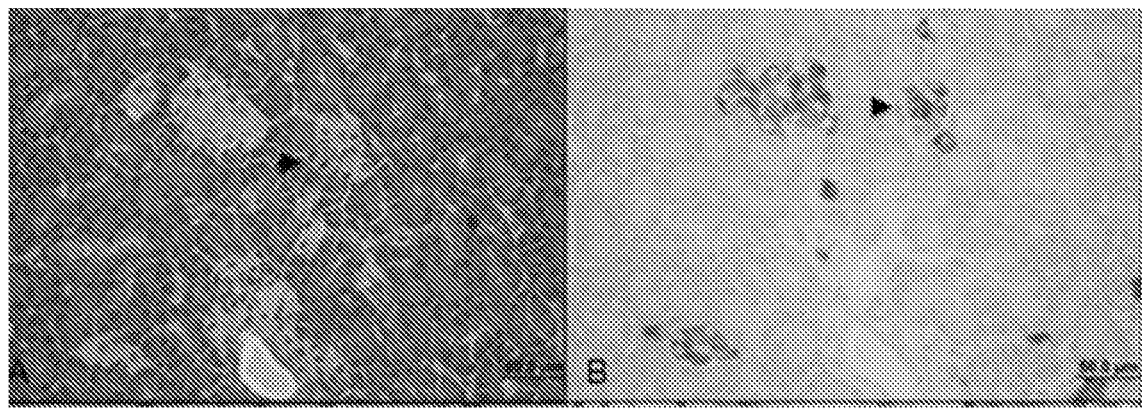
FIG. 7A     FIG. 7B
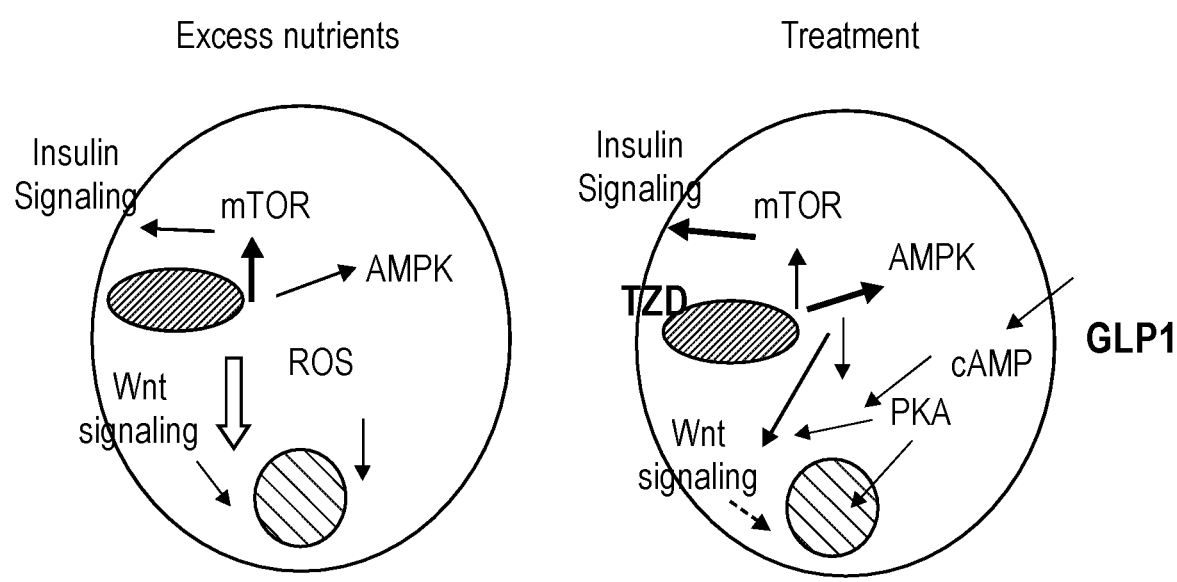
FIG. 8A     FIG. 8B

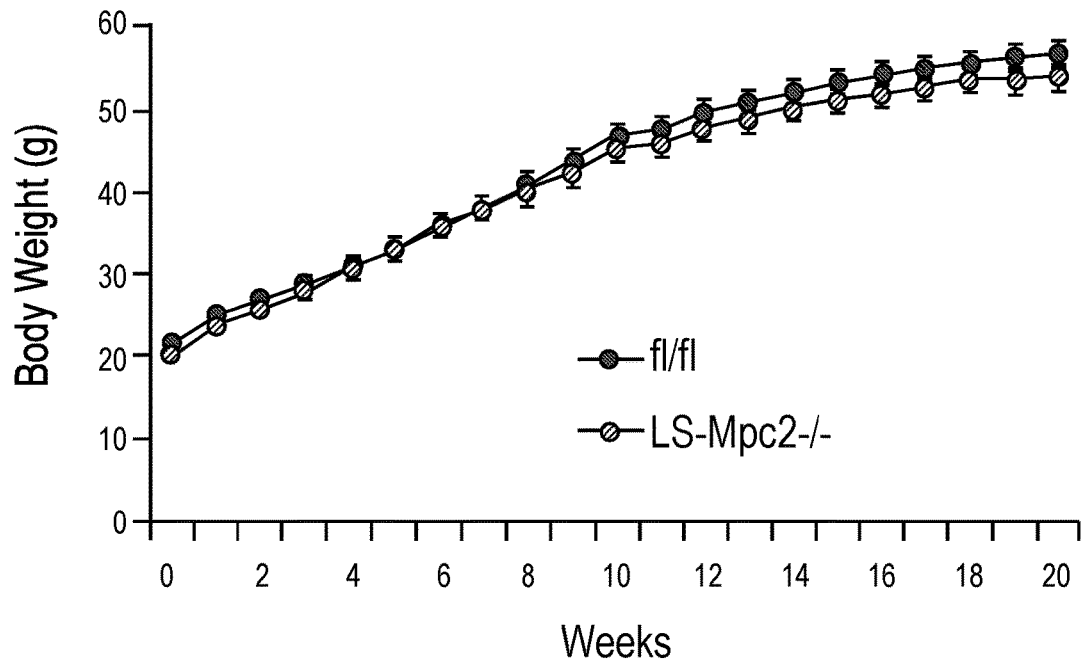
FIG. 9A
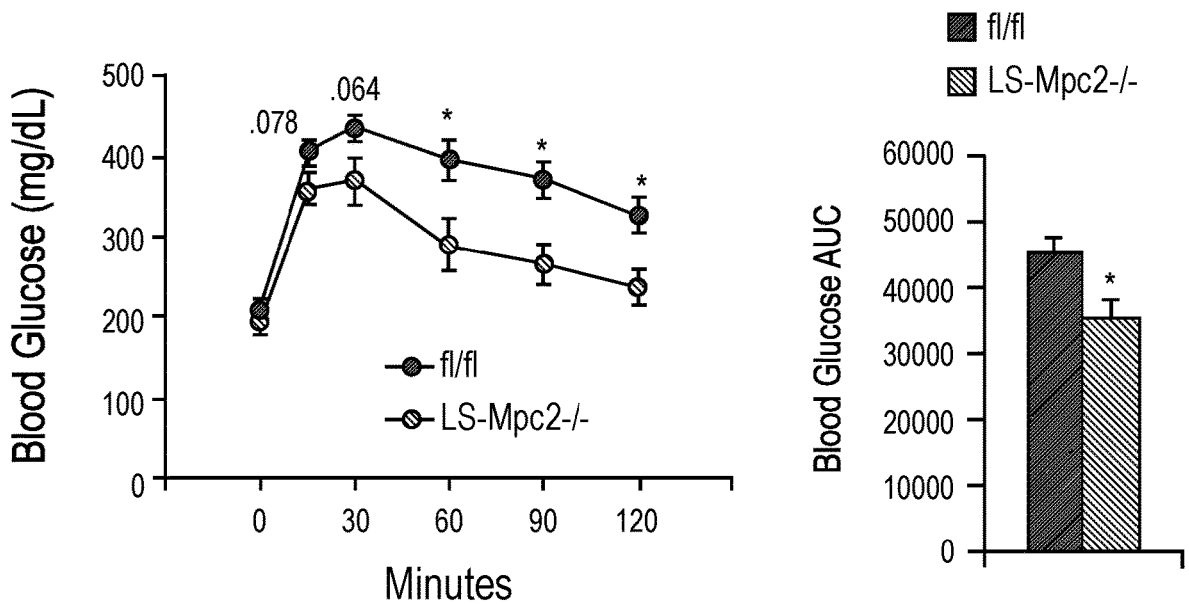
FIG. 9B  FIG. 9C

THIAZOLIDINEDIONE ANALOGS FOR THE TREATMENT OF NAFLD AND METABOLIC DISEASES

CROSS REFERENCE TO RELATED APPLICATIONS

This application is the National Stage entry of International Application No. PCT/US2019/030723, filed on May 3, 2019, which claims the benefit of U.S. Provisional Application No. 62/667,259, filed May 4, 2018, Entitled: THIAZOLIDINEDIONE ANALOGS FOR THE TREATMENT OF NAFLD AND METABOLIC DISEASES, which is incorporated by reference in the disclosure of this application.

BACKGROUND

Peroxisome Proliferator Activated Receptors (PPARs), which are members of the nuclear hormone receptor super family, are ligand-activated transcription factors regulating gene expression. PPARs have been implicated in autoimmune diseases and other diseases (e.g., diabetes mellitus, cardiovascular disease, gastrointestinal disease, and Alzheimer's disease). First generation thiazolidinediones approved for treatment of type 2 diabetes are direct activators of the PPAR gamma subtype. Newer agents work by modifying the activity of the mitochondrial pyruvate carrier.

The mitochondrial pyruvate carrier (MPC) comprises two proteins, MPC1 and MPC2, that form a carrier complex in the inner mitochondrial membrane. Transport into the mitochondrial matrix is required for pyruvate metabolism and critical for a number of metabolic pathways. Modulation of MPC indirectly affects PPAR-directed and other transcriptional networks.

The identification of compounds that modulate MPC and improve mitochondrial function, including modulating PPAR function, is an ongoing challenge. Disclosed herein, inter alia, are solutions to these and other problems in the art which include combinations of specific agents in order to achieve optimal therapeutic efficacy.

BRIEF SUMMARY OF THE INVENTION

In an aspect provided herein is a method of treating non-alcoholic fatty liver disease (NAFLD) and/or metabolic syndrome, comprising administering to a subject in need thereof:
(i) a therapeutically effective amount of a compound of structural Formula (I):

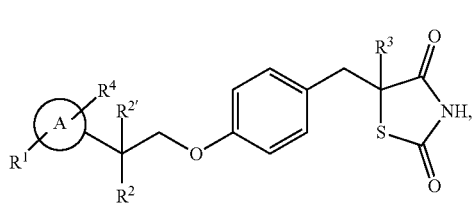

or a pharmaceutically acceptable salt thereof, wherein:
$R^1$ is hydrogen, halogen, substituted or unsubstituted alkyl, or —$OR^{1A}$;
$R^2$ is halogen, hydroxyl, or optionally substituted aliphatic;
$R^{2'}$ is hydrogen, or $R^2$ and $R^{2'}$ may optionally be joined to form oxo;
$R^3$ is hydrogen or deuterium;
$R^4$ is hydrogen, halogen, substituted or unsubstituted alkyl, or —$OR^{4A}$;
A is phenyl; and
$R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
(ii) at least one additional therapeutic agent selected from a GLP1 agonist, a phosphodiesterase (PDE) inhibitor, and a thyroid hormone beta receptor agonist.

In another aspect provided herein is a method of treating non-alcoholic fatty liver disease (NAFLD) and/or at least one metabolic inflammation-mediated disease or disorder, comprising administering to a subject in need thereof:
(i) a therapeutically effective amount of a compound of structural Formula (I):

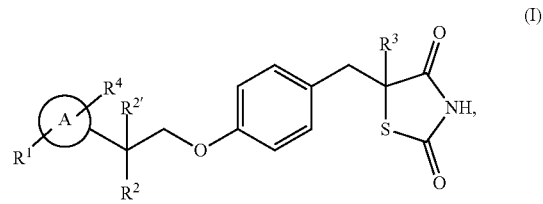

or a pharmaceutically acceptable salt thereof, wherein:
$R^1$ is hydrogen, halogen, substituted or unsubstituted alkyl, or —$OR^{1A}$;
$R^2$ is halogen, hydroxyl, or optionally substituted aliphatic;
$R^{2'}$ is hydrogen, or $R^2$ and $R^{2'}$ may optionally be joined to form oxo;
$R^3$ is hydrogen or deuterium;
$R^4$ is hydrogen, halogen, substituted or unsubstituted alkyl, or —$OR^{4A}$;
A is phenyl; and
$R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
(ii) at least one additional therapeutic agent selected from a phosphodiesterase (PDE) inhibitor, a thyroid hormone beta receptor agonist, or a GLP1 agonist. In some embodiments, the GLP1 agonist is liraglutide, semaglutide, or dulaglutide.

In an aspect provided herein is a method of treating non-alcoholic fatty liver disease (NAFLD) and/or metabolic syndrome, comprising administering to a subject in need thereof:
(i) a therapeutically effective amount of a pharmaceutical composition, comprising a compound of structural Formula (I):

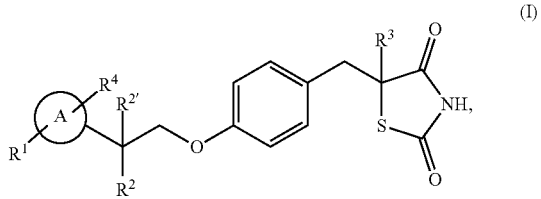

or a pharmaceutically acceptable salt thereof, and a pharmaceutically acceptable excipient, wherein:
- $R^1$ is hydrogen, halogen, substituted or unsubstituted alkyl, or —$OR^{1A}$;
- $R^2$ is halogen, hydroxyl, or optionally substituted aliphatic;
- $R^{2'}$ is hydrogen, or $R^2$ and $R^{2'}$ may optionally be joined to form oxo;
- $R^3$ is hydrogen or deuterium;
- $R^4$ is hydrogen, halogen, substituted or unsubstituted alkyl, or —$OR^{4A}$;
- A is phenyl; and
- $R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
- (ii) at least one additional therapeutic agent selected from a GLP1 agonist, a phosphodiesterase (PDE) inhibitor, or a thyroid hormone beta receptor agonist.

In an aspect provided herein is a method of treating non-alcoholic fatty liver disease (NAFLD) and/or at least one metabolic inflammation-mediated disease or disorder, comprising administering to a subject in need thereof a therapeutically effective amount of a pharmaceutical composition comprising:
- (i) a compound of structural Formula (I), or a pharmaceutically acceptable salt thereof:

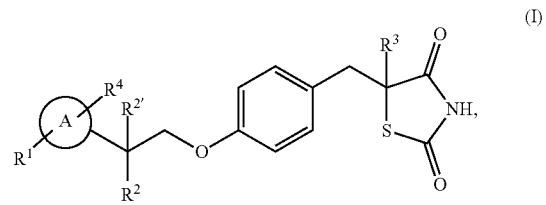

wherein:
- $R^1$ is hydrogen, halogen, substituted or unsubstituted alkyl, or —$OR^{1A}$;
- $R^2$ is halogen, hydroxyl, or optionally substituted aliphatic;
- $R^{2'}$ is hydrogen, or $R^2$ and $R^{2'}$ may optionally be joined to form oxo;
- $R^3$ is hydrogen or deuterium;
- $R^4$ is hydrogen, halogen, substituted or unsubstituted alkyl, or —$OR^{4A}$;
- A is phenyl; and
- $R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- (ii) at least one additional therapeutic agent selected from a GLP1 agonist, a phosphodiesterase (PDE) inhibitor, or a thyroid hormone beta receptor agonist; and
- (iii) and a pharmaceutically acceptable excipient, wherein the compound of Formula (I) and the at least one additional therapeutic agent selected from a GLP1 agonist, a phosphodiesterase (PDE) inhibitor, or a thyroid hormone beta receptor agonist are co-formulated.

In an aspect is provided a pharmaceutical composition, comprising a compound of structural formula:

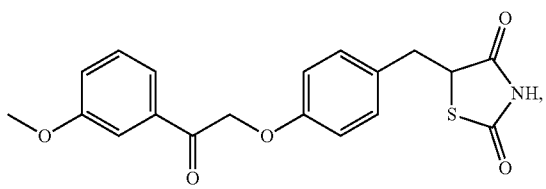 [SMILES: COc1cccc(C(=O)COc2ccc(CC3SC(=O)NC3=O)cc2)c1]

or a pharmaceutically acceptable salt thereof, a GLP1 agonist and a pharmaceutically acceptable excipient. In some embodiments, the GLP1 agonist is exenatide, liraglutide, semaglutide, or dulaglutide.

In an aspect is provided a method of treating non-alcoholic fatty liver disease (NAFLD) and/or metabolic syndrome, comprising administering to a subject in need thereof a therapeutically effective amount of a pharmaceutical composition, comprising a compound of structural formula:

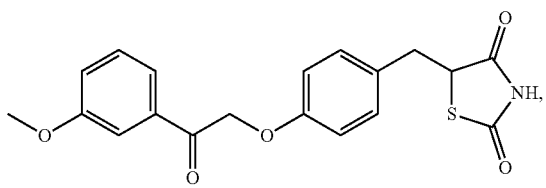 [SMILES: COc1cccc(C(=O)COc2ccc(CC3SC(=O)NC3=O)cc2)c1]

or a pharmaceutically acceptable salt thereof, a GLP1 agonist and a pharmaceutically acceptable excipient. In some embodiments, the GLP1 agonist is exenatide, liraglutide, semaglutide, or dulaglutide.

In an aspect is provided a method of treating at least one metabolic inflammation-mediated disease or disorder, comprising administering to a subject in need thereof a therapeutically effective amount of a compound of structural Formula (I):

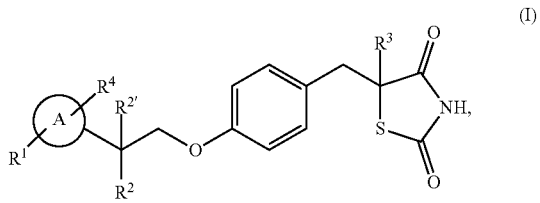

or a pharmaceutically acceptable salt thereof, wherein:
- $R^1$ is hydrogen, halogen, substituted or unsubstituted alkyl, or —$OR^{1A}$;

R² is halogen, hydroxyl, or optionally substituted aliphatic;
R²' is hydrogen, or R² and R²' may optionally be joined to form oxo;
R³ is deuterium;
R⁴ is hydrogen, halogen, substituted or unsubstituted alkyl, or —OR⁴·⁴;
A is phenyl; and
R¹·⁴ and R⁴·⁴ are independently hydrogen, halogen, —CF₃, —CCl₃, —CBr₃, —CI₃, —CHF₂, —CHCl₂, —CHBr₂, —CHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In an aspect is provided a method of inhibiting hepatic mitochondrial pyruvate carrier (MPC) in a cell, comprising contacting the MPC with a compound of structural Formula (I):

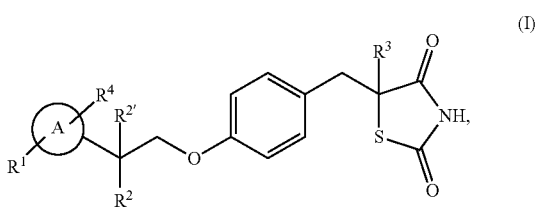

(I)

or a pharmaceutically acceptable salt thereof, wherein:
R¹ is hydrogen, halogen, substituted or unsubstituted alkyl, or —OR¹·⁴;
R² is halogen, hydroxyl, or optionally substituted aliphatic;
R²' is hydrogen, or R² and R²' may optionally be joined to form oxo;
R³ is hydrogen or deuterium;
R⁴ is hydrogen, halogen, substituted or unsubstituted alkyl, or —OR⁴·⁴;
A is phenyl; and
R¹·⁴ and R⁴·⁴ are independently hydrogen, halogen, —CF₃, —CCl₃, —CBr₃, —CI₃, —CHF₂, —CHCl₂, —CHBr₂, —CHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, the cell is a hepatocyte.

In an aspect is provided a method of improving or increasing glucose tolerance and/or insulin sensitivity, comprising administering to a subject in need thereof a therapeutically effective amount of a compound of structural Formula (I):

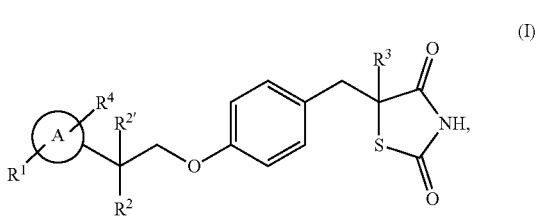

(I)

or a pharmaceutically acceptable salt thereof, wherein:
R¹ is hydrogen, halogen, substituted or unsubstituted alkyl, or —OR¹·⁴;
R² is halogen, hydroxyl, or optionally substituted aliphatic;
R²' is hydrogen, or R² and R²' may optionally be joined to form oxo;
R³ is hydrogen or deuterium;
R⁴ is hydrogen, halogen, substituted or unsubstituted alkyl, or —OR⁴·⁴;
A is phenyl; and
R¹·⁴ and R⁴·⁴ are independently hydrogen, halogen, —CF₃, —CCl₃, —CBr₃, —CI₃, —CHF₂, —CHCl₂, —CHBr₂, —CHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In an aspect provided herein is a method of treating or preventing a hepatic disease, disorder, or injury, comprising administering to a subject in need thereof a therapeutically effective amount of a compound of structural Formula (I):

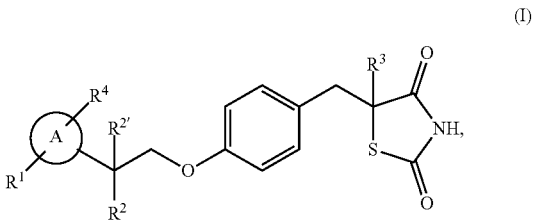

(I)

or a pharmaceutically acceptable salt thereof, wherein:
R¹ is hydrogen, halogen, substituted or unsubstituted alkyl, or —OR¹·⁴;
R² is halogen, hydroxyl, or optionally substituted aliphatic;
R²' is hydrogen, or R² and R²' may optionally be joined to form oxo;
R³ is hydrogen or deuterium;
R⁴ is hydrogen, halogen, substituted or unsubstituted alkyl, or —OR⁴·⁴;
A is phenyl; and
R¹·⁴ and R⁴·⁴ are independently hydrogen, halogen, —CF₃, —CCl₃, —CBr₃, —CI₃, —CHF₂, —CHCl₂, —CHBr₂, —CHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect provided herein is a method of treating or preventing hepatocyte fibrogenesis, comprising administering to a subject in need thereof a therapeutically effective amount of a compound of structural Formula (I):

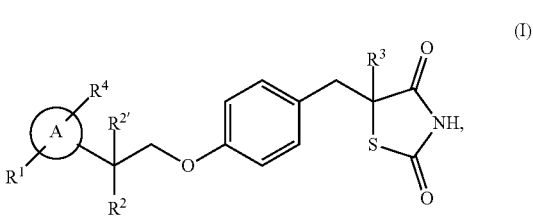

(I)

or a pharmaceutically acceptable salt thereof, wherein:
$R^1$ is hydrogen, halogen, substituted or unsubstituted alkyl, or —$OR^{1A}$;
$R^2$ is halogen, hydroxyl, or optionally substituted aliphatic;
$R^{2'}$ is hydrogen, or $R^2$ and $R^{2'}$ may optionally be joined to form oxo;
$R^3$ is hydrogen or deuterium;
$R^4$ is hydrogen, halogen, substituted or unsubstituted alkyl, or —$OR^{4A}$;
A is phenyl; and
$R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 7A-7B. Show islet neogenesis (FIG. 7A) and cells positive for insulin (FIG. 7B).

FIGS. 8A-8B. Are schematic representations of the effects of excess nutrients (FIG. 8A) and treatment with MSDC-0602+GLP1 (FIG. 8B) on insulin signaling.

FIGS. 9A-9C. Show the comparative results from diet-induced obese (60% HF diet) LS-MPC2−/− and WT (fl/fl) mice: Body weight (FIG. 9A); Blood glucose levels (FIG. 9B); Blood glucose AUC (FIG. 9C).

DETAILED DESCRIPTION

Figure 1A:
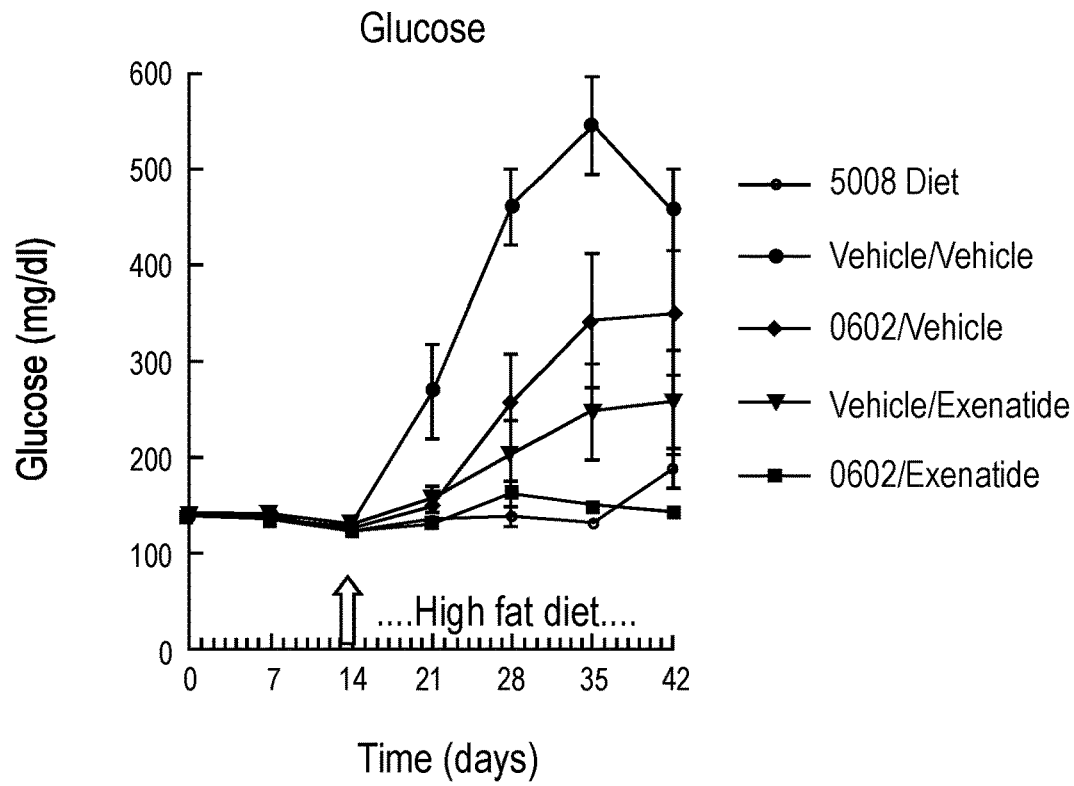
FIGS. 1A-1B. Graphic representations of the effects of MSDC-0602 and GLP1 on circulating glucose (FIG. 1A) and insulin (FIG. 1B).

Provided herein are, for example, compounds and compositions that modulate the MPC and have reduced binding and activation of the nuclear transcription factor PPARγ. Also provided herein are, for example, methods of treating or preventing a metabolic inflammation-mediated disease or disorder (e.g., diabetes mellitus type 2), metabolic syndrome, non-alcoholic fatty liver disease (NAFLD), and/or non-alcoholic steatohepatitis (NASH).

I. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and includes mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic) carbonyl, (cycloaliphatic)carbonyl, or (heterocycloaliphatic)

carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl. An alkoxy is an alkyl attached to the remainder of the molecule via an oxygen linker (—O—).

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroarylcarbonylamino, heteroarylaminocarbonyl, heteroaralkylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

As used herein, an "amido" encompasses both "aminocarbonyl" and "carbonylamino". These terms when used alone or in connection with another group refer to an amido group such as —N(R$^X$)—C(O)—R$^Y$ or —C(O)—N(R$^X$)2, when used terminally, and —C(O)—N(R$^X$)— or —N(R$^X$)—C(O)— when used internally, wherein RX and RY are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aralkyl" group refers to an alkyl group (e.g., a C$_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogens.

For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —N$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$S(O)$_2$—R$^Z$ when used terminally; or —S(O)$_2$—N— or —N$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$)N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$— where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R$_1$, R$_2$, and R$_3$, and other variables contained in formulae described herein encompass specific groups, such as alkyl and aryl. Unless otherwise noted, each of the specific groups for the variables R$_1$, R$_2$, and R$_3$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this disclosure are those combinations that result in the formation of stable or chemically feasible compounds.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇⌇⌇" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

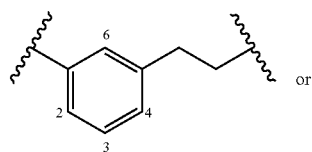

or

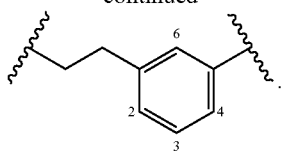

An alkylarylene moiety may be substituted (e.g. with a substituent group) on the alkylene moiety or the arylene linker (e.g. at carbons 2, 3, 4, or 6) with halogen, oxo, —N₃, —CF₃, —CCl₃, —CBr₃, —CI₃, —CN, —CHO, —OH, —NH₂, —COOH, —CONH₂, —NO₂, —SH, —SO₂CH₃— SO₃H, —OSO₃H, —SO₂NH₂, —NHNH₂, —ONH₂, —NHC(O)NHNH₂, substituted or unsubstituted C₁-C₅ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —NR'SO₂R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —R', —N₃, —CH(Ph)₂, fluoro($C_1$-$C_4$)alkoxy, and fluoro($C_1$-$C_4$)alkyl, —NR'$SO_2$R'', —NR'C(O)R'', —NR'C(O)—OR'', —NR'OR'', in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R'', R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C''R''R''')$_d$—, where s and d are independently integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
i) oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
ii) alkyl, heteroalkyl, cycloalkyl, heterocycloalkyl, aryl, heteroaryl, substituted with at least one substituent selected from:
(a) oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.
(c) A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (H), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$ etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of a compound to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

An "MPC modulator" refers to a compound (e.g., compounds described herein) that directly or indirectly modulate the activity of the MPC when compared to a control, such as absence of the compound or a compound with known inactivity.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. In embodiments, the terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences, with or without N-terminus methionine residues; immunologically tagged proteins; and the like.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., MAP kinase pathway).

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc., refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease.

As used herein "metabolic inflammation-mediated disease or disorder" refers to disease states where metabolic inflammation is the basis of the pathology. Metabolic inflammation-mediated disease or disorder are diseases or disorders resulting from metabolic inflammation, including but not limited hypertension, diabetes (e.g., diabetes mellitus type 2), diabetes, metabolic syndrome, all aspects of insulin resistance associated with metabolic syndrome (including dyslipidemia and central obesity as well as fatty liver disease and NASH).

As used herein "metabolic syndrome" is a clustering of at least three of the five following medical conditions: abdominal obesity, high blood pressure, high blood sugar, high serum triglycerides and low high-density lipoprotein (HDL) levels and insulin resistance.

As used herein "non-alcoholic fatty liver disease" and "NAFLD" are interchangeable and refer to fatty liver, which occurs when fat is deposited (steatosis) in the liver due to causes other than excessive alcohol use. Non-alcoholic fatty liver disease (NAFLD) may be related to insulin resistance and the metabolic syndrome.

As used herein "non-alcoholic steatohepatitis" and "NASH" are interchangeable and refer to the most extreme form of non-alcoholic fatty liver disease (NAFLD) as defined by histopathology, particularly hepatocyte ballooning and fibrotic scarring.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound (e.g., a MPC modulator) of the present disclosure may be particularly efficacious (due to, for example, limitations of current therapies) are described in more detail hereafter.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than occurs absent treatment. In embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. An "activity increasing amount," as used herein, refers to an amount of agonist required to increase the activity of an enzyme relative to the absence of the agonist. A "function enhancing amount," as used herein, refers to an amount of agonist required to enhance the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a MPC modulator (or e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). The compound of the disclosure can be administered alone or can be coadministered to the patient.

Coadministration is meant to include simultaneous or sequential administration of the compound individually or in combination (more than one compound or agent). Thus, the preparations can also be combined, when desired, with other active substances (e.g. to reduce metabolic degradation). The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. These patents are incorporated herein by reference for such disclosure. The compositions of the present disclosure can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J Hosp. Pharm.* 46:1576-1587, 1989). The compositions of the present disclosure can also be delivered as nanoparticles.

By "co-administer" it is meant that a composition described herein is administered at the same time, just prior to, or just after the administration of one or more additional therapies. The compounds of the disclosure can be administered alone or can be coadministered to the patient. Coadministration is meant to include simultaneous or sequential administration of the compounds individually or in combination (more than one compound). The compositions of the present disclosure can be delivered transdermally, by a topical route, or formulated as applicator sticks, solutions, suspensions, emulsions, gels, creams, ointments, pastes, jellies, paints, powders, and aerosols.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. colon cancer), cardiovascular disease, metabolic disease, immune or inflammatory disease or disorder.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. colon cancer), cardiovascular disease, metabolic disease, immune or inflammatory disease or disorder.

"Cardiovascular agent" is used in accordance with its plain ordinary meaning and refers to a composition (e.g. compound, drug, antagonist, inhibitor, modulator) used in any way to treat conditions of the heart or the circulatory or vascular system. In some embodiments, a cardiovascular agent is an agent identified herein having utility in methods of treating cardiovascular disease or disorder. In some embodiments, a cardiovascular agent is an agent approved by the FDA or similar regulatory agency of a country other than the USA, for treating cardiovascular disease or disorder.

"Anti-inflammatory agent" is used in accordance with its plain ordinary meaning and refers to a composition (e.g., compound, drug, antagonist, inhibitor, modulator) used in any way to reduce inflammation or swelling. In some embodiments, an anti-inflammatory agent is an agent identified herein having utility in methods of treating an inflammatory disease or disorder. In some embodiments, an anti-inflammatory agent is an agent approved by the FDA or similar regulatory agency of a country other than the USA, for reducing swelling and inflammation.

The compounds described herein can be administered to treat an immune or inflammatory disease or disorder, a cardiovascular or metabolic disease or disorder and/or cancer. In this regard, the compounds disclosed herein may be administered either alone to treat such diseases or disorders or may be co-administered with another therapeutic agent to treat such diseases or disorders.

The compounds disclosed herein may be co-administered with an anti-inflammatory agent, such as thalidomide or a derivative thereof, a retinoid, dithranol or calcipotriol, a non-steroidal anti-inflammatory agent (hereinafter NSAID) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The compounds disclosed herein may be co-administered with a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The compounds (e.g., MPC modulators) disclosed herein can be administered by any acceptable route, such oral, intraadiposal, intraarterial, intraarticular, intracranial, intradermal, intralesional, intramuscular, intranasal, intraocularal, intrapericardial, intraperitoneal, intrapleural, intraprostatical, intrarectal, intrathecal, intratracheal, intratumoral, intraumbilical, intravaginal, intravenous, intravesicullar, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

The compounds (e.g., MPC modulators) disclosed herein may be administered once daily until study reached endpoint. The immune modulator disclosed herein may be administered at least three times but in some studies four or more times depending on the length of the study and/or the design of the study.

The methods disclosed herein may be used in combination with additional therapies (e.g., additional therapeutic agents) for metabolic inflammation-mediated diseases or disorders, metabolic syndrome, non-alcoholic fatty liver disease (NAFLD), and non-alcoholic steatohepatitis (NASH). In some embodiments, the additional therapies (e.g., additional therapeutic agents) include, but are not limited to, GLP1 agonist (such as exenatide, liraglutide, semaglutide, or dulaglutide), a phosphodiesterase (PDE) inhibitor (such as PDE4 and/or a PDE5 inhibitor, pentoxifylline, theophylline, ibudilast, roflumilast, sildenafil, or tadalafil), or a thyroid hormone beta receptor agonist (such as MGL-3196, VK2809, or VK0214).

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a MPC-associated disease modulator is a compound that reduces the severity of one or more symptoms of a disease associated with MPC and/or PPAR (e.g., metabolic inflammation-mediated disease or disorder (e.g., diabetes mellitus type 2), metabolic syndrome, non-alcoholic fatty liver disease (NAFLD), and/or non-alcoholic steatohepatitis (NASH)). A MPC modulator is a compound that increases or decreases the activity or function or level of activity or level of function of MPC. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, the terms "modulate" "modulation" and the like refer to the ability of a molecule (e.g., an activator or an inhibitor) to increase or decrease the function or activity of MPC or PPAR, either directly or indirectly, relative to the absence of the molecule.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-diseaseassociated amount (e.g., by administering a compound or using a method as described herein), results in reduction of the disease or one or more disease symptoms.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

The terms "specifically binds" and "selectively binds," when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least 10-times greater, at least 20-times greater, or at least 100-times greater than the affinity with any other antibody, or binding composition derived therefrom. In embodiments, the antibody will have an affinity that is greater than about 109 liters/mol, as determined by, e.g., Scatchard analysis (Munsen, et al. (1980) Analyt. Biochem. 107:220-239).

The terms "DNA," "nucleic acid," "nucleic acid molecule," "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein, the terms "variants" and "homologs" are used interchangeably to refer to amino acid or nucleic acid sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring amino acid and nucleic acid sequences encoded thereby and their isoforms, as well as splice variants of a protein or gene. The terms also encompass nucleic acid sequences that vary in one or more bases from a naturally-occurring nucleic acid sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

II. COMPOUNDS

In an aspect provided herein, is a compound having structural Formula (I):

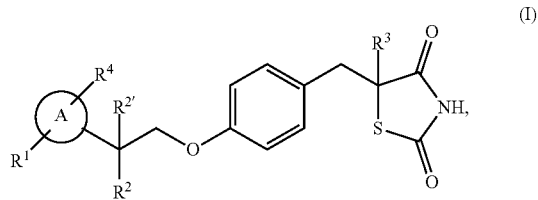

or a pharmaceutically acceptable salt thereof, wherein:
  $R^1$ is hydrogen, halogen, substituted or unsubstituted alkyl, or —$OR^{1A}$;
  $R^2$ is halogen, hydroxyl, or optionally substituted aliphatic;
  $R^{2'}$ is hydrogen, or $R^2$ and $R^{2'}$ may optionally be joined to form oxo;
  $R^3$ is hydrogen or deuterium;
  $R^4$ is hydrogen, halogen, substituted or unsubstituted alkyl, or —$OR^{4A}$;
  A is phenyl; and
  $R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^3$ is hydrogen.

In some embodiments, $R^4$ is independently hydrogen, methyl, or —$OR^{4A}$; and $R^{4A}$ is independently methyl, ethyl, isopropyl, —$CHF_2$, or —$CF_3$. In some embodiments, $R^4$ is hydrogen.

In some embodiments, $R^1$ is hydrogen, halogen or —$OR^{1A}$; and $R^{1A}$ is substituted or unsubstituted alkyl. In some embodiments, $R^{1A}$ is substituted or unsubstituted $C_1$-$C_3$alkyl. In some embodiments, $R^{1A}$ is —$CHF_2$ or —$CF_3$. In some embodiments, $R^1$ is hydrogen. In some embodiments, $R^1$ is —$OR^{1A}$; and $R^{1A}$ is substituted or unsubstituted alkyl. In some embodiments, $R^1$ is halogen. In some embodiments, $R^1$ is —F or —Cl. In some embodiments, $R^1$ is attached to the para or meta position of the phenyl. $R^1$ is attached to the ortho or meta position of the phenyl. In some embodiments, $R^1$ is attached to the meta position of the phenyl.

In some embodiments, $R^2$ is hydrogen. In some embodiments, $R^2$ is hydroxyl. In some embodiments, $R^2$ and $R^{2'}$ are joined to form oxo.

In some embodiments, the compound of Formula (I) is:

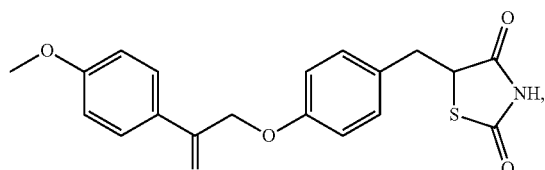

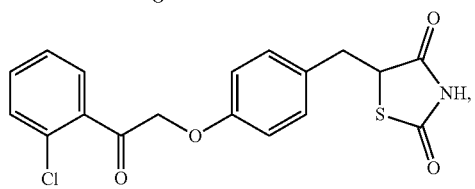

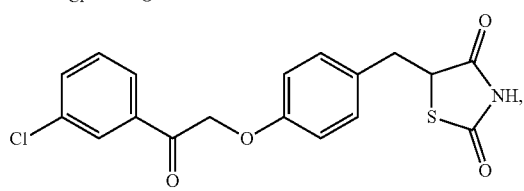

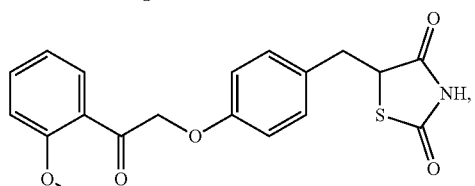

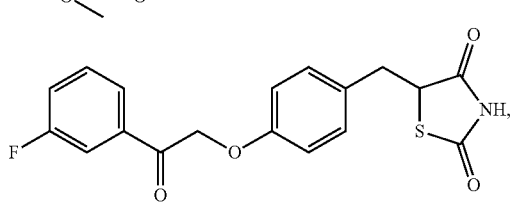

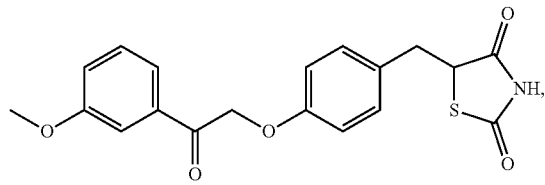

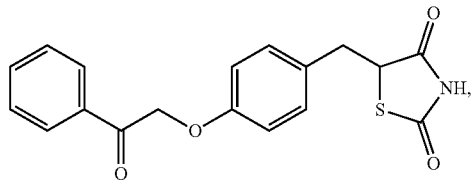 [SMILES: O=C1NC(=O)C(Cc2ccc(OCC(=O)c3ccccc3F)cc2)S1]

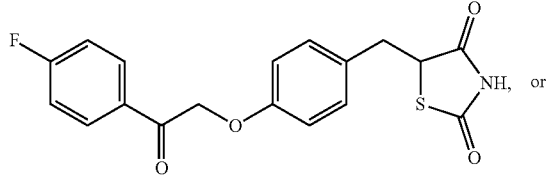

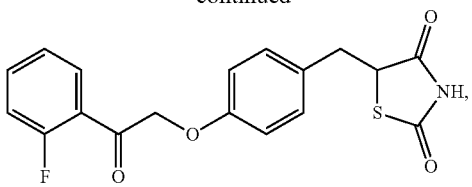

or a pharmaceutically acceptable salt thereof.

In some embodiments, the compound of Formula (I) is:

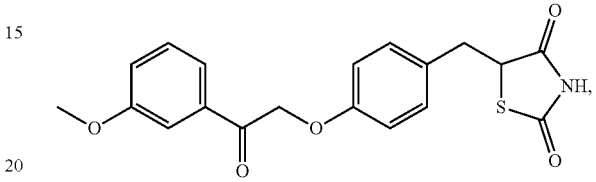

or a pharmaceutically acceptable salt thereof.

III. COMPOSITIONS

In an aspect is provided a composition, including (i) a compound having structural Formula (I):

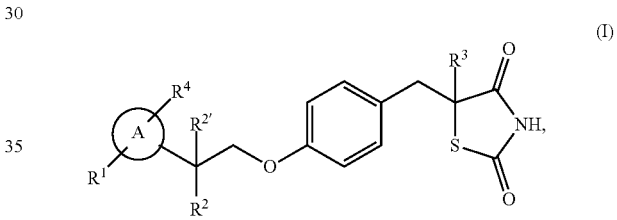

(I)

or a pharmaceutically acceptable salt thereof, and (ii) at least one additional therapeutic agent selected from a GLP1 agonist, a phosphodiesterase (PDE) inhibitor, and a thyroid hormone beta receptor agonist. In the compound having structural Formula (I), $R^1$ is independently hydrogen, halogen, substituted or unsubstituted alkyl, or —$OR^{1A}$. $R^2$ is halogen, hydroxyl, or optionally substituted aliphatic. $R^{2'}$ is hydrogen, or $R^2$ and $R^{2'}$ may optionally be joined to form oxo. $R^3$ is hydrogen or deuterium. $R^4$ is independently hydrogen, halogen, substituted or unsubstituted alkyl, or —$OR^{4A}$. A is phenyl. $R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In an aspect is provided a pharmaceutical composition, including a compound as described herein, including embodiments, or the structural Formula (I), and at least one pharmaceutically acceptable excipient.

In an aspect is provided a pharmaceutical composition, including a compound as described herein, including embodiments, or the structural Formula (I); at least one additional therapeutic agent selected from a GLP1 agonist, a phosphodiesterase (PDE) inhibitor, and a thyroid hormone beta receptor agonist; and at least one pharmaceutically acceptable excipient.

In an aspect is provided a pharmaceutical composition, including a compound of structural Formula:

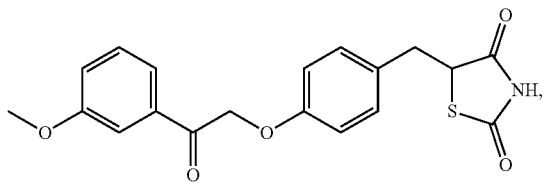 [SMILES: COc1cccc(C(=O)COc2ccc(CC3SC(=O)NC3=O)cc2)c1]

or a pharmaceutically acceptable salt thereof, at least one additional therapeutic agent selected from a GLP1 agonist, a phosphodiesterase (PDE) inhibitor, and a thyroid hormone beta receptor agonist; and at least one pharmaceutically acceptable excipient.

In some embodiments, the at least one additional therapeutic agent is a GLP1 agonist. In some embodiments, the GLP1 agonist is exenatide, liraglutide, semaglutide, or dulaglutide. In some embodiments, the GLP1 agonist is exenatide. In some embodiments, the at least one additional therapeutic agent is a PDE inhibitor. In some embodiments, PDE inhibitor is a PDE4 and/or a PDE5 inhibitor. In some embodiments, PDE inhibitor is pentoxifylline, theophylline, ibudilast, roflumilast, sildenafil, or tadalafil. In some embodiments, the at least one additional therapeutic agent is a thyroid hormone beta receptor agonist. In some embodiments, the thyroid hormone beta receptor agonist is MGL-3196, VK2809, or VK0214.

In an aspect is provided a pharmaceutical composition, including a compound of structural Formula:

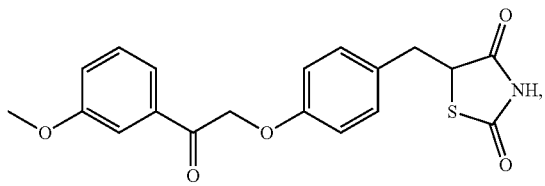 [SMILES: COc1cccc(C(=O)COc2ccc(CC3SC(=O)NC3=O)cc2)c1]

or a pharmaceutically acceptable salt thereof; exenatide, liraglutide, semaglutide, or dulaglutide; and a at least one pharmaceutically acceptable excipient.

In some embodiments, the pharmaceutically acceptable salt is a potassium salt.

The compounds (e.g., MPC or PPAR modulator(s)) of the present disclosure may be in the form of compositions suitable for administration to a subject. In general, such compositions are "pharmaceutical compositions" comprising a compound (e.g., MPC or PPAR modulator(s)) and one or more pharmaceutically acceptable or physiologically acceptable diluents, carriers or excipients. In some embodiments, the compounds (e.g., MPC or PPAR modulator(s)) are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., a modulator of MPC or PPAR function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a MPC or PPAR modulator contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a MPC or PPAR modulator, including implants (e.g., implantable pumps) and catheter systems, slow injection pumps and devices, all of which are well known to the skilled artisan.

Depot injections, which are generally administered subcutaneously or intramuscularly, may also be utilized to release the compound (e.g., MPC or PPAR modulator) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, NJ) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compound (e.g., MPC or PPAR modulator) in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compound (e.g., MPC or PPAR modulator) contemplated by the present disclosure may be in the form of any other suitable pharmaceutical composition (e.g., sprays for nasal or inhalation use) currently known or developed in the future.

IV. METHODS

Provided herein is a method of treating non-alcoholic fatty liver disease (NAFLD) and/or metabolic syndrome, comprising administering to a subject in need thereof:

(i) a therapeutically effective amount of a compound of structural Formula (I):

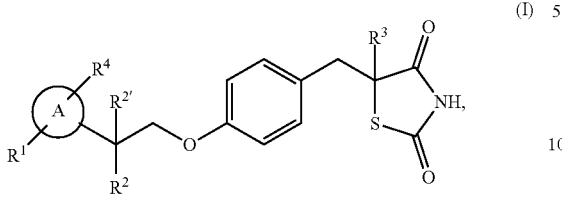

or a pharmaceutically acceptable salt thereof, wherein:
R$^1$ is hydrogen, halogen, substituted or unsubstituted alkyl, or —OR$^{1A}$;
R$^2$ is halogen, hydroxyl, or optionally substituted aliphatic;
R$^{2'}$ is hydrogen, or R$^2$ and R$^{2'}$ may optionally be joined to form oxo;
R$^3$ is hydrogen or deuterium;
R$^4$ is hydrogen, halogen, substituted or unsubstituted alkyl, or —OR$^{4A}$;
A is phenyl; and
R$^{1A}$ and R$^{4A}$ are independently hydrogen, halogen, —CF$_3$, —CCl$_3$, —CBr$_3$, —CI$_3$, —CHF$_2$, —CHCl$_2$, —CHBr$_2$, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
(ii) at least one additional therapeutic agent selected from a GLP1 agonist, a phosphodiesterase (PDE) inhibitor, and a thyroid hormone beta receptor agonist.

Provided herein is a method of treating non-alcoholic fatty liver disease (NAFLD) and/or at least one metabolic inflammation-mediated disease or disorder, comprising administering to a subject in need thereof:
(i) a therapeutically effective amount of a compound of structural Formula (I):

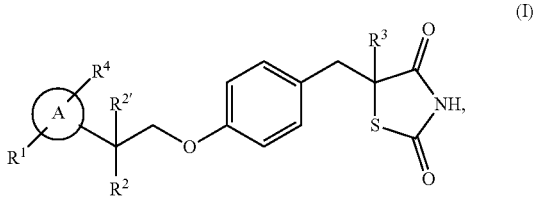

or a pharmaceutically acceptable salt thereof, wherein:
R$^1$ is hydrogen, halogen, substituted or unsubstituted alkyl, or —OR$^{1A}$;
R$^2$ is halogen, hydroxyl, or optionally substituted aliphatic;
R$^{2'}$ is hydrogen, or R$^2$ and R$^{2'}$ may optionally be joined to form oxo;
R$^3$ is hydrogen or deuterium;
R$^4$ is hydrogen, halogen, substituted or unsubstituted alkyl, or —OR$^{4A}$;
A is phenyl; and
R$^{1A}$ and R$^{4A}$ are independently hydrogen, halogen, —CF$_3$, —CCl$_3$, —CBr$_3$, —CI$_3$, —CHF$_2$, —CHCl$_2$, —CHBr$_2$, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
(ii) at least one additional therapeutic agent selected from a phosphodiesterase (PDE) inhibitor, a thyroid hormone beta receptor agonist, or a GLP1 agonist. In some embodiments, the GLP1 agonist is liraglutide, semaglutide, or dulaglutide.

Provided herein is a method of treating non-alcoholic fatty liver disease (NAFLD) and/or metabolic syndrome, comprising administering to a subject in need thereof:
(i) a therapeutically effective amount of a pharmaceutical composition, comprising a compound of structural Formula (I):

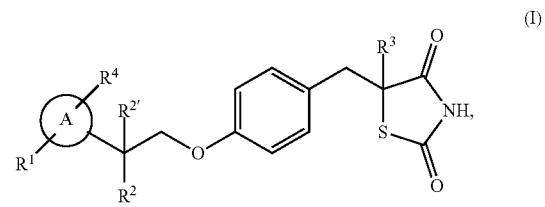

or a pharmaceutically acceptable salt thereof, and a pharmaceutically acceptable excipient, wherein:
R$^1$ is hydrogen, halogen, substituted or unsubstituted alkyl, or —OR$^{1A}$;
R$^2$ is halogen, hydroxyl, or optionally substituted aliphatic;
R$^{2'}$ is hydrogen, or R$^2$ and R$^{2'}$ may optionally be joined to form oxo;
R$^3$ is hydrogen or deuterium;
R$^4$ is hydrogen, halogen, substituted or unsubstituted alkyl, or —OR$^{4A}$.
A is phenyl; and
R$^{1A}$ and R$^{4A}$ are independently hydrogen, halogen, —CF$_3$, —CCl$_3$, —CBr$_3$, —CI$_3$, —CHF$_2$, —CHCl$_2$, —CHBr$_2$, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
(ii) at least one additional therapeutic agent selected from a GLP1 agonist, a phosphodiesterase (PDE) inhibitor, or a thyroid hormone beta receptor agonist.

Provided herein is a method of treating non-alcoholic fatty liver disease (NAFLD) and/or at least one metabolic inflammation-mediated disease or disorder, comprising administering to a subject in need thereof a therapeutically effective amount of a pharmaceutical composition comprising:
(i) a compound of structural Formula (I), or a pharmaceutically acceptable salt thereof:

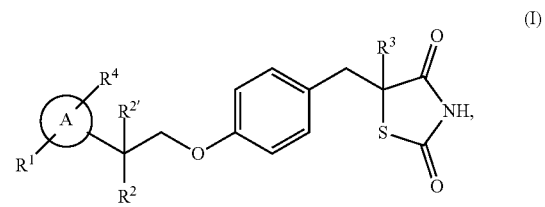

wherein:
R¹ is hydrogen, halogen, substituted or unsubstituted alkyl, or —OR^{1A};
R² is halogen, hydroxyl, or optionally substituted aliphatic;
R²' is hydrogen, or R² and R²' may optionally be joined to form oxo;
R³ is hydrogen or deuterium;
R⁴ is hydrogen, halogen, substituted or unsubstituted alkyl, or —OR^{4A};
A is phenyl; and
R^{1A} and R^{4A} are independently hydrogen, halogen, —CF₃, —CCl₃, —CBr₃, —CI₃, —CHF₂, —CHCl₂, —CHBr₂, —CHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
(ii) at least one additional therapeutic agent selected from a GLP1 agonist, a phosphodiesterase (PDE) inhibitor, or a thyroid hormone beta receptor agonist; and
(iii) and a pharmaceutically acceptable excipient, wherein the compound of Formula (I) and the at least one additional therapeutic agent selected from a GLP1 agonist, a phosphodiesterase (PDE) inhibitor, or a thyroid hormone beta receptor agonist are co-formulated.

Provided is a method of treating non-alcoholic fatty liver disease (NAFLD) and/or metabolic syndrome, comprising administering to a subject in need thereof a therapeutically effective amount of a pharmaceutical composition, comprising a compound of structural formula:

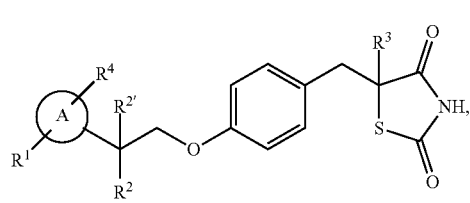

or a pharmaceutically acceptable salt thereof, a GLP1 agonist, and a pharmaceutically acceptable excipient. In some embodiments, the GLP1 agonist is exenatide, liraglutide, semaglutide, or dulaglutide.

Provided is a method of treating at least one metabolic inflammation-mediated disease or disorder, comprising administering to a subject in need thereof a therapeutically effective amount of a compound of structural Formula (I):

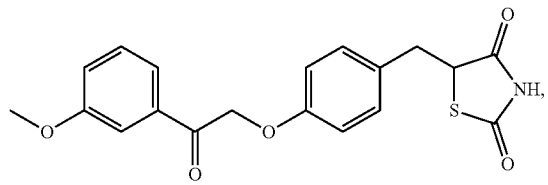 [SMILES: COc1cccc(C(=O)COc2ccc(CC3SC(=O)NC3=O)cc2)c1]

or a pharmaceutically acceptable salt thereof, wherein:
R¹ is hydrogen, halogen, substituted or unsubstituted alkyl, or —OR^{1A};
R² is halogen, hydroxyl, or optionally substituted aliphatic;
R²' is hydrogen, or R² and R²' may optionally be joined to form oxo;
R³ is deuterium;
R⁴ is hydrogen, halogen, substituted or unsubstituted alkyl, or —OR^{4A};
A is phenyl; and
R^{1A} and R^{4A} are independently hydrogen, halogen, —CF₃, —CCl₃, —CBr₃, —CI₃, —CHF₂, —CHCl₂, —CHBr₂, —CHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Provided herein is a method of inhibiting hepatic mitochondrial pyruvate carrier (MPC) in a cell, comprising contacting the MPC with a compound of structural Formula (I):

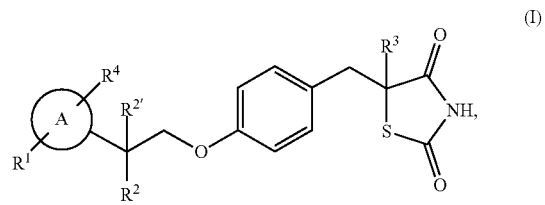

or a pharmaceutically acceptable salt thereof, wherein:
R¹ is hydrogen, halogen, substituted or unsubstituted alkyl, or —OR^{1A};
R² is halogen, hydroxyl, or optionally substituted aliphatic;
R²' is hydrogen, or R² and R²' may optionally be joined to form oxo;
R³ is hydrogen or deuterium;
R⁴ is hydrogen, halogen, substituted or unsubstituted alkyl, or —OR^{4A};
A is phenyl; and
R^{1A} and R^{4A} are independently hydrogen, halogen, —CF₃, —CCl₃, —CBr₃, —CI₃, —CHF₂, —CHCl₂, —CHBr₂, —CHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, the cell is a hepatocyte.

Provided herein is a method of improving or increasing glucose tolerance and/or insulin sensitivity, comprising administering to a subject in need thereof a therapeutically effective amount of a compound of structural Formula (I):

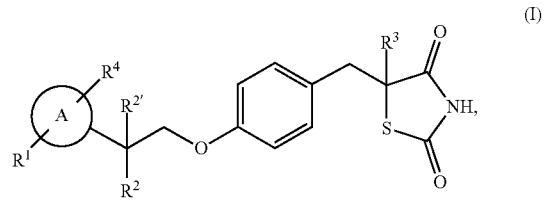

or a pharmaceutically acceptable salt thereof, wherein:
R¹ is hydrogen, halogen, substituted or unsubstituted alkyl, or —OR^{1A};
R² is halogen, hydroxyl, or optionally substituted aliphatic;

R[2'] is hydrogen, or R[2] and R[2'] may optionally be joined to form oxo;
R[3] is hydrogen or deuterium;
R[4] is hydrogen, halogen, substituted or unsubstituted alkyl, or —OR[4A];
A is phenyl; and
R[1A] and R[4A] are independently hydrogen, halogen, —CF$_3$, —CCl$_3$, —CBr$_3$, —CI$_3$, —CHF$_2$, —CHCl$_2$, —CHBr$_2$, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Provided herein is a method of treating or preventing a hepatic disease, disorder, or injury, comprising administering to a subject in need thereof a therapeutically effective amount of a compound of structural Formula (I):

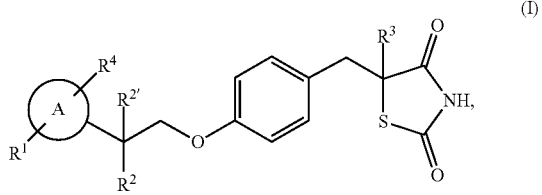

(I)

or a pharmaceutically acceptable salt thereof, wherein:
R[1] is hydrogen, halogen, substituted or unsubstituted alkyl, or —OR[1A];
R[2] is halogen, hydroxyl, or optionally substituted aliphatic;
R[2'] is hydrogen, or R[2] and R[2'] may optionally be joined to form oxo;
R[3] is hydrogen or deuterium;
R[4] is hydrogen, halogen, substituted or unsubstituted alkyl, or —OR[4A];
A is phenyl; and
R[1A] and R[4A] are independently hydrogen, halogen, —CF$_3$, —CCl$_3$, —CBr$_3$, —CI$_3$, —CHF$_2$, —CHCl$_2$, —CHBr$_2$, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Provided herein is a method of treating or preventing hepatocyte fibrogenesis, comprising administering to a subject in need thereof a therapeutically effective amount of a compound of structural Formula (I):

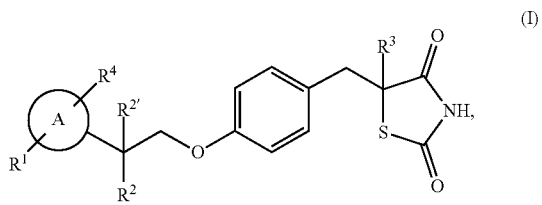

(I)

or a pharmaceutically acceptable salt thereof, wherein:
R[1] is hydrogen, halogen, substituted or unsubstituted alkyl, or —OR[1A];
R[2] is halogen, hydroxyl, or optionally substituted aliphatic;
R[2'] is hydrogen, or R[2] and R[2'] may optionally be joined to form oxo;
R[3] is hydrogen or deuterium;
R[4] is hydrogen, halogen, substituted or unsubstituted alkyl, or —OR[4A];
A is phenyl; and
R[1A] and R[4A] are independently hydrogen, halogen, —CF$_3$, —CCl$_3$, —CBr$_3$, —CI$_3$, —CHF$_2$, —CHCl$_2$, —CHBr$_2$, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl In some embodiments, R[3] is hydrogen.

In some embodiments, R[4] is independently hydrogen, methyl, or —OR[4A]; and R[4A] is independently methyl, ethyl, isopropyl, —CHF$_2$, or —CF$_3$. In some embodiments, R[4] is hydrogen.

In some embodiments, R[1] is hydrogen, halogen or —OR[1A]; and R[1A] is substituted or unsubstituted alkyl. In some embodiments, R[1A] is substituted or unsubstituted C$_1$-C$_3$alkyl. In some embodiments, R[1A] is —CHF$_2$ or —CF$_3$. In some embodiments, R[1] is hydrogen. In some embodiments, R[1] is —OR[1A]; and R[1A] is substituted or unsubstituted alkyl. In some embodiments, R[1] is halogen. In some embodiments, R[1] is —F or —Cl. In some embodiments, R[1] is attached to the para or meta position of the phenyl. R[1] is attached to the ortho or meta position of the phenyl. In some embodiments, R[1] is attached to the meta position of the phenyl.

In some embodiments, R[2'] is hydrogen. In some embodiments, R[2] is hydroxyl. In some embodiments, R[2] and R[2'] are joined to form oxo.

In some embodiments, the compound of Formula (I) is:

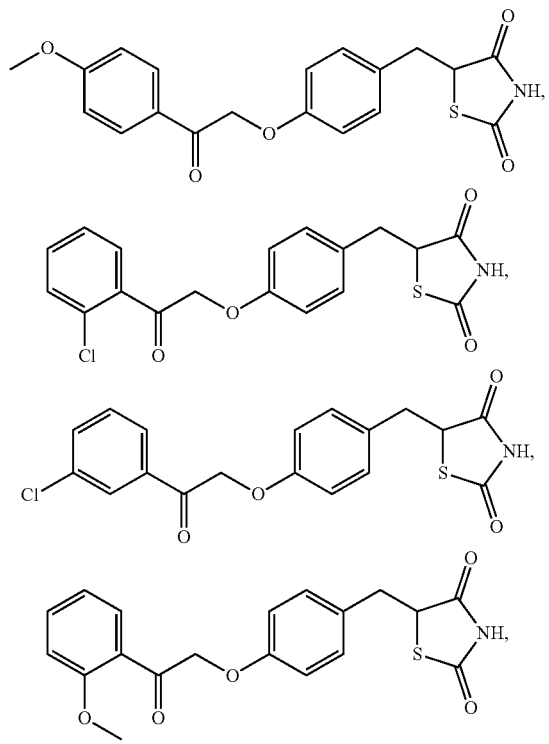

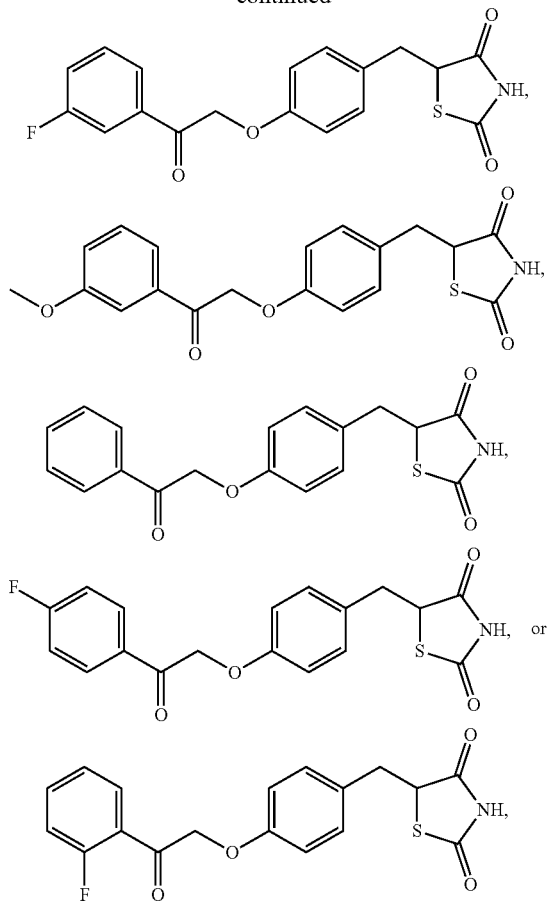

or a pharmaceutically acceptable salt thereof.

In some embodiments, the compound of Formula (I) is:

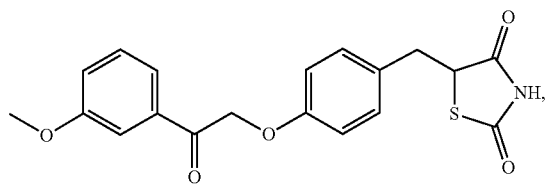

or a pharmaceutically acceptable salt thereof.

In some embodiments, the pharmaceutically acceptable salt is a potassium salt.

In some embodiments, the compound of Formula (I), or a pharmaceutically acceptable salt thereof, is co-formulated with the at least one additional therapeutic agent.

In some embodiments, the compound of Formula (I), or a pharmaceutically acceptable salt thereof, is administered orally.

In some embodiments, the compound of Formula (I), or a pharmaceutically acceptable salt thereof, is formulated as a tablet or capsule.

In some embodiments, in the treatment, prevention, or amelioration of one or more symptoms of the disorders, diseases, or conditions described herein (e.g., treatment or prevention of at least one metabolic inflammation-mediated disease or disorder), an appropriate dosage level of a compound of Formula (I), or a pharmaceutically acceptable salt, solvate, hydrate, or prodrug thereof generally is ranging from about 1 to 3000 mg, from about 1 to 2000 mg, from about 1 to 1000 mg, from about 1 to about 500 mg, from about 5 to about 500 mg, from about 5 to about 400 mg, from about 5 to about 300 mg, from about 5 to about 250 mg, from about 5 to about 125 mg or from about 62.5 to about 250 mg, which can be administered in single or multiple doses. In some embodiments, the compound of Formula (I), or a pharmaceutically acceptable salt, solvate, hydrate, or prodrug thereof is administered in an amount of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 300, 350, 400, or 500 mg. In some embodiments, the compound of Formula (I), or a pharmaceutically acceptable salt, solvate, hydrate, or prodrug thereof is administered in an amount of about 60, 60.5, 61, 61.5, 62, 62.5, 63, 63.5, 64, 64.5, 65, 65.5, 66, 66.5, 67, 67.5, 68, 68.5, 69, 69.5, or 70 mg. In some embodiments, the compound of Formula (I), or a pharmaceutically acceptable salt, solvate, hydrate, or prodrug thereof is administered in an amount of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 300, 350, 400, or 500 mg/day. In some embodiments, the compound of Formula (I), or a pharmaceutically acceptable salt, solvate, hydrate, or prodrug thereof is administered in an amount of about 60, 60.5, 61, 61.5, 62, 62.5, 63, 63.5, 64, 64.5, 65, 65.5, 66, 66.5, 67, 67.5, 68, 68.5, 69, 69.5, or 70 mg/day.

For oral administration, the pharmaceutical compositions provided herein can be formulated in the form of tablets or capsules containing from about 1.0 to about 1,000 mg of a compound of Formula (I), or a pharmaceutically acceptable salt, solvate, hydrate, or prodrug thereof. In some embodiments, for oral administration, the pharmaceutical compositions provided herein can be formulated in the form of tablets or capsules containing about 1, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205 mg, about 210 mg, about 215 mg, about 220 mg, about 225 mg, about 230 mg, about 235 mg, about 240 mg, about 245 mg, about 250 mg, about 300 mg, about 350 mg, about 400 mg, or about 500 mg of a compound of Formula (I), or a pharmaceutically acceptable salt, solvate, hydrate, or prodrug thereof for the symptomatic adjustment of the dosage to the patient to be treated. In embodiments, for oral administration, the pharmaceutical compositions provided herein can be formulated in the form of tablets or capsules containing about 60, 60.5, 61, 61.5, 62, 62.5, 63, 63.5, 64, 64.5, 65, 65.5, 66, 66.5, 67, 67.5, 68, 68.5, 69, 69.5, or 70 mg of a compound of Formula (I), or a pharmaceutically acceptable salt, solvate, hydrate, or prodrug thereof for the symptomatic adjustment of the dosage to the patient to be treated.

The pharmaceutical compositions can be administered on a regimen of one (1) to four (4) times per day, including once, twice, three times, and four times per day. In some embodiments, the compound of Formula (I), or an isotopic variant thereof, or a pharmaceutically acceptable salt, solvate, hydrate, or prodrug thereof is administered once per day.

In some embodiments, the compound of Formula (I), or a pharmaceutically acceptable salt thereof, is administered in a dose of from about 60 mg to about 250 mg. In some embodiments, the compound of Formula (I), or a pharmaceutically acceptable salt thereof, is administered in a dose of about 62.5 mg. In some embodiments, the compound of Formula (I), or a pharmaceutically acceptable salt thereof, is administered in a dose of about 125 mg. In some embodiments, the compound of Formula (I), or a pharmaceutically acceptable salt thereof, is administered in a dose of about 250 mg.

In some embodiments, the compound of Formula (I), or a pharmaceutically acceptable salt thereof, is administered daily. In some embodiments, the compound of Formula (I), or a pharmaceutically acceptable salt thereof, is administered once daily.

In some embodiments, the GLP1 agonist is administered orally, by injection, or by an implantable mini-pump. In some embodiments, the GLP1 agonist is administered by an implantable mini-pump. In some embodiments, the implantable mini-pump is a 6-month pump. In some embodiments, a single implantable mini-pump is used.

In some embodiments, the GLP1 agonist is administered by injection. In some embodiments, the GLP1 agonist is injected approximately once monthly. In some embodiments, the GLP1 agonist is injected for a period of up to about 6 months. In some embodiments, the GLP1 agonist is injected approximately once weekly. In some embodiments, the GLP1 agonist is injected approximately once weekly for a period of up to about 25 weeks.

In some embodiments, the PDE inhibitor is administered orally. In some embodiments, the PDE inhibitor is administered for a period of up to about 6 months.

In some embodiments, the compound of Formula (I), or a pharmaceutically acceptable salt thereof, and the at least one additional therapeutic agent are administered simultaneously, approximately simultaneously, or sequentially, in any order.

In some embodiments, the compound of Formula (I), or a pharmaceutically acceptable salt thereof, and the at least one additional therapeutic agent are administered simultaneously or approximately simultaneously.

In some embodiments, the compound of Formula (I), or a pharmaceutically acceptable salt thereof, and the at least one additional therapeutic agent are administered sequentially. In some embodiments, the compound of Formula (I), or a pharmaceutically acceptable salt thereof, is administered before the at least one additional therapeutic agent. In some embodiments, the compound of Formula (I), or a pharmaceutically acceptable salt thereof, is administered after the at least one additional therapeutic agent.

Provided herein is a method of treating or preventing non-alcoholic fatty liver disease (NAFLD) and/or metabolic syndrome, comprising administering to a subject in need thereof a therapeutically effective amount of a compound as described herein, including embodiments, or the structural Formula (I), or a pharmaceutically acceptable salt thereof, and at least one additional therapeutic agent selected from a GLP1 agonist, a phosphodiesterase (PDE) inhibitor, and a thyroid hormone beta receptor agonist.

Provided herein is a method of treating or preventing non-alcoholic fatty liver disease (NAFLD) and/or at least one metabolic inflammation-mediated disease or disorder, comprising administering to a subject in need thereof a therapeutically effective amount of a pharmaceutical composition comprising:
(i) a compound of structural Formula (I), or a pharmaceutically acceptable salt thereof:

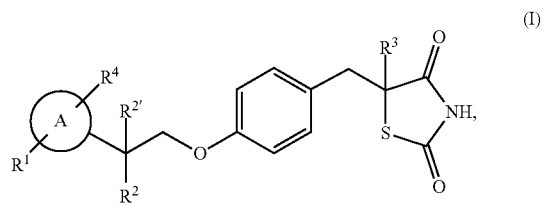

wherein $R^1$, $R^2$, $R^{2'}$, $R^3$, and $R^4$ are as described herein, including embodiments;
(ii) at least one additional therapeutic agent selected from a GLP1 agonist, a phosphodiesterase (PDE) inhibitor, or a thyroid hormone beta receptor agonist; and
(iii) and a pharmaceutically acceptable excipient, wherein the compound of Formula (I) and the at least one additional therapeutic agent selected from a GLP1 agonist, a phosphodiesterase (PDE) inhibitor, or a thyroid hormone beta receptor agonist are co-formulated.

In an aspect is provided a method of treating at least one metabolic inflammation-mediated disease or disorder, comprising administering to a subject in need thereof a therapeutically effective amount of a compound of structural Formula (I), or a pharmaceutically acceptable salt thereof:

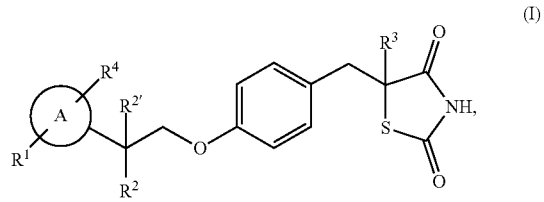

wherein $R^1$, $R^2$, $R^{2'}$, and $R^4$ are as described herein, including embodiments. $R^3$ is deuterium.

In some embodiments, the subject has NAFLD. In some embodiments, the subject has at least one metabolic inflammation-mediated disease or disorder. In some embodiments, the subject has NAFLD and at least one metabolic inflammation-mediated disease or disorder. In some embodiments, the subject has (NAFLD) and/or metabolic syndrome and at least one metabolic inflammation-mediated disease or disorder. In some embodiments, the subject has diabetes mellitus, NAFLD, or metabolic syndrome, or any combination thereof. In some embodiments, the subject is suffering from obesity, non-alcoholic fatty liver disease (NAFLD), a metabolic inflammation-mediated disease or disorder, metabolic syndrome, or any combination thereof.

In some embodiments, the NAFLD is non-alcoholic steatohepatitis (NASH). In some embodiments, the subject has NASH with fibrosis.

In some embodiments, the at least one metabolic inflammation-mediated disease or disorder is diabetes mellitus type 2.

In another aspect is provided a method of inhibiting hepatocyte mitochondrial pyruvate carrier (MPC), comprising contacting the MPC with a compound as described herein, including embodiments, or the structural Formula (I), or a pharmaceutically acceptable salt thereof. In aspect is provided a method of inhibiting hepatocyte mitochondrial pyruvate carrier (MPC), comprising contacting the MPC with a compound as described herein, including embodiments, or the structural Formula (I).

In some embodiments, the hepatocyte is in vivo. In some embodiments, the hepatocyte is a human hepatocyte.

In an aspect is provided a method of improving or increasing glucose tolerance and/or insulin sensitivity, comprising administering to a subject in need thereof a therapeutically effective amount of a compound as described herein, including embodiments, or the structural Formula (I), or a pharmaceutically acceptable salt thereof. In an aspect is provided a method of improving or increasing glucose tolerance and/or insulin sensitivity, comprising: administering to a subject in need thereof a therapeutically effective amount of a compound as described herein, including embodiments, or the structural Formula (I), or a pharmaceutically acceptable salt thereof, and an additional therapeutic agent.

In an aspect is provided a method of treating or preventing a hepatic disease, disorder, or injury, comprising administering to a subject in need thereof a therapeutically effective amount of a compound as described herein, including embodiments, or the structural Formula (I), or a pharmaceutically acceptable salt thereof. In an aspect is provided a method of treating or preventing a hepatic disease, disorder, or injury, comprising: administering to a subject in need thereof a therapeutically effective amount of a compound as described herein, including embodiments, or the structural Formula (I), or a pharmaceutically acceptable salt thereof, and an additional therapeutic agent.

In some embodiments, the hepatic disease, disorder, or injury is fibrosis.

In an aspect is provided a method of treating or preventing hepatocyte fibrogenesis, comprising administering to a subject in need thereof a therapeutically effective amount of a compound as described herein, including embodiments, or the structural Formula (I), or a pharmaceutically acceptable salt thereof. In an aspect is provided a method of treating or preventing hepatocyte fibrogenesis, comprising: administering to a subject in need thereof a therapeutically effective amount of a compound as described herein, including embodiments, or the structural Formula (I), or a pharmaceutically acceptable salt thereof, and an additional therapeutic agent.

In some embodiments, the at least one additional therapeutic agent is a GLP1 agonist. In some embodiments, the GLP1 agonist is exenatide, liraglutide, semaglutide, or dulaglutide. In some embodiments, the GLP1 agonist is exenatide.

In some embodiments, the at least one additional therapeutic agent is a PDE inhibitor. In some embodiments, PDE inhibitor is a PDE4 and/or a PDE5 inhibitor. In some embodiments, PDE inhibitor is pentoxifylline, theophylline, ibudilast, roflumilast, sildenafil, or tadalafil.

In some embodiments, the at least one additional therapeutic agent is a thyroid hormone beta receptor agonist. In some embodiments, the thyroid hormone beta receptor agonist is MGL-3196, VK2809, or VK0214.

Additional Embodiments include Embodiments 1 to 186 following.

Embodiment 1. A method of treating non-alcoholic fatty liver disease (NAFLD) and/or metabolic syndrome, comprising administering to a subject in need thereof:
  (i) a therapeutically effective amount of a compound of structural Formula (I):

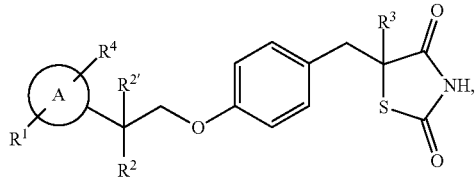

or a pharmaceutically acceptable salt thereof, wherein:
  $R^1$ is hydrogen, halogen, substituted or unsubstituted alkyl, or $-OR^{1A}$;
  $R^2$ is halogen, hydroxyl, or optionally substituted aliphatic;
  $R^{2'}$ is hydrogen, or $R^2$ and $R^{2'}$ may optionally be joined to form oxo;
  $R^3$ is hydrogen or deuterium;
  $R^4$ is hydrogen, halogen, substituted or unsubstituted alkyl, or $-OR^{4A}$;
  A is phenyl; and
  $R^{1A}$ and $R^{4A}$ are independently hydrogen, halogen, $-CF_3$, $-CCl_3$, $-CBr_3$, $-CI_3$, $-CHF_2$, $-CHCl_2$, $-CHBr_2$, $-CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
  (ii) at least one additional therapeutic agent selected from a GLP1 agonist, a phosphodiesterase (PDE) inhibitor, and a thyroid hormone beta receptor agonist.

Embodiment 2. The method of embodiment 1, wherein $R^3$ is hydrogen.

Embodiment 3. The method of embodiment 2, wherein $R^4$ is:
  hydrogen, methyl, or $-OR^{4A}$; and
  $R^{4A}$ is methyl, ethyl, isopropyl, $-CHF_2$, or $-CF_3$ Embodiment 4. The method of embodiment 3, wherein $R^4$ is hydrogen.

Embodiment 5. The method of embodiment 1, wherein $R^1$ is:
  hydrogen, halogen, or $-OR^{1A}$; and
  $R^{1A}$ is substituted or unsubstituted alkyl.

Embodiment 6. The method of embodiment 5, wherein $R^1$ is hydrogen.

Embodiment 7. The method of embodiment 5, wherein $R^1$ is halogen.

Embodiment 8. The method of embodiment 5, wherein $R^1$ is $-OR^{1A}$ and $R^{1A}$ is substituted or unsubstituted alkyl.

Embodiment 9. The method of embodiment 7, wherein $R^1$ is attached to the para or meta position of the phenyl.

Embodiment 10. The method of embodiment 7, wherein $R^1$ is attached to the meta position of the phenyl.

Embodiment 11. The method of embodiment 9, wherein $R^1$ is $-F$ or $-Cl$.

Embodiment 12. The method of embodiment 8, wherein $R^1$ is attached to the ortho or meta position of the phenyl.

Embodiment 13. The method of embodiment 8, wherein $R^1$ is attached to the meta position of the phenyl.

Embodiment 14. The method of embodiment 12, wherein $R^{1A}$ is substituted or unsubstituted $C_1$-$C_3$alkyl.

Embodiment 15. The method of embodiment 14, wherein $R^{1A}$ is $-CHF_2$ or $-CF_3$.

Embodiment 16. The method of embodiment 1, wherein $R^{2'}$ is hydrogen.

Embodiment 17. The method of embodiment 16, wherein $R^2$ is hydroxyl.

Embodiment 18. The method of embodiment 1, wherein $R^2$ and $R^{2a}$ are joined to form oxo.

Embodiment 19. The method of embodiment 1, wherein the compound of Formula (I) is:

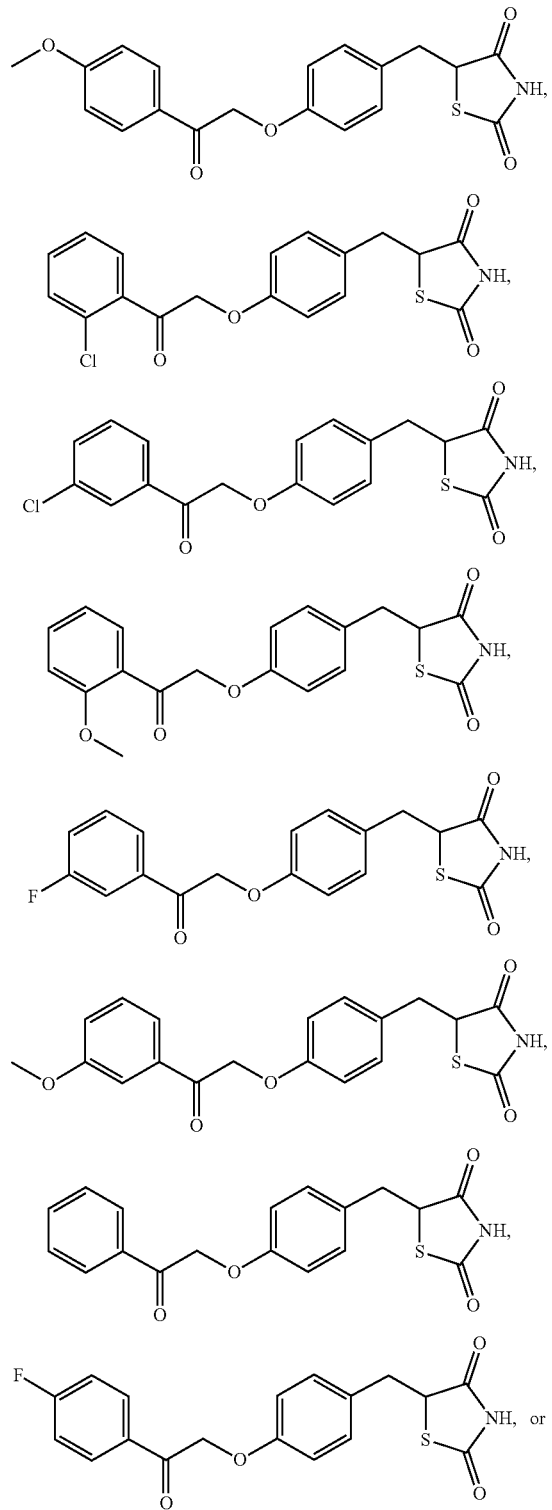

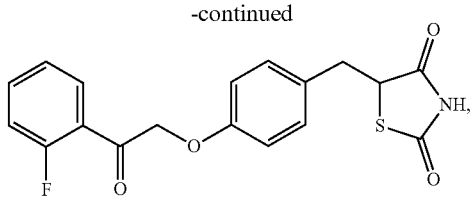

or a pharmaceutically acceptable salt thereof.

Embodiment 20. The method of embodiment 1, wherein the compound of Formula (I) is.

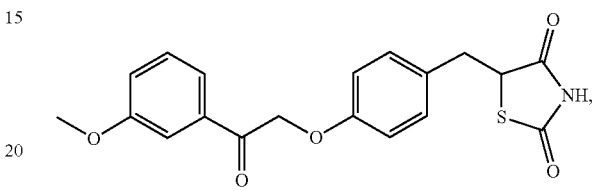

or a pharmaceutically acceptable salt thereof.

Embodiment 21. The method of embodiment 1, wherein the GLP1 agonist is exenatide, liraglutide, semaglutide, or dulaglutide.

Embodiment 22. The method of embodiment 21, wherein the GLP1 agonist is exenatide.

Embodiment 23. The method of embodiment 1, wherein the PDE inhibitor is a PDE4 and/or a PDE5 inhibitor.

Embodiment 24. The method of embodiment 1, wherein the PDE inhibitor is pentoxifylline, theophylline, ibudilast, roflumilast, sildenafil, or tadalafil.

Embodiment 25. The method of embodiment 1, wherein the thyroid hormone beta receptor agonist is MGL-3196, VK2809, or VK0214.

Embodiment 26. The method of any one of embodiments 1-25, wherein the compound of Formula (I), or a pharmaceutically acceptable salt thereof, is administered orally.

Embodiment 27. The method of any one of embodiments 1-26, wherein the compound of Formula (I), or a pharmaceutically acceptable salt thereof, is formulated as a tablet or capsule.

Embodiment 28. The method of any one of embodiments 1-27, wherein the compound of Formula (I), or a pharmaceutically acceptable salt thereof, is administered in a dose of from about 60 mg to about 250 mg.

Embodiment 29. The method of any one of embodiments 1-28, wherein the compound of Formula (I), or a pharmaceutically acceptable salt thereof, is administered daily.

Embodiment 30. The method of any one of embodiments 1-29, wherein the compound of Formula (I), or a pharmaceutically acceptable salt thereof, is administered once daily.

Embodiment 31. The method of any one of embodiments 1-30, wherein the GLP1 agonist is administered orally, by injection, or by an implantable mini-pump.

Embodiment 32. The method of embodiment 31, wherein the GLP1 agonist is administered by an implantable mini-pump.

Embodiment 33. The method of embodiment 31 or 32, wherein the implantable mini-pump is a 6-month pump.

Embodiment 34. The method of any one of embodiments 31-33, wherein a single implantable mini-pump is used.

Embodiment 35. The method of embodiment 31, wherein the GLP1 agonist is administered by injection.

Embodiment 36. The method of embodiment 31 or 35, wherein the GLP1 agonist is injected approximately once monthly.

Embodiment 37. The method of embodiment 36, wherein the GLP1 agonist is injected for a period of up to about 6 months.

Embodiment 38. The method of embodiment 31 or 35, wherein the GLP1 agonist is injected approximately once weekly.

Embodiment 39. The method of embodiment 38, wherein the GLP1 agonist is injected approximately once weekly for a period of up to about 25 weeks.

Embodiment 40. The method of any one of embodiments 1-30, wherein the PDE inhibitor is administered orally.

Embodiment 41. The method of embodiment 40, wherein the PDE inhibitor is administered for a period of up to about 6 months.

Embodiment 42. The method of any one of embodiments 1-41, wherein the compound of Formula (I), or a pharmaceutically acceptable salt thereof, and the at least one additional therapeutic agent are administered simultaneously, approximately simultaneously, or sequentially, in any order.

Embodiment 43. The method of embodiment 42, wherein the compound of Formula (I), or a pharmaceutically acceptable salt thereof, and the at least one additional therapeutic agent are administered simultaneously or approximately simultaneously.

Embodiment 44. The method of embodiment 42, wherein the compound of Formula (I), or a pharmaceutically acceptable salt thereof, and the at least one additional therapeutic agent are administered sequentially.

Embodiment 45. The method of embodiment 44, wherein the compound of Formula (I), or a pharmaceutically acceptable salt thereof, is administered before the at least one additional therapeutic agent.

Embodiment 46. The method of embodiment 44, wherein the compound of Formula (I), or a pharmaceutically acceptable salt thereof, is administered after the at least one additional therapeutic agent.

Embodiment 47. The method of any one of embodiments 1-31 or 40-46, wherein the compound of Formula (I), or a pharmaceutically acceptable salt thereof, is co-formulated with the at least one additional therapeutic agent.

Embodiment 48. The method of any one of embodiments 1-47, wherein the NAFLD is non-alcoholic steatohepatitis (NASH).

Embodiment 49. The method of any one of embodiments 1-48, further wherein the subject has at least one metabolic inflammation-mediated disease or disorder.

Embodiment 50. The method of embodiment 49, wherein the at least one metabolic inflammation-mediated disease or disorder is diabetes mellitus type 2.

Embodiment 51. A method of treating non-alcoholic fatty liver disease (NAFLD) and/or at least one metabolic inflammation-mediated disease or disorder, comprising administering to a subject in need thereof
(i) a therapeutically effective amount of a compound of structural Formula (I):

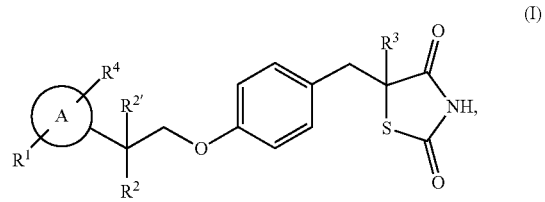

or a pharmaceutically acceptable salt thereof, wherein:
$R^1$ is hydrogen, halogen, substituted or unsubstituted alkyl, or —$OR^{1A}$.
$R^2$ is halogen, hydroxyl, or optionally substituted aliphatic;
$R^{2'}$ is hydrogen, or $R^2$ and $R^{2'}$ may optionally be joined to form oxo;
$R^3$ is hydrogen or deuterium;
$R^4$ is hydrogen, halogen, substituted or unsubstituted alkyl, or —$OR^{4A}$.
A is phenyl; and
$R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
(ii) at least one additional therapeutic agent selected from a phosphodiesterase (PDE) inhibitor, a thyroid hormone beta receptor agonist, or a GLP1 agonist.

Embodiment 52. The method of embodiment 51, wherein the GLP1 agonist is liraglutide, semaglutide, or dulaglutide Embodiment 53. The method of embodiment 52, wherein $R^3$ is hydrogen.

Embodiment 54. The method of embodiment 53, wherein $R^4$ is:
hydrogen, methyl, or —$OR^{4A}$; and
$R^{4A}$ is methyl, ethyl, isopropyl, —$CHF_2$, or —$CF_3$.

Embodiment 55. The method of embodiment 54, wherein $R^4$ is hydrogen.

Embodiment 56. The method of embodiment 52, wherein $R^1$ is:
hydrogen, halogen, or —$OR^{1A}$; and
$R^{1A}$ is substituted or unsubstituted alkyl.

Embodiment 57. The method of embodiment 56, wherein $R^1$ is hydrogen.

Embodiment 58. The method of embodiment 56, wherein $R^1$ is halogen.

Embodiment 59. The method of embodiment 56, wherein $R^1$ is —$OR^{1A}$ and $R^{1A}$ is substituted or unsubstituted alkyl.

Embodiment 60. The method of embodiment 58, wherein $R^1$ is attached to the para or meta position of the phenyl.

Embodiment 61. The method of embodiment 58, wherein $R^1$ is attached to the meta position of the phenyl.

Embodiment 62. The method of embodiment 60, wherein $R^1$ is —F or —Cl.

Embodiment 63. The method of embodiment 59, wherein $R^1$ is attached to the ortho or meta position of the phenyl.

Embodiment 64. The method of embodiment 59, wherein $R^1$ is attached to the meta position of the phenyl.

Embodiment 65. The method of embodiment 63, wherein $R^{1A}$ is substituted or unsubstituted $C_1$-$C_3$alkyl.

Embodiment 66. The method of embodiment 65, wherein $R^{1A}$ is —$CHF_2$ or —$CF_3$.

Embodiment 67. The method of embodiment 52, wherein $R^{2'}$ is hydrogen.

Embodiment 68. The method of embodiment 67, wherein $R^2$ is hydroxyl.

Embodiment 69. The method of embodiment 52, wherein $R^2$ and $R^{2a}$ are joined to form oxo.

Embodiment 70. The method of embodiment 52, wherein the compound of Formula (I) is:

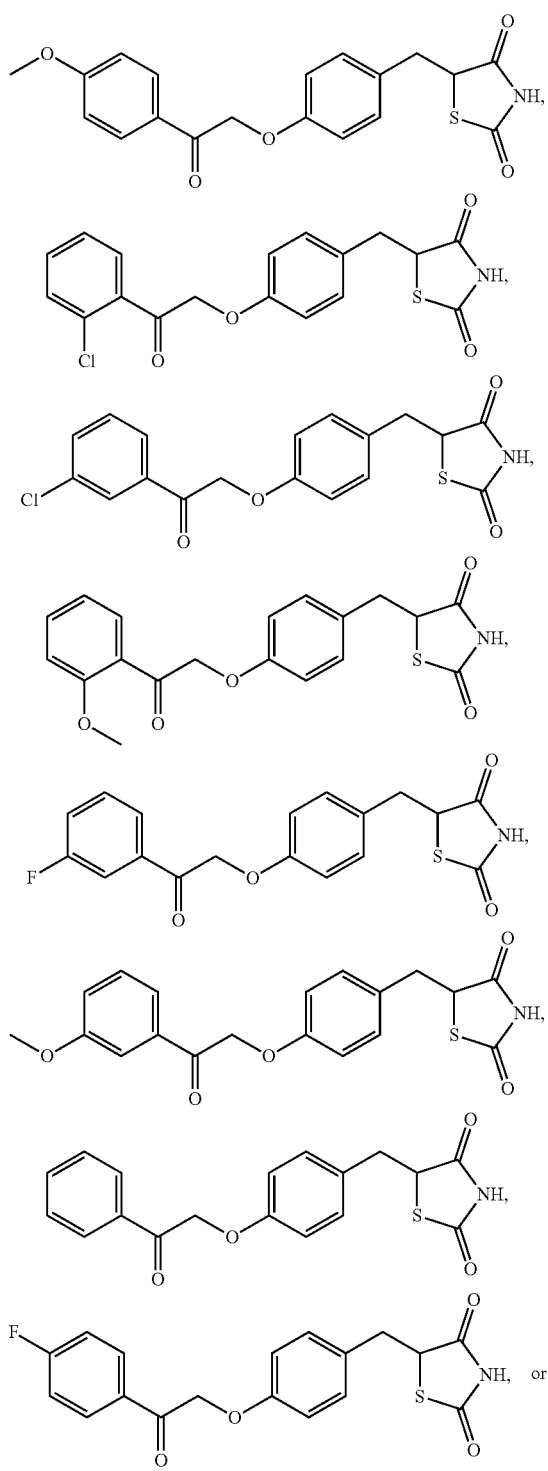
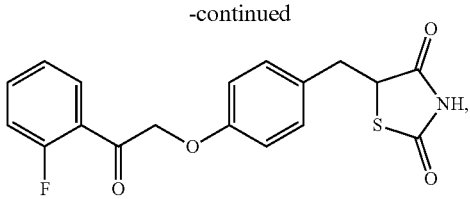

or a pharmaceutically acceptable salt thereof.

Embodiment 71. The method of embodiment 52, wherein the compound of Formula (I) is:

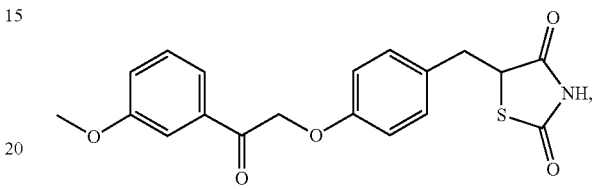

or a pharmaceutically acceptable salt thereof.

Embodiment 72. The method of embodiment 52, wherein the PDE inhibitor is a PDE4 and/or a PDE5 inhibitor.

Embodiment 73. The method of embodiment 52, wherein the PDE inhibitor is pentoxifylline, theophylline, ibudilast, roflumilast, sildenafil, or tadalafil.

Embodiment 74. The method of embodiment 52, wherein the thyroid hormone beta receptor agonist is MGL-3196, VK2809, or VK0214.

Embodiment 75. The method of any one of embodiments 52-74, wherein the compound of Formula (I), or a pharmaceutically acceptable salt thereof, is administered orally.

Embodiment 76. The method of any one of embodiments 52-75, wherein the compound of Formula (I), or a pharmaceutically acceptable salt thereof, is formulated as a tablet or capsule.

Embodiment 77. The method of any one of embodiments 52-76, wherein the compound of Formula (I), or a pharmaceutically acceptable salt thereof, is administered in a dose of from about 60 mg to about 250 mg.

Embodiment 78. The method of any one of embodiments 52-77, wherein the compound of Formula (I), or a pharmaceutically acceptable salt thereof, is administered daily.

Embodiment 79. The method of any one of embodiments 52-78, wherein the compound of Formula (I), or a pharmaceutically acceptable salt thereof, is administered once daily.

Embodiment 80. The method of any one of embodiments 52-79, wherein the PDE inhibitor is administered orally.

Embodiment 81. The method of embodiment 80, wherein the PDE inhibitor is administered for a period of up to about 6 months.

Embodiment 82. The method of any one of embodiments 52-81, wherein the compound of Formula (I), or a pharmaceutically acceptable salt thereof, and the at least one additional therapeutic agent are administered simultaneously, approximately simultaneously, or sequentially in any order.

Embodiment 83. The method of embodiment 82, wherein the compound of Formula (I), or a pharmaceutically acceptable salt thereof, and the at least one additional therapeutic agent are administered simultaneously or approximately simultaneously.

Embodiment 84. The method of embodiment 82, wherein the compound of Formula (I), or a pharmaceutically acceptable salt thereof, and the at least one additional therapeutic agent are administered sequentially.

Embodiment 85. The method of embodiment 84, wherein the compound of Formula (I), or a pharmaceutically acceptable salt thereof, is administered before the at least one additional therapeutic agent.

Embodiment 86. The method of embodiment 84, wherein the compound of Formula (I), or a pharmaceutically acceptable salt thereof, is administered after the at least one additional therapeutic agent.

Embodiment 87. The method of any one of embodiments 52-83, wherein the compound of Formula (I), or a pharmaceutically acceptable salt thereof, is co-formulated with the at least one additional therapeutic agent.

Embodiment 88. The method of any one of embodiments 52-87, wherein the NAFLD is non-alcoholic steatohepatitis (NASH).

Embodiment 89. The method of any one of embodiments 52-88, wherein the subject has diabetes mellitus, NAFLD, or metabolic syndrome, or any combination thereof.

Embodiment 90. The method of embodiment 89, wherein the diabetes mellitus is type 2.

Embodiment 91. A method of treating non-alcoholic fatty liver disease (NAFLD) and/or metabolic syndrome, comprising administering to a subject in need thereof:
  (i) a therapeutically effective amount of a pharmaceutical composition, comprising a compound of structural Formula (I):

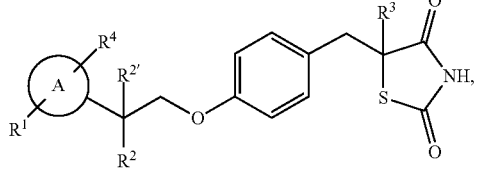

or a pharmaceutically acceptable salt thereof, and a pharmaceutically acceptable excipient, wherein:
  $R^1$ is hydrogen, halogen, substituted or unsubstituted alkyl, or —$OR^{1A}$;
  $R^2$ is halogen, hydroxyl, or optionally substituted aliphatic;
  $R^{2'}$ is hydrogen, or $R^2$ and $R^{2'}$ may optionally be joined to form oxo;
  $R^3$ is hydrogen or deuterium;
  $R^4$ is hydrogen, halogen, substituted or unsubstituted alkyl, or —$OR^{4A}$;
  A is phenyl; and
  $R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
  (ii) at least one additional therapeutic agent selected from a GLP1 agonist, a phosphodiesterase (PDE) inhibitor, or a thyroid hormone beta receptor agonist.

Embodiment 92. A method of treating non-alcoholic fatty liver disease (NAFLD) and/or at least one metabolic inflammation-mediated disease or disorder, comprising administering to a subject in need thereof a therapeutically effective amount of a pharmaceutical composition comprising:
  (i) a compound of structural Formula (I), or a pharmaceutically acceptable salt thereof:

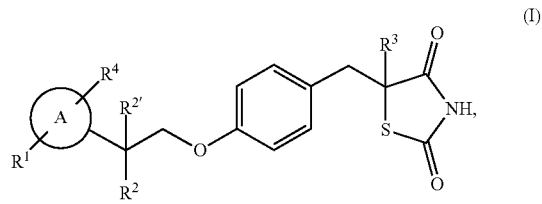

wherein:
  $R^1$ is hydrogen, halogen, substituted or unsubstituted alkyl, or —$OR^{1A}$;
  $R^2$ is halogen, hydroxyl, or optionally substituted aliphatic;
  $R^{2'}$ is hydrogen, or $R^2$ and $R^{2'}$ may optionally be joined to form oxo;
  $R^3$ is hydrogen or deuterium;
  $R^4$ is hydrogen, halogen, substituted or unsubstituted alkyl, or —$OR^{4A}$;
  A is phenyl; and
  $R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
  (ii) at least one additional therapeutic agent selected from a GLP1 agonist, a phosphodiesterase (PDE) inhibitor, or a thyroid hormone beta receptor agonist; and
  (iii) and a pharmaceutically acceptable excipient, wherein the compound of Formula (I) and the at least one additional therapeutic agent selected from a GLP1 agonist, a phosphodiesterase (PDE) inhibitor, or a thyroid hormone beta receptor agonist are co-formulated.

Embodiment 93. The method of embodiment 91 or 92, wherein the compound of Formula (I) is:

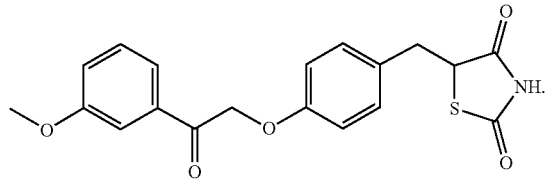 [SMILES: COc1cccc(C(=O)COc2ccc(CC3SC(=O)NC3=O)cc2)c1]

or a pharmaceutically acceptable salt thereof.

Embodiment 94. The method of any one of embodiments 1-93, wherein the pharmaceutically acceptable salt is a potassium salt.

Embodiment 95. A pharmaceutical composition, comprising a compound of structural formula:

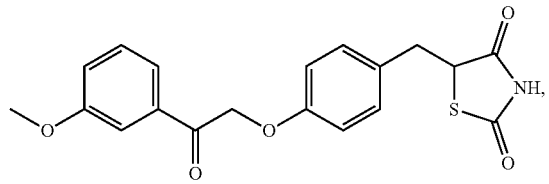

or a pharmaceutically acceptable salt thereof, a GLP1 agonist, and a pharmaceutically acceptable excipient.

Embodiment 96. The pharmaceutical composition of embodiment 96, wherein the GLP1 agonist is exenatide, liraglutide, semaglutide, or dulaglutide.

Embodiment 97. The pharmaceutical composition of embodiment 95 or 96, wherein the pharmaceutically acceptable salt is a potassium salt.

Embodiment 98. A method of treating non-alcoholic fatty liver disease (NAFLD) and/or metabolic syndrome, comprising administering to a subject in need thereof a therapeutically effective amount of the pharmaceutical composition of any one of embodiments 95-97.

Embodiment 99. A method of treating at least one metabolic inflammation-mediated disease or disorder, comprising administering to a subject in need thereof a therapeutically effective amount of a compound of structural Formula (I):

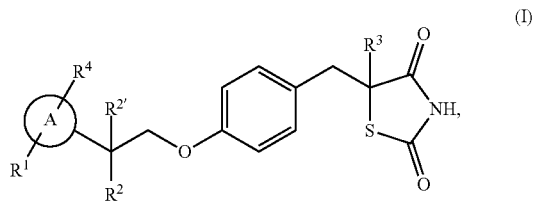

or a pharmaceutically acceptable salt thereof, wherein:
$R^1$ is hydrogen, halogen, substituted or unsubstituted alkyl, or —$OR^{1A}$;
$R^2$ is halogen, hydroxyl, or optionally substituted aliphatic;
$R^{2'}$ is hydrogen, or $R^2$ and $R^{2'}$ may optionally be joined to form oxo;
$R^3$ is deuterium;
$R^4$ is hydrogen, halogen, substituted or unsubstituted alkyl, or —$OR^{4A}$;
A is phenyl; and $R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 100. The method of embodiment 99, wherein $R^4$ is:
hydrogen, methyl, or —$OR^{4A}$; and
$R^{4A}$ is methyl, ethyl, isopropyl, —$CHF_2$, or —$CF_3$.

Embodiment 101. The method of embodiment 100, wherein $R^4$ is hydrogen.

Embodiment 102. The method of embodiment 99, wherein $R^1$ is:
hydrogen, halogen, or —$OR^{1A}$; and
$R^{1A}$ is substituted or unsubstituted alkyl.

Embodiment 103. The method of embodiment 102, wherein $R^1$ is hydrogen.

Embodiment 104. The method of embodiment 102, wherein $R^1$ is halogen.

Embodiment 105. The method of embodiment 102, wherein $R^1$ is —$OR^{1A}$ and $R^{1A}$ is substituted or unsubstituted alkyl.

Embodiment 106. The method of embodiment 104, wherein $R^1$ is attached to the para or meta position of the phenyl.

Embodiment 107. The method of embodiment 104, wherein $R^1$ is attached to the meta position of the phenyl.

Embodiment 108. The method of embodiment 107, wherein $R^1$ is —F or —Cl.

Embodiment 109. The method of embodiment 105, wherein $R^1$ is attached to the ortho or meta position of the phenyl.

Embodiment 110. The method of embodiment 105, wherein $R^1$ is attached to the meta position of the phenyl.

Embodiment 111. The method of embodiment 105, wherein $R^{1A}$ is substituted or unsubstituted $C_1$-$C_3$alkyl.

Embodiment 112. The method of embodiment 111, wherein $R^{1A}$ is —$CHF_2$ or —$CF_3$.

Embodiment 113. The method of embodiment 99, wherein $R^{2'}$ is hydrogen.

Embodiment 114. The method of embodiment 113, wherein $R^2$ is hydroxyl.

Embodiment 115. The method of embodiment 99, wherein $R^2$ and $R^{2'}$ are joined to form oxo.

Embodiment 116. The method of embodiment 99, wherein the compound of Formula (I) is:

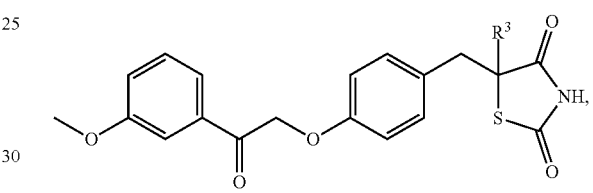

or a pharmaceutically acceptable salt thereof.

Embodiment 117. The method of embodiment 99, wherein the at least one metabolic inflammation-mediated disease or disorder is diabetes mellitus.

Embodiment 118. The method of embodiment 117, wherein the diabetes mellitus is type 2.

Embodiment 119. The method of embodiment 99, wherein the subject has non-alcoholic fatty liver disease (NAFLD).

Embodiment 120. The method of embodiment 119, wherein the NAFLD is non-alcoholic steatohepatitis (NASH).

Embodiment 121. The method of embodiment 99, further comprising administering to the subject at least one additional therapeutic agent selected from a GLP1 agonist, a phosphodiesterase (PDE) inhibitor, or a thyroid hormone beta receptor agonist.

Embodiment 122. The method of embodiment 121, wherein the PDE inhibitor is a PDE4 and/or a PDE5 inhibitor.

Embodiment 123. The method of embodiment 121, wherein the PDE inhibitor is pentoxifylline, theophylline, ibudilast, roflumilast, sildenafil, or tadalafil.

Embodiment 124. The method of embodiment 121, wherein the thyroid hormone beta receptor agonist is MGL-3196, VK2809, or VK0214.

Embodiment 125. The method of embodiment 121, wherein the GLP1 agonist is exenatide, liraglutide, semaglutide, or dulaglutide.

Embodiment 126. A method of inhibiting hepatic mitochondrial pyruvate carrier (MPC) in a hepatocyte, comprising contacting the MPC with a compound of structural Formula (I):

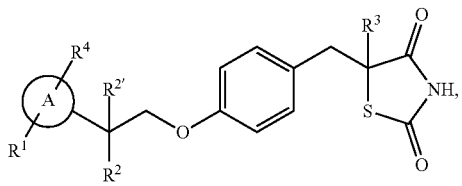

(I)

or a pharmaceutically acceptable salt thereof, wherein:
R$^1$ is hydrogen, halogen, substituted or unsubstituted alkyl, or —OR$^{1A}$;
R$^2$ is halogen, hydroxyl, or optionally substituted aliphatic;
R$^{2'}$ is hydrogen, or R$^2$ and R$^{2'}$ may optionally be joined to form oxo;
R$^3$ is hydrogen or deuterium;
R$^4$ is hydrogen, halogen, substituted or unsubstituted alkyl, or —OR$^{4A}$;
A is phenyl; and
R$^{1A}$ and R$^{4A}$ are independently hydrogen, halogen, —CF$_3$, —CCl$_3$, —CBr$_3$, —CI$_3$, —CHF$_2$, —CHCl$_2$, —CHBr$_2$, —CHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 127. The method of embodiment 126, wherein R$^3$ is hydrogen.

Embodiment 128. The method of embodiment 127, wherein R$^4$ is:
hydrogen, methyl, or —OR$^{4A}$; and
R$^{4A}$ is methyl, ethyl, isopropyl, —CHF$_2$, or —CF$_3$.

Embodiment 129. The method of embodiment 128, wherein R$^4$ is hydrogen.

Embodiment 130. The method of embodiment 126, wherein R$^1$ is:
hydrogen, halogen or —OR$^{1A}$; and
R$^{1A}$ is substituted or unsubstituted alkyl.

Embodiment 131. The method of embodiment 130, wherein R$^1$ is hydrogen.

Embodiment 132. The method of embodiment 130, wherein R$^1$ is halogen.

Embodiment 133. The method of embodiment 130, wherein R$^1$ is —OR$^{1A}$ and R$^{1A}$ is substituted or unsubstituted alkyl.

Embodiment 134. The method of embodiment 132, wherein R$^1$ is attached to the para or meta position of the phenyl.

Embodiment 135. The method of embodiment 132, wherein R$^1$ is attached to the meta position of the phenyl.

Embodiment 136. The method of embodiment 134, wherein R$^1$ is —F or —Cl.

Embodiment 137. The method of embodiment 133, wherein R$^1$ is attached to the ortho or meta position of the phenyl.

Embodiment 138. The method of embodiment 133, wherein R$^1$ is attached to the meta position of the phenyl.

Embodiment 139. The method of embodiment 133, wherein R$^1$ is attached to the meta position of the phenyl.

Embodiment 140. The method of embodiment 139, wherein R$^{1A}$ is —CHF$_2$ or —CF$_3$.

Embodiment 141. The method of embodiment 126, wherein R$^{2'}$ is hydrogen.

Embodiment 142. The method of embodiment 141, wherein R$^2$ is hydroxyl.

Embodiment 143. The method of embodiment 126, wherein R$^2$ and R$^{2'}$ are joined to form oxo.

Embodiment 144. The method of embodiment 126, wherein the compound of Formula (I) is:

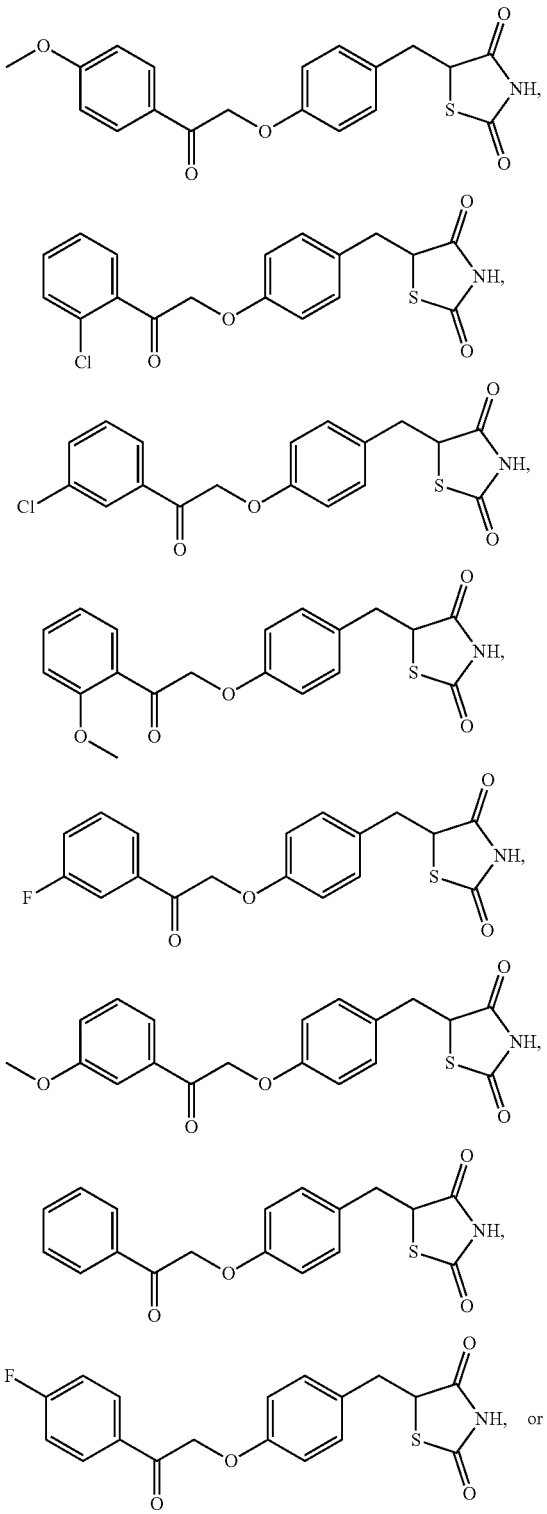

or a pharmaceutically acceptable salt thereof.

Embodiment 145. The method of embodiment 126, wherein the compound of Formula (I) is:

Embodiment 146. The method of embodiment 126, wherein the cell is a hepatocyte.

Embodiment 147. The method of embodiment 146, wherein the hepatocyte is in vivo.

Embodiment 148. The method of embodiment 147, wherein the hepatocyte is a human hepatocyte.

Embodiment 149. The method of any one of embodiments 126-148, wherein the pharmaceutically acceptable salt is a potassium salt.

Embodiment 150. A method of improving or increasing glucose tolerance and/or insulin sensitivity, comprising administering to a subject in need thereof a therapeutically effective amount of a compound of structural Formula (I):

or a pharmaceutically acceptable salt thereof, wherein:
 $R^1$ is hydrogen, halogen, substituted or unsubstituted alkyl, or —$OR^{1A}$;
 $R^2$ is halogen, hydroxyl, or optionally substituted aliphatic;
 $R^{2'}$ is hydrogen, or $R^2$ and $R^{2'}$ may optionally be joined to form oxo;
 $R^3$ is hydrogen or deuterium;
 $R^4$ is hydrogen, halogen, substituted or unsubstituted alkyl, or —$OR^{4A}$;
 A is phenyl; and
 $R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 151. The method of embodiment 150, wherein $R^3$ is hydrogen.

Embodiment 152. The method of embodiment 151, wherein $R^4$ is:
 hydrogen, methyl, or —$OR^{4A}$; and
 $R^{4A}$ is methyl, ethyl, isopropyl, —$CHF_2$, or —$CF_3$.

Embodiment 153. The method of embodiment 152, wherein $R^4$ is hydrogen.

Embodiment 154. The method of embodiment 150, wherein $R^1$ is:
 hydrogen, halogen, or —$OR^{1A}$; and
 $R^{1A}$ is substituted or unsubstituted alkyl.

Embodiment 155. The method of embodiment 154, wherein $R^1$ is hydrogen.

Embodiment 156. The method of embodiment 154, wherein $R^1$ is halogen.

Embodiment 157. The method of embodiment 154, wherein $R^1$ is —$OR^{1A}$ and $R^{1A}$ is substituted or unsubstituted alkyl.

Embodiment 158. The method of embodiment 156, wherein $R^1$ is attached to the para or meta position of the phenyl.

Embodiment 159. The method of embodiment 156, wherein $R^1$ is attached to the meta position of the phenyl.

Embodiment 160. The method of embodiment 158, wherein $R^1$ is —F or —Cl.

Embodiment 161. The method of embodiment 157, wherein $R^1$ is attached to the ortho or meta position of the phenyl.

Embodiment 162. The method of embodiment 157, wherein $R^1$ is attached to the meta position of the phenyl.

Embodiment 163. The method of embodiment 161, wherein $R^{1A}$ is substituted or unsubstituted $C_1$-$C_3$alkyl.

Embodiment 164. The method of embodiment 163, wherein $R^{1A}$ is —$CHF_2$ or —$CF_3$.

Embodiment 165. The method of embodiment 150, wherein $R^{2'}$ is hydrogen.

Embodiment 166. The method of embodiment 165, wherein $R^2$ is hydroxyl.

Embodiment 167. The method of embodiment 150, wherein $R^2$ and $R^{2a}$ are joined to form oxo.

Embodiment 168. The method of embodiment 150, wherein the compound of Formula (I) is:

-continued

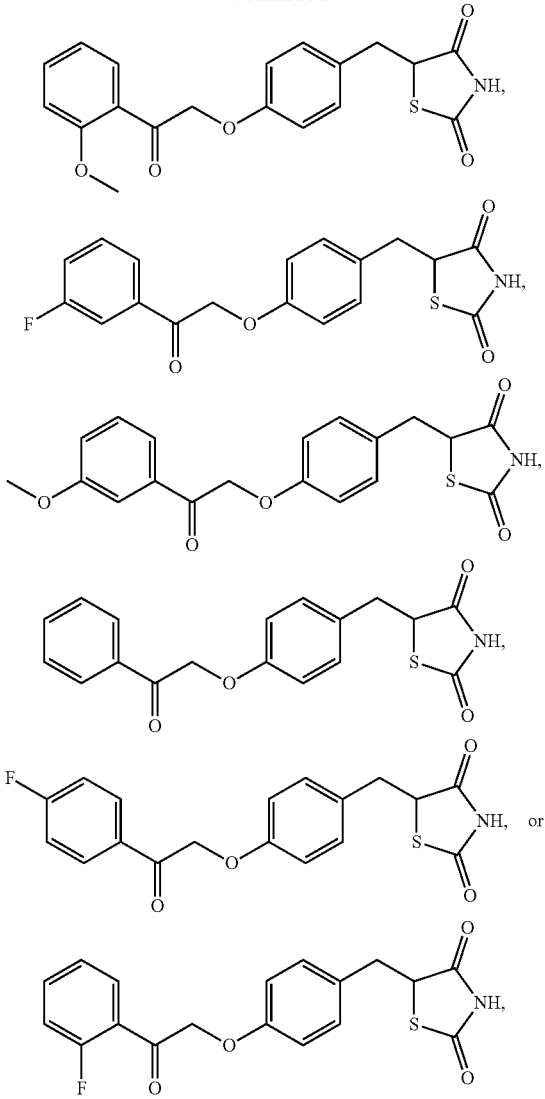

or a pharmaceutically acceptable salt thereof.

Embodiment 169. The method of embodiment 150, wherein the compound of Formula (I) is:

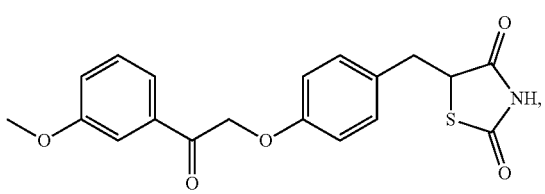 [SMILES: COc1cccc(C(=O)COc2ccc(CC3SC(=O)NC3=O)cc2)c1]

or a pharmaceutically acceptable salt thereof.

Embodiment 170. The method of any one of embodiments 150-169, wherein the subject is suffering from obesity, non-alcoholic fatty liver disease (NAFLD), a metabolic inflammation-mediated disease or disorder, metabolic syndrome, or any combination thereof.

Embodiment 171. The method of embodiment 170, wherein the NAFLD is non-alcoholic steatohepatitis (NASH).

Embodiment 172. The method of any one of embodiments 150-171, wherein the pharmaceutically acceptable salt is a potassium salt.

Embodiment 173. A method of treating or preventing a hepatic disease, disorder, or injury, comprising administering to a subject in need thereof a therapeutically effective amount of a compound of structural Formula (I):

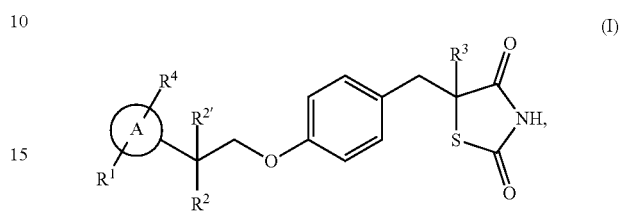

or a pharmaceutically acceptable salt thereof, wherein:
$R^1$ is hydrogen, halogen, substituted or unsubstituted alkyl, or —$OR^{1A}$;
$R^2$ is halogen, hydroxyl, or optionally substituted aliphatic;
$R^{2'}$ is hydrogen, or $R^2$ and $R^{2'}$ may optionally be joined to form oxo;
$R^3$ is hydrogen or deuterium;
$R^4$ is hydrogen, halogen, substituted or unsubstituted alkyl, or —$OR^{4A}$;
A is phenyl; and
$R^{1A}$ and $R^{4A}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 174. The method of embodiment 173, wherein the hepatic disease, disorder, or injury is fibrosis.

Embodiment 175. The method of embodiment 173 or 174, wherein the compound of Formula (I) is:

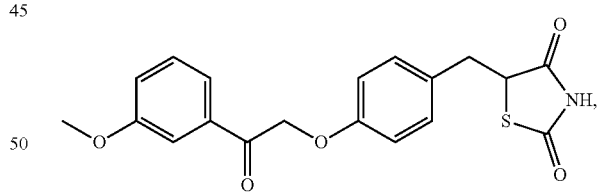

or a pharmaceutically acceptable salt thereof.

Embodiment 176. The method of any one of embodiments 173-175, wherein the subject is suffering from obesity, non-alcoholic fatty liver disease (NAFLD), a metabolic inflammation-mediated disease or disorder, metabolic syndrome, or any combination thereof.

Embodiment 177. The method of any one of embodiments 173-175, wherein the pharmaceutically acceptable salt is a potassium salt.

Embodiment 178. A method of treating or preventing hepatocyte fibrogenesis, comprising administering to a subject in need thereof a therapeutically effective amount of a compound of structural Formula (I):

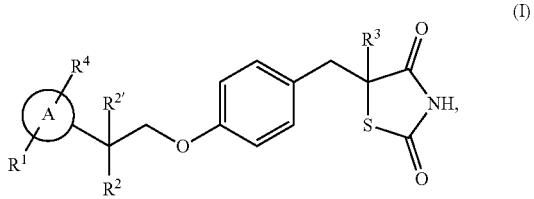

(I)

or a pharmaceutically acceptable salt thereof, wherein:
$R^1$ is hydrogen, halogen, substituted or unsubstituted alkyl, or —$OR^{1.4}$;
$R^2$ is halogen, hydroxyl, or optionally substituted aliphatic;
$R^{2'}$ is hydrogen, or $R^2$ and $R^{2'}$ may optionally be joined to form oxo;
$R^3$ is hydrogen or deuterium;
$R^4$ is hydrogen, halogen, substituted or unsubstituted alkyl, or —$OR^{4.4}$;
A is phenyl; and
$R^{1.4}$ and $R^{4.4}$ are independently hydrogen, halogen, —$CF_3$, —$CCl_3$, —$CBr_3$, —$CI_3$, —$CHF_2$, —$CHCl_2$, —$CHBr_2$, —$CHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 179. The method of embodiment 178, wherein the subject is suffering from obesity, non-alcoholic fatty liver disease (NAFLD), a metabolic inflammation-mediated disease or disorder, metabolic syndrome, or any combination thereof.

Embodiment 180. The method of embodiment 179, wherein the NAFLD is non-alcoholic steatohepatitis (NASH).

Embodiment 181. The method of any one of embodiments 178-180, wherein the compound of Formula (I) is:

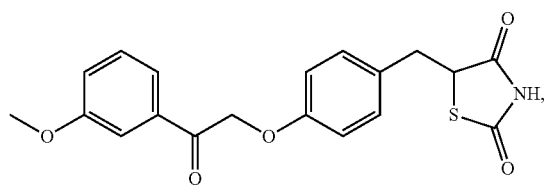 [SMILES: COc1cccc(C(=O)COc2ccc(CC3SC(=O)NC3=O)cc2)c1]

or a pharmaceutically acceptable salt thereof.

Embodiment 182. The method of any one of embodiments 178-181, wherein the pharmaceutically acceptable salt is a potassium salt.

Embodiment 183. The method of any one of embodiments 126-182, wherein further comprising an additional therapeutic agent.

Embodiment 184. The method of embodiment 183, wherein the additional therapeutic agent is a GLP1 agonist.

Embodiment 185. The method of embodiment 184, wherein the GLP1 agonist is exenatide, liraglutide, semaglutide, or dulaglutide.

Embodiment 186. The method of embodiment 185, wherein the GLP1 agonist is exenatide.

V. EXAMPLES

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

Example 1. Effects of MSDC-0602 and GLP1 on Pancreatic Islets in ZDSD/Pco Rats Challenged with a High Fat Diet A new class of insulin sensitizers has been identified, which modify a newly identified mitochondrial target thus avoiding the side effects associated with direct activation of nuclear receptors. This mechanism appears to involve alteration in nutrient sensing pathways that favor the differentiated state of the beta cells, a least in vitro. The ZDSD/Pco rat is a new rat model of type 2 diabetes that undergoes beta cell dysfunction in response to a high fat diet. As such, these rats are a model for a key feature of type 2 diabetes that involves a progressive loss of beta cell function that appears to involve both beta cell death and loss of differentiated phenotype. Clinical evidence suggests a potential powerful synergy between first generation insulin sensitizers and GLP1 in the clinic when given as an early treatment. Here, the combination of GLP1 treatment with an mTOT modulator currently in clinical trials might function for the prevention of loss of functional beta cells in the ZDSD/Pco rat was investigated.

Methods:

Male ZDSD/Pco rats were maintained on standard chow 5008 (Purina) until treatment groups were switched to the high fat diet (Purina 5SCA). Treated animals were given a single oral dose of vehicle (1% SCMC/0.1% Tween 80) or MSDC-0602 (15 mg/kg) and a 0.1 ml subcutaneous injection of vehicle or 1 μg exenatide. Control rats (given both vehicles) were maintained on the normal diet and the treatment groups were switched to the high fat diet as indicated. Glucose and insulin were measured weekly from tail vein samples. On day 36 an oral glucose tolerance test (OGTT); 2 g/kg) was conducted after a 16 hour fast. Glucose samples were taken at 0, 30, 60, 90, and 120 minutes; insulin was measured at 0 and 30 minutes and the change at 30 minutes is shown. Data are mean and SE; N=10. At sacrifice, the pancreas was fixed in formalin and shipped to MSU for histology and IHC. A range of anti-bodies were used to identify and quantify the presence of insulin, Ki67, collagen, CD3 lymphocytes, PDX-1 and Bcl2. An Image-Pro system was used with Image J to quantify the degree of positive staining.

Figure 1B:
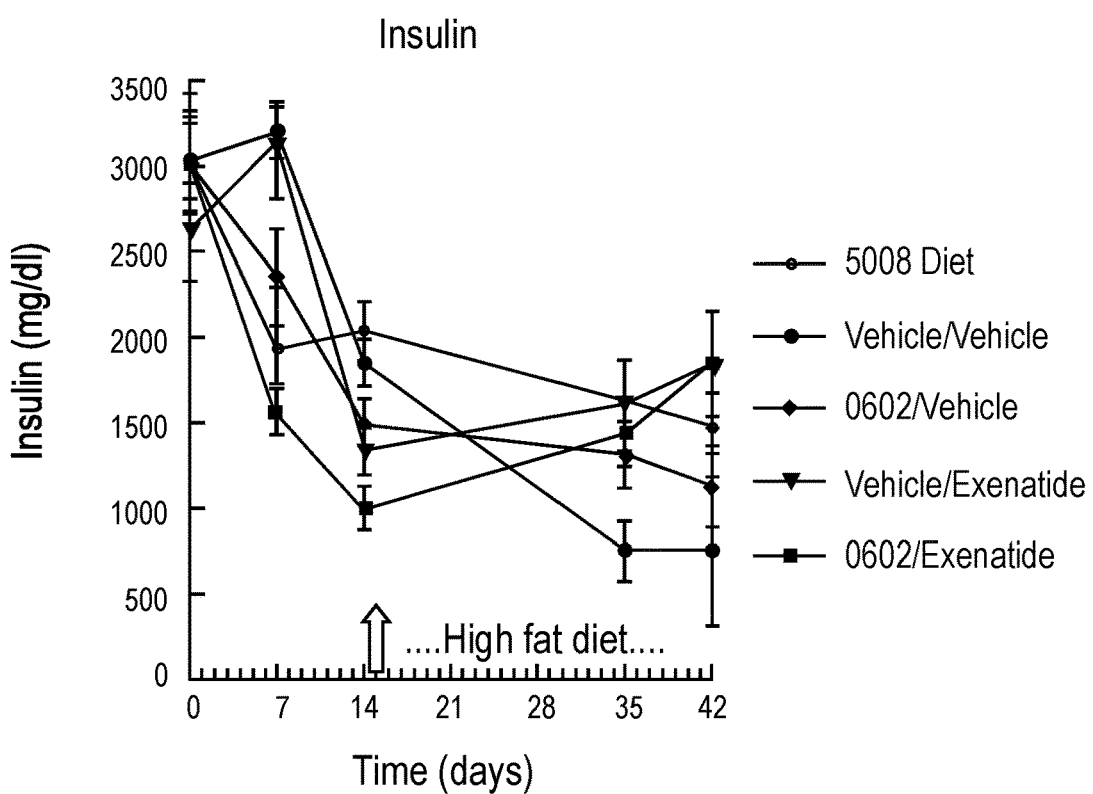
Figure 2:
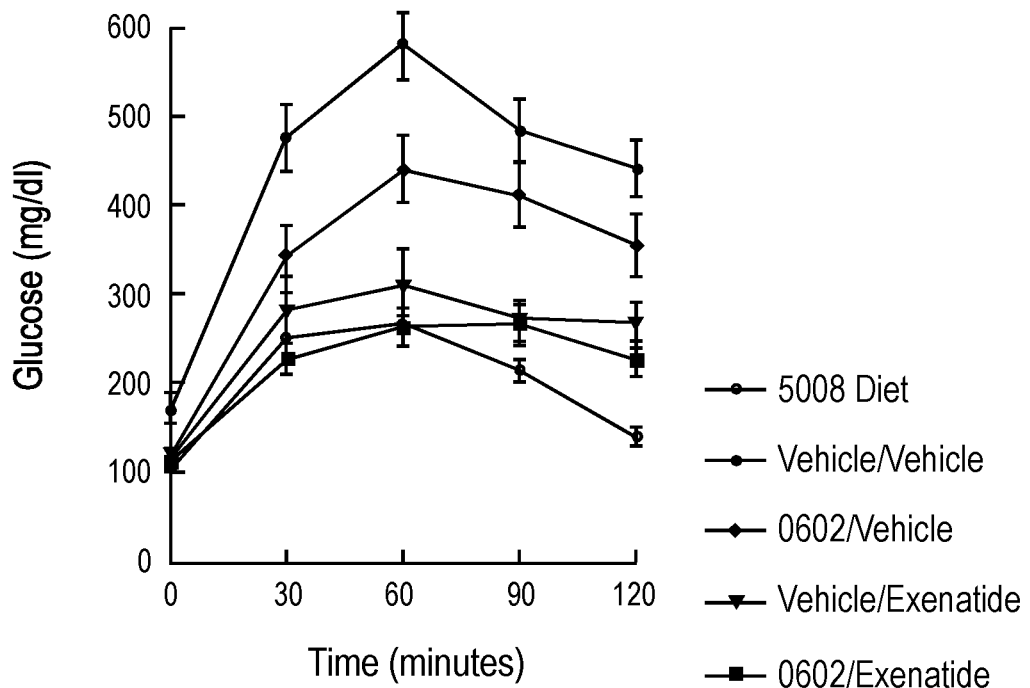
FIG. 2. Graphic representation of the effect of MSDC-0602 and GLP1 on oral glucose tolerance test (OGTT).
Figure 3:
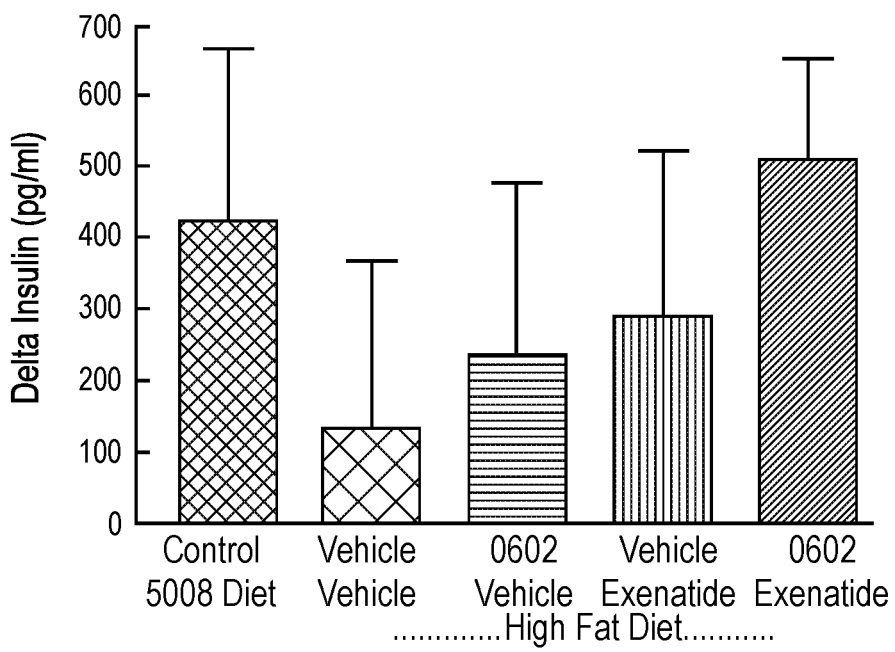
FIG. 3. Insulin levels in male ZDSD/Pco rats were measured at 0 and 30 minutes. The change in insulin at 30 minutes is shown.
Figure 4A:
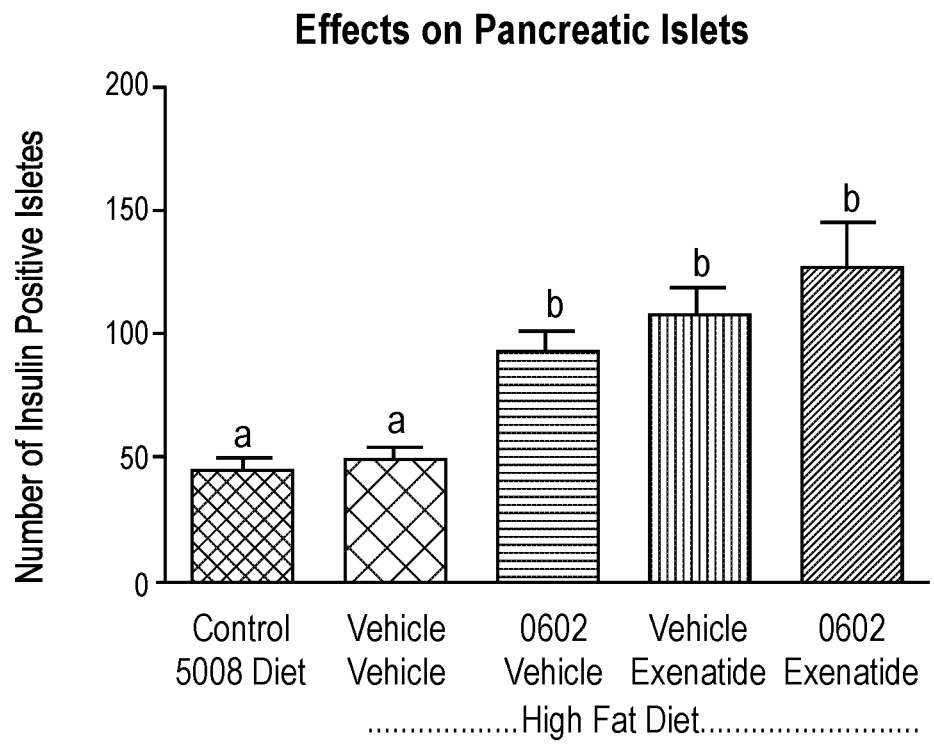
FIGS. 4A-4C. Graphic representations of the effects of MSDC-0602 and GLP1 on insulin positive islet cells (FIG. 4A) and islets positive for Ki67 by intensity (FIG. 4B) and per islet (FIG. 4C).
Figure 4B:
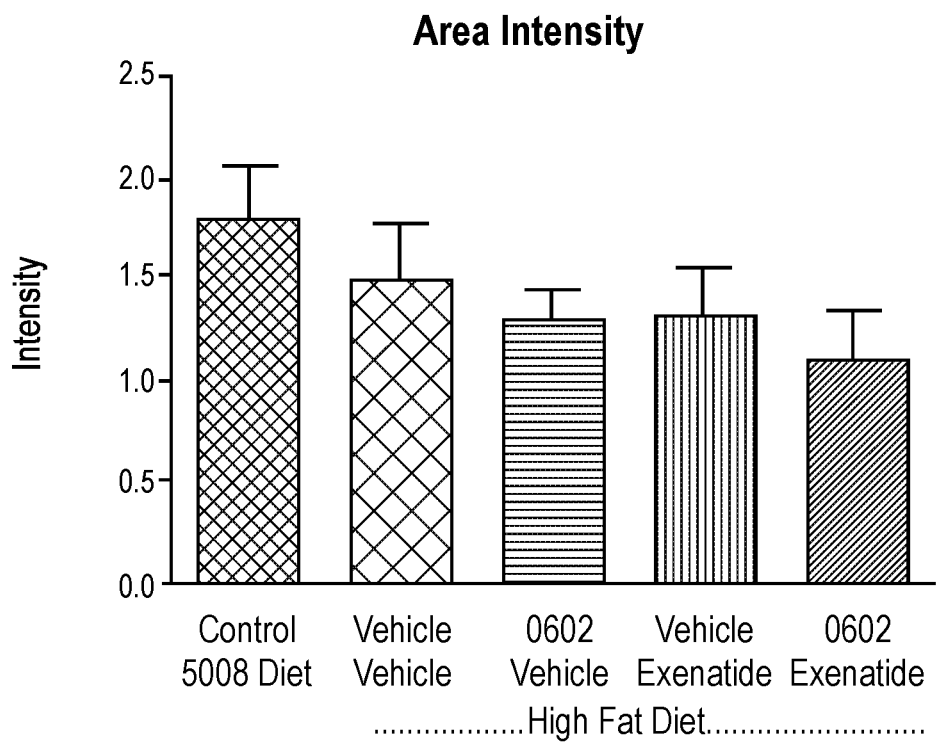
Figure 4C:
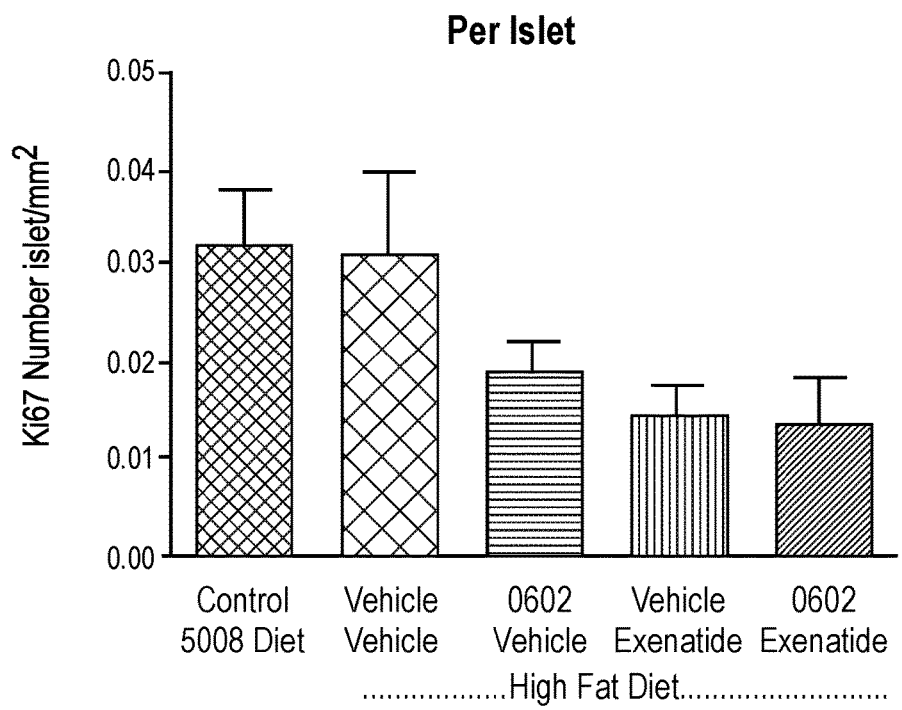

MSDC-0602 is a new insulin sensitizing agent designed to act on the mitochondrial target, mTOT. It was previously shown that MSDC-0602 lowered circulating glucose and insulin in a phase 2 clinical trial (FIGS. 1A-1B). There is an apparent synergism between GLP1 and MSDC-0602 on circulating glucose and insulin levels and in oral glucose tolerance test (OGTT) (FIG. 2).

Here, the potential MSDC-0602 beneficial effects on the pancreatic islets in the ZDSD/Pco rat, a model selected for beta cell dysfunction in response to a high fat diet, were investigated. Since this model responds to GLP1, the combination of GLP1 treatment with this mTOT modulator was also evaluated. Five matched groups of ZDSD/Pco rats were selected at 14 weeks of age and then treated for 6 weeks.

Figure 5:
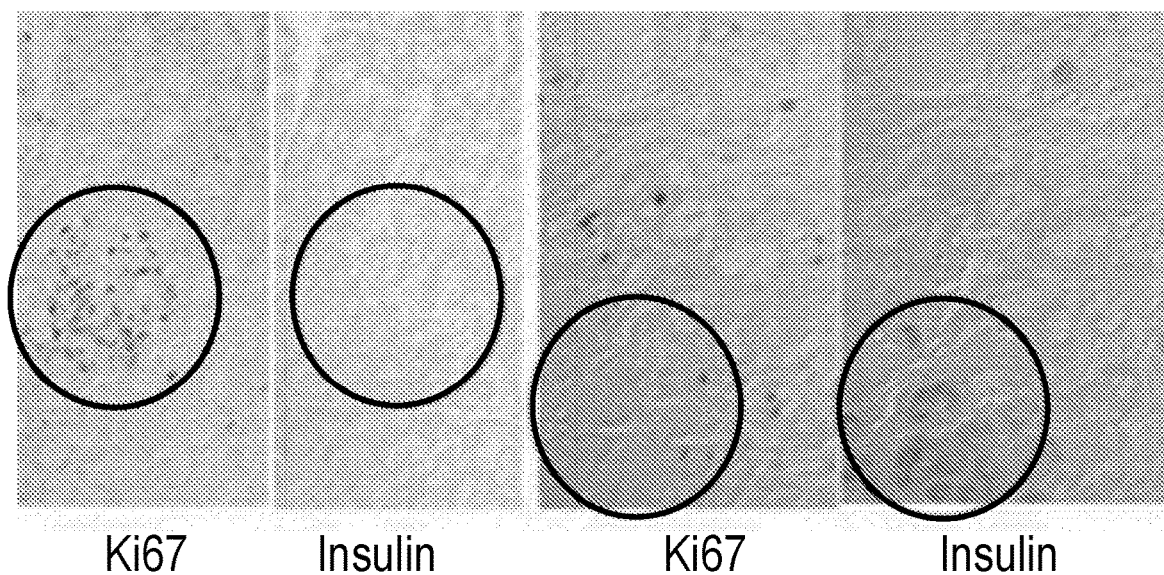
FIG. 5. Shows the results from histological studies (pancreas) of ZDSD/Pco rats.

Group 1 was maintained on the standard chow diet while the other 4 groups were switched to the 5SCA (Purina) high fat diet and then given either oral vehicle and saline injection (group 2), oral MSDC-0602 (30 mg/kg) and saline injection (group 3), oral vehicle and exenatide (s.q. 1 µg) (group 4), or oral MSDC-0602 (30 mg/kg) and exenatide (s.q. 1 µg) (group 5). The change in diet caused glucose levels to progressively rise to over 500 mg/dl in the control treated rats (group 2). Either treatment alone significantly reduced glucose levels over 4 week treatment as compared to the group 2 (control treatment on the high fat diet), but the combination of MSDC-0602 and exenatide prevented any rise in glucose. At sacrifice, the pancreas was removed, fixed, and stained for insulin, PDX1, and Ki67, as an index of proliferation. Both treatments increased the number of islet cells and insulin staining, but the largest increase was group 5 where both treatments were combined. Islets positive for Ki67 are usually negative for insulin. Exenatide increased the number of Ki67 positive cells and the combination with MSDC-0602 increased this further (i.e., synergistic increase with MSDC-0602 and GLP1). Interestingly, however, individual cells were either positive for Ki67 or insulin and/or PDX1 but not both (FIG. 5), indicating that the individual islet cells were at different stages of differentiation. These data suggest that the combination of an mTOT modulator with GLP1 therapy may be useful for the restoration of pancreatic islets in diabetes.

Figure 6A:
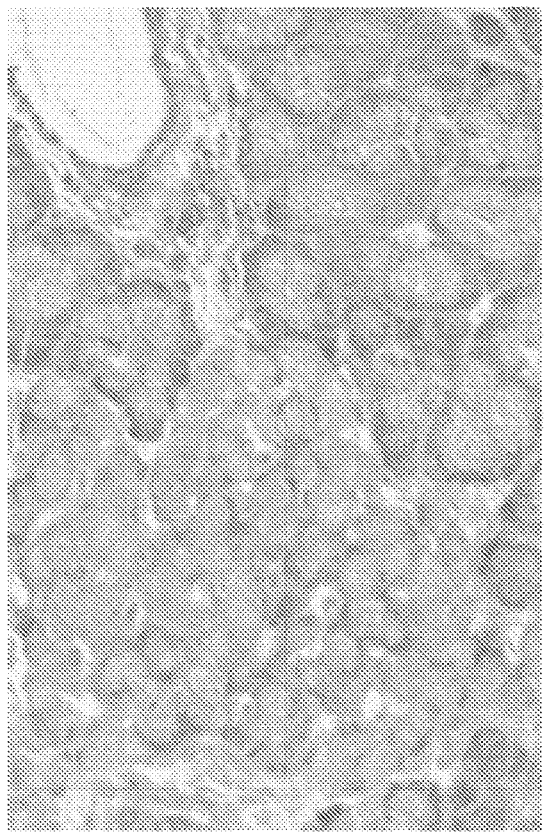
FIGS. 6A-6B. Show Bcl2 staining in an islet and ductal epithelium of MSDC-0602+exenatide group (FIG. 6A) and PDX-1 staining in an islet of MSDC-0602+exenatide group (FIG. 6B).
Figure 6B:
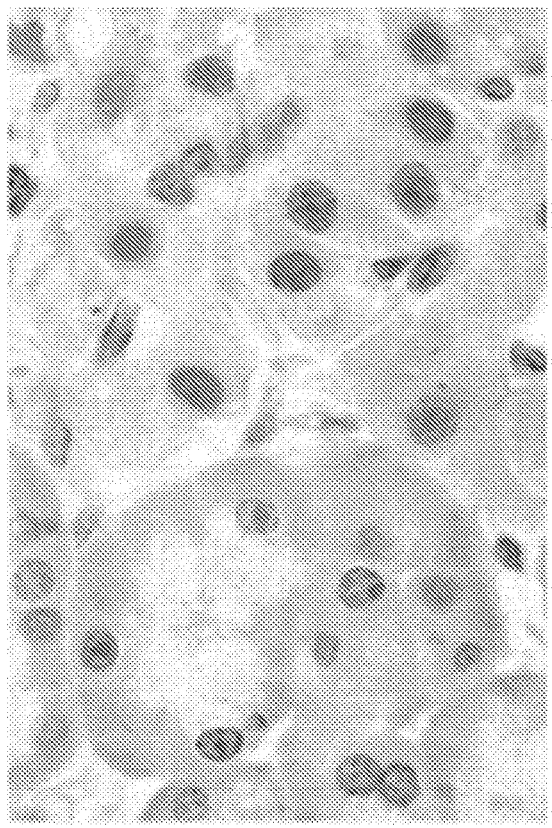

Bcl2 staining in an islet and ductal epithelium of MSDC-0602+exenatide group and PDX-1 staining in an islet of MSDC-0602+exenatide group are shown in FIGS. 6A-6B. These markers show an increase in Bcl2, which is antiapoptotic and PDX-1, which is needed as cells differentiate into insulin-producing beta cells.

These results suggest a therapeutic value to combining mTOT modulators with GLP1 agonists to preserve functional beta cells. Excess nutrients may inhibit AMPK and activate mTOR favoring loss of beta cell phenotype/functional beta-cells. Metabolic inflammatory signals may also trigger cell death pathways. mTOT modulation by MSDC-0602 together with GLP1 action elicit signals favoring maintenance of beta cell phenotype.

Example 2. Acute Mitochondrial Pyruvate Carrier-Dependent and -Independent Effects of MSDC-0602 in Hepatocytes on Insulin Sensitivity and NASH Endpoints in Mice Insulin-sensitizing thiazolidinediones (TZDs) have shown promise for the treatment of NASH, but their use is limited by side effects of PPARγ-agonism. MSDC-0602 is a "next-generation" TZD which does not bind/activate PPARγ, but binds and modulates the mitochondrial pyruvate carrier (MPC). It has been reported that treatment with MSDC-0602 prevents and reverse liver damage in a mouse model of NASH, and that these beneficial effects require MPC expression in hepatocytes. The purpose of these studies were to differentiate the acute MPC2-dependent and -independent effects of MSDC-0602 by using liver specific MPC2−/− (LS-MPC2−/−) mice. A follow-up study to investigate the circulating exosome miRNA content in a mouse model of NASH with and without MSDC-0602 treatment was then performed.

Methods:

8 week old WT and LS-MPC2−/− mice were fed a diet of 60% fat (Research Diets D12492) for 20 weeks to induce obesity and insulin resistance. Intraperitoneal glucose tolerance tests (GTT) were performed after a 4 h fast by injection of 1 g/kg D-glucose in saline i.p. to assess glucose tolerance. 3 days after the initial GTT, mice were randomized to receive a single gavage of either vehicle (1% CMC, 0.01% Tween-80) or 30 mg/kg MSDC-0602K. Plasma insulin was measured by Singulex assay and plasma ALT levels were measured by commercially-available kits (Teco Diagnostics). qPCR was performed by isolation of total RNA with RNA-Bee and reverse transcription with a high-capacity cDNA synthesis kit (Invitrogen). qPCR was performed on an Applied Biosystems real-time thermocycler.

NASH (HTF-C) Diet Plasma RNA Experiments:

It has been described that hepatocyte-specific MPC2−/− (LS-MPC2−/−) mice are also protected against NASH liver injury, and that these hepatocytes may release exosomes that alter the activation of hepatic stellate cells.

To begin evaluating the exosome cargo of MSDC-0602K-treated mice, WT mice were fed with either a low fat (LF) control diet (Research Diets D09100304) or high trans-fat, fructose, cholesterol (HTF-C) diet composed of 40% trans-fat, 20% fructose, 2% cholesterol (Research Diets D09100301). A subset of mice was fed plain HTF-C diet for 4 or 16 weeks, then switched to HTF-C diet that contained 331 ppm MSDC-0602.

Total RNA was isolated from 400 µL of serum and small RNA sequencing was performed by adapter ligation, cDNA synthesis and size selection of 145-160 base pairs. Sequencing was then performed on an Illumina HiSeq3000.

It was found that diet-induced obese LS-MPC2−/− mice display improved glucose tolerance. WT (fl/fl) and LS-MPC2−/− mice were put on 60% HF diet and became equally obese. A GTT reveals that obese LS-MPC2−/− mice are more glucose tolerant. (FIGS. 9A-9C).

Figure 10A:
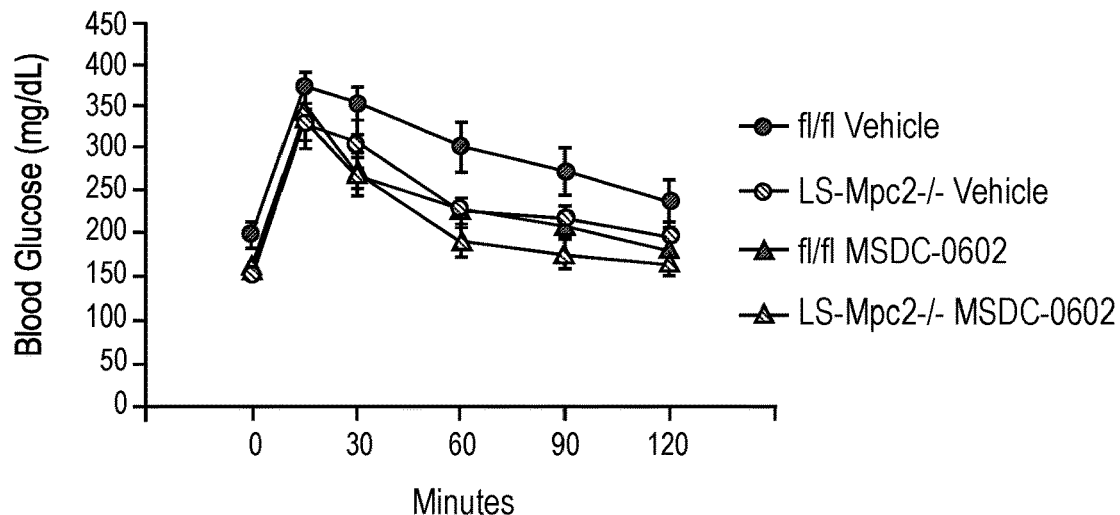
FIGS. 10A-10C. Show the results after a single dose of MSDC-0602 given to LS-MPC2−/− and WT (fl/fl) mice. Blood glucose levels (FIG. 10A); Blood glucose AUC (FIG. 10B); Plasma insulin levels (FIG. 10C).
Figure 10B:
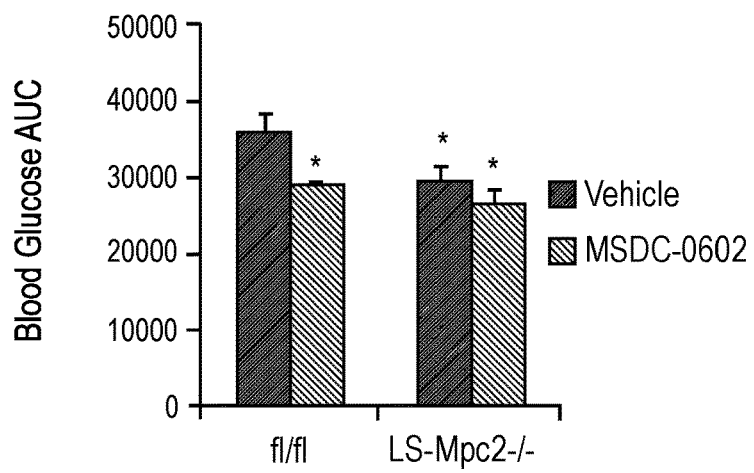
Figure 10C:
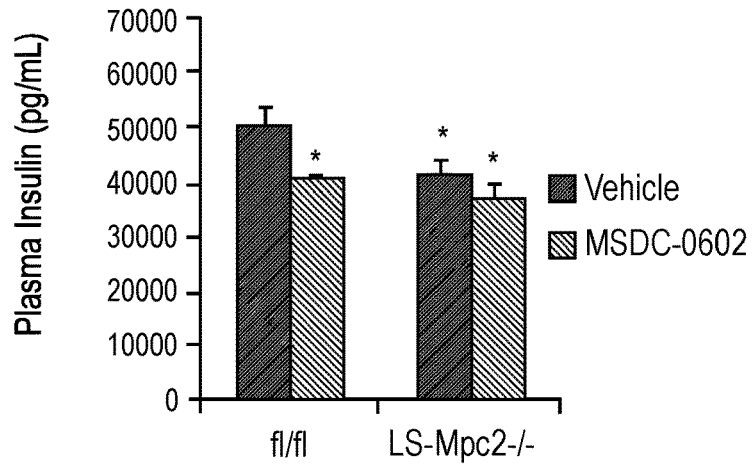

Moreover, a single dose of MSDC-0602 improves glucose tolerance. GTT 20 h after a single dose of vehicle or 30 mg/kg MSDC-0602 shows improved glucose tolerance in WT mice treated with MSDC-0602. LS-MPC2−/− again show improved glucose tolerance compared to WT mice, and appear to show no improvement in glucose tolerance. However, plasma insulin values are decreased in both WT and LS-MPC2−/− mice that were treated with MSDC-0602, indicating that both WT and LS-MPC2−/− mice have improved insulin sensitivity after MSDC-0602 treatment. (FIGS. 10A-10C).

Figure 11A:
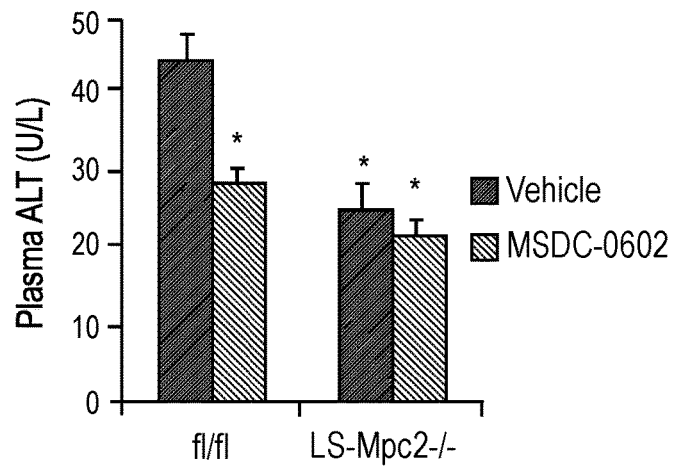
FIGS. 11A-11B. Show the results after a single dose of MSDC-0602 given to LS-MPC2−/− and WT (fl/fl) mice. Plasma ALT concentrations (FIG. 11A); Gene expression for markers of liver injury (FIG. 11B).
Figure 11B:
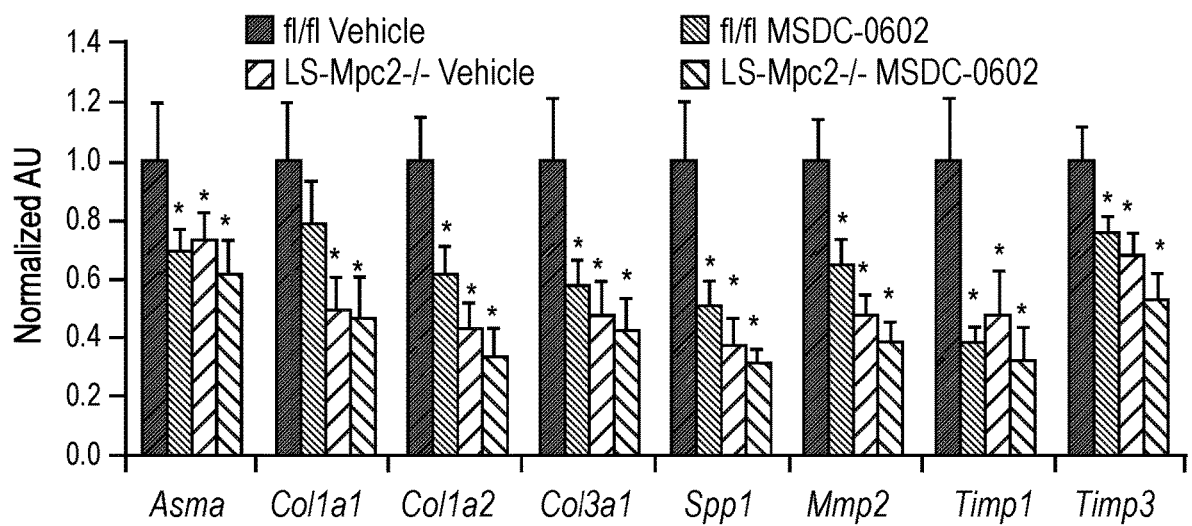

Liver-specific MPC2 deletion or acute MSDC-0602 diminish markers of liver injury in NAFLD. LS-MPC2−/− mice, or WT mice treated with a single dose of MSDC-0602 display decreased plasma ALT concentrations (FIG. 11A) and decreased gene expression for hepatic stellate cell activation and fibrotic scar formation (FIG. 11B). For these analyses, LS-MPC2−/− mice appear refractory to the beneficial effects of acute MSDC-0602 treatment.

Figure 12:
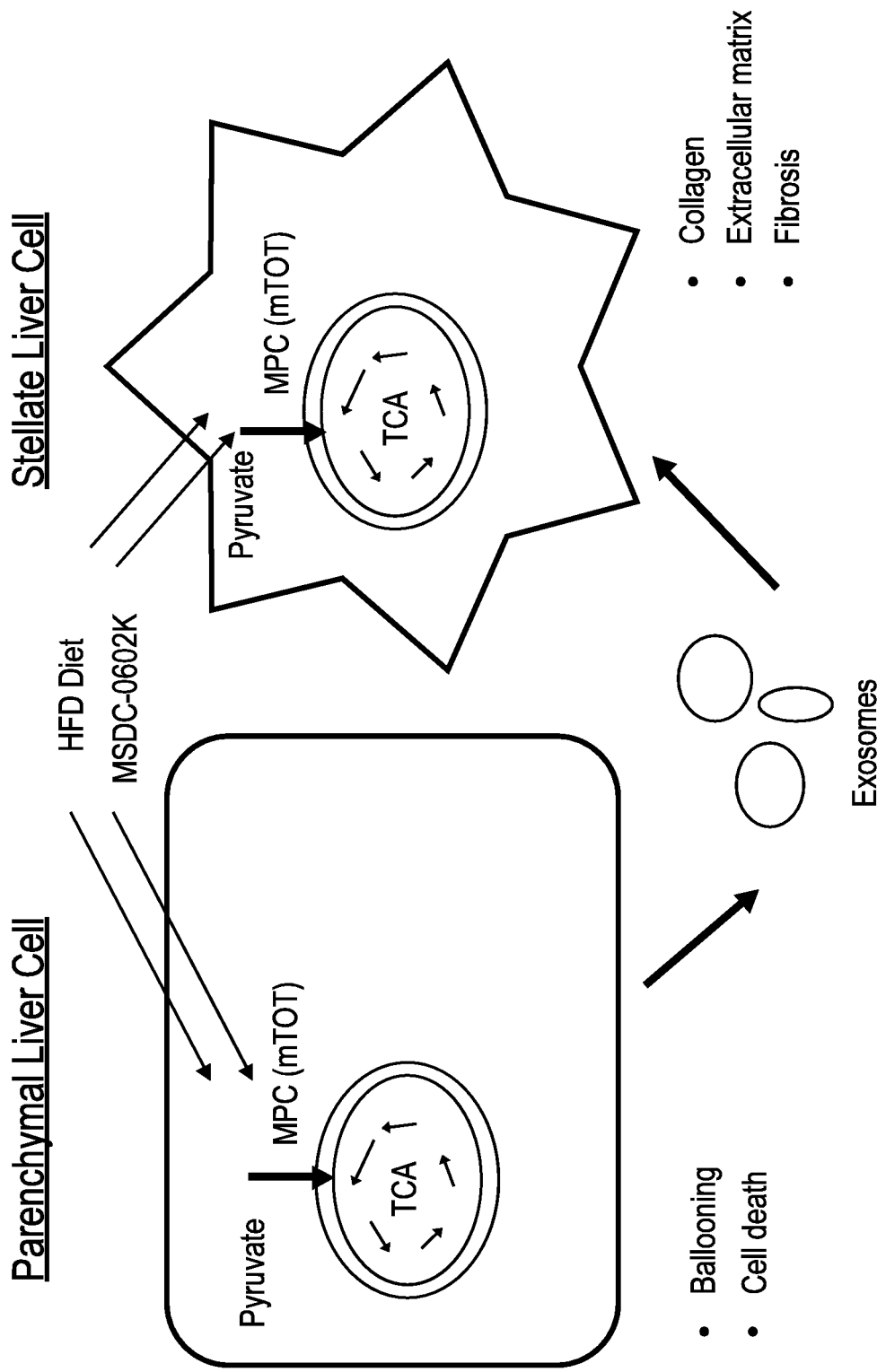
FIG. 12. A schematic representation of the effects of hepatocyte metabolism on exosome communication with stellate cells.

Altering hepatocyte metabolism by MPC2−/− or MSDC-0602 treatment regulates exosome signaling to hepatic stellate cells as shown in FIG. 12.

Figure 13A:
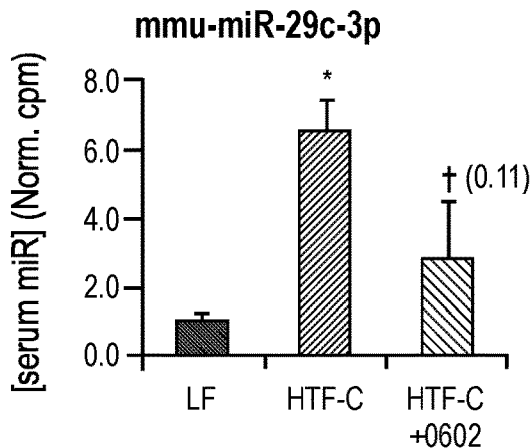
FIGS. 13A-13I. Show the levels of serum miRNAs after treatment of mice with MSDC-0602: mmu-miR-29c-3p (FIG. 13A); mmu-miR-802-3p (FIG. 13B); mmu-miR-802-5p (FIG. 13C); mmu-miR-127-3p (FIG. 13D); mmu-miR-129-2-3p (FIG. 13E); mmu-miR-615-3p (FIG. 13F); mmu-miR-129-5p (FIG. 13G); mmu-miR-205-5p (FIG. 13H); mmu-miR-341-3p (FIG. 13I). (*FDR<0.05 vs LF; † FDR<0.05 vs HTF-C.)
Figure 13B:
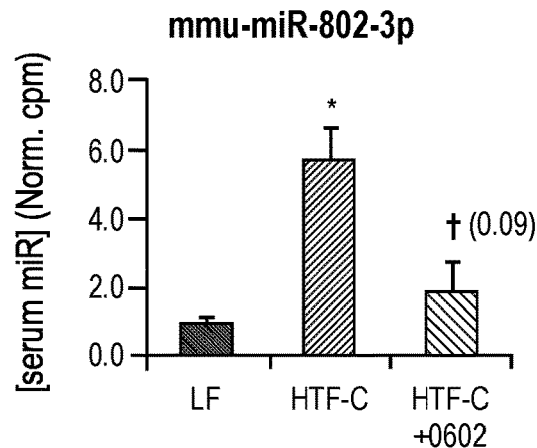
Figure 13C:
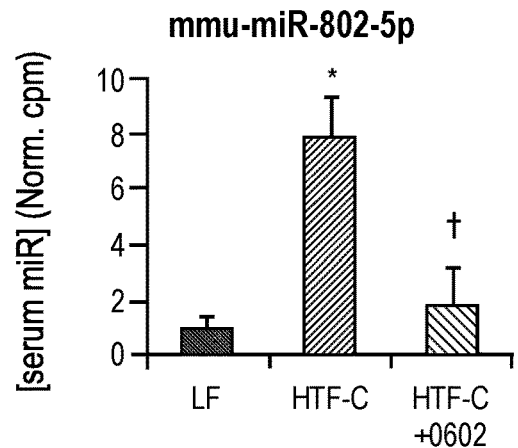
Figure 13D:
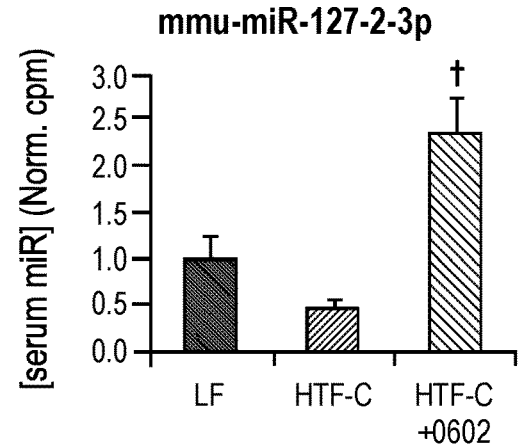
Figure 13E:
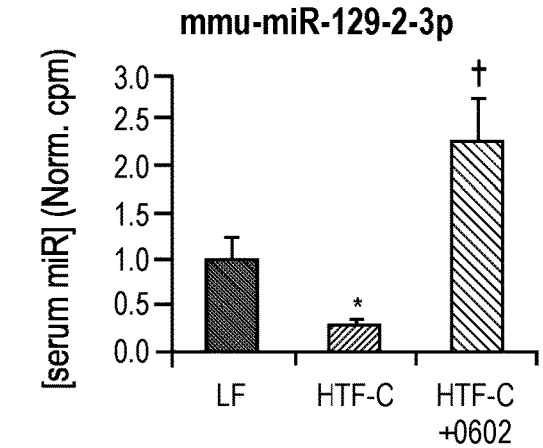
Figure 13F:
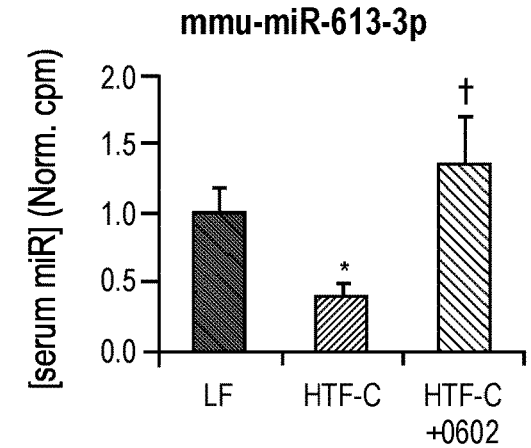
Figure 13G:
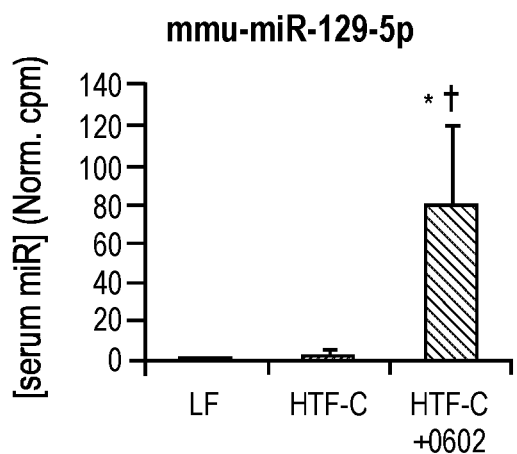
Figure 13H:
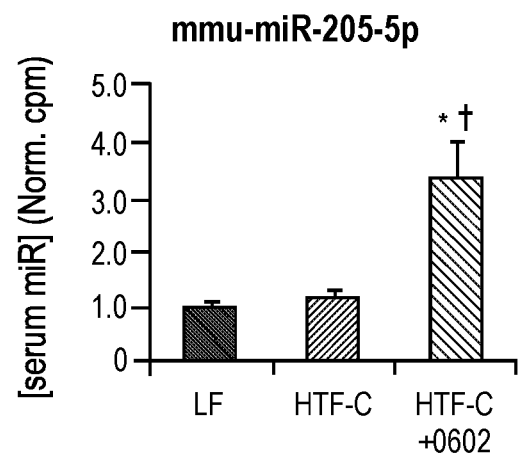
Figure 13I:
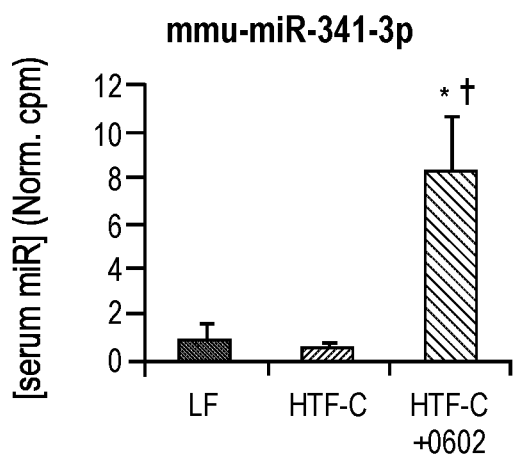

Serum miRNAs are altered in a mouse model of NASH and largely corrected by MSDC0602 treatment. Heat map of serum miRNAs depicts large number of counter-regulated miRNAs with HTF-C diet and treatment with MSDC-0602. Heat map miRNAs (~230 miRNAs) were selected by filtering data for 2-fold or greater change and FDR<0.1 comparing LF to HTF-C diet (not shown). Examples of miRNAs that are upregulated in NASH and down with MSDC-0602 (FIGS. 13A-13C), down in NASH and up with MSDC-0602 treatment (FIGS. 13D-13F), or simply show large effect of MSDC0602 treatment (FIGS. 13G-13H). Dysregulation of a number of these miRNAs has been previously identified in liver or other fibrotic diseases.

Conclusions

It was found that liver-specific KO of MPC improves insulin sensitivity in diet-induced obesity. Furthermore, acute dosing with MSDC-0602K improves glucose tolerance, but is not totally dependent on hepatocyte MPC. The major acute effects of MSDC-0602K to attenuate liver injury require hepatocyte MPC and include the release of factors from hepatocytes that affect stellate cells. Altering hepatocyte pyruvate metabolism regulates exosome cargo, which can alter the activation and fibrogenesis of hepatic stellate cells.

Example 3. Combination of MSDC-0602 with GLP1 Agonists, Phosphodiesterase Inhibitors, and Thyroid Hormone Beta Receptor Agonists MSDC-0602 treats NASH by attenuating the entry of pyruvate into the mitochondria in multiple cell types. This results in an alteration of metabolic signals that are useful in treating metabolic diseases such as NAFLD, NASH, Type 2 Diabetes, or patients with both NAFLD/NASH and Type 2 Diabetes. In the presence of a metabolic disease, this change in metabolic signals produced by the actions of MSDC-0602 result in indirect activation of PPARγ and PPARα gene networks resulting in favorable effects on lipid metabolism, which include an increase in fatty acid oxidation and a reduction in de novo lipid synthesis. These effects on metabolism also result in a decrease in inflammation and a reduction in cellular signals that otherwise result in increased fibrosis and damage to important internal organs such as the liver and kidney. While this action of MSDC-0602 is useful by its own right, there are special synergies between MSDC-0602, its potassium salt (MSDC-0602K), and other agents, which are capable of increasing the levels of cAMP within the target cells. These classes of agents that increase cellular levels of cAMP include, in particular, GLP1 agonists and phosphodiesterase inhibitors. This synergy results from both reciprocal augmentation of the pharmacological effects of MSDC-0602 through its target the pyruvate carrier and the effects of cAMP through its downstream modifications. Importantly, this allows the reduction of the length of exposure/time of treatment with the agents that modify cellular cAMP thus reducing the potential for side-effects with those agents and improved compliance to the desired clinical endpoint. The combination of these modalities will also result in improved overall therapeutic outcomes including greater reduction of the metabolic disturbance with more optimal ancillary effects including body weight.

The GLP1 agonists contemplated for use in this combination are many, but include exenatide, liraglutide, semaglutide, dulaglutide, and the like. These GLP1 agents may be administered orally, by injection, or by an implantable minipump. MSDC-0602K may be administered once daily by an oral pill at doses from about 62.5 to about 250 mg/day. Because of the synergy produce by the combination with the GLP1 agonist, treatment with the GLP1 agonist with MSDC-0602K may be limited to about 6 months. For a 6-month implantable pump, this entails one use only. For one-month injectable agents, this entails about 6 injections, and for weekly agents, this entails about 25 injections. The effect of this synergy will be to increase compliance, clinical outcomes, reduce side-effects and to reduce cost. It is also expected that this combination will, in some cases, allow higher doses of MSDC-0602K to achieve its desired therapeutic effects with reduction or stabilization of body weight.

The phosphodiesterase (PDE) inhibitors contemplated for use in combination may be pan-inhibitors or specific inhibitors, for example, of PDE4 or PDE5. Non-exhaustive examples of such agents include pentoxifylline, theophylline, ibudilast, roflumilast, sildenafil, and tadalafil. These agents will be administered orally and MSDC-0602K can be administered once daily by an oral pill at doses from about 62.5 to about 250 mg/day. The dosing of the PDE inhibitor may be for about 6 months or shorter or may be in continued combination with MSDC-0602K, depending on the individual patient. The effect of this synergy will be to increase compliance, clinical outcomes, reduce side-effects and reduce cost. It is also expected that this combination will, in some cases, allow higher doses of MSDC-0602K to achieve its desired therapeutic effects with reduction or stabilization of body weight.

MSDC-0602 may be administered in combination with a thyroid beta receptor agonist, including MGL-3196, VK2809, and VK0214.

Figure 14:
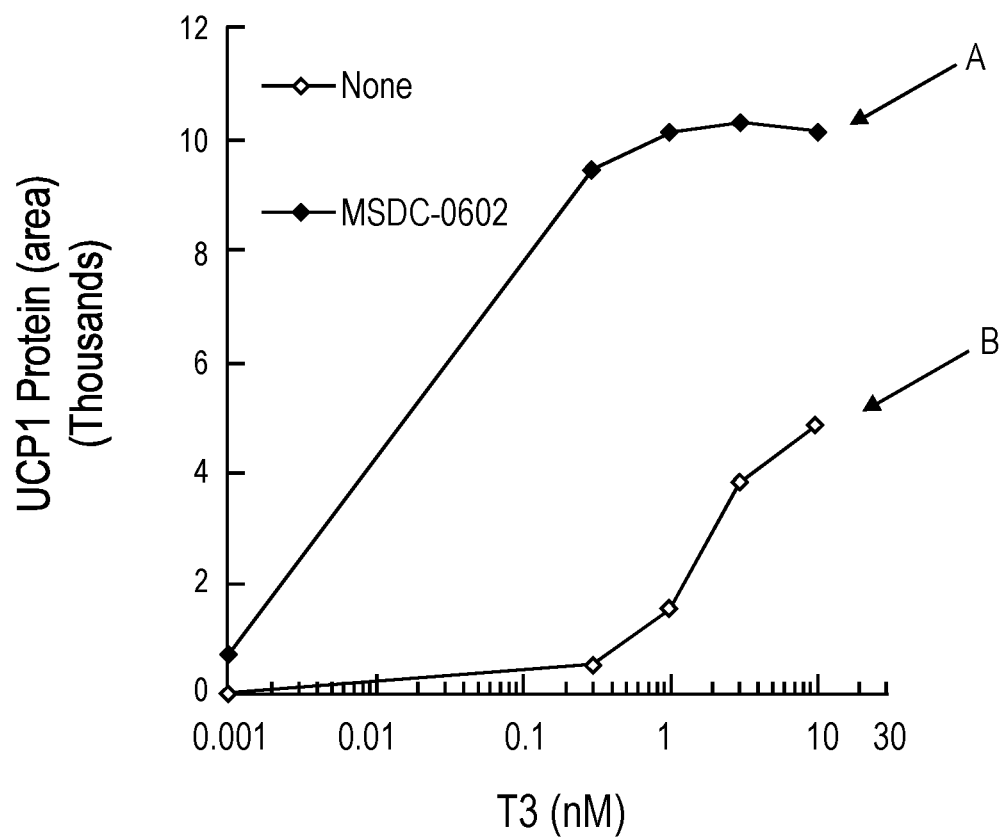
FIG. 14. Is a graphic representation of the data of thyroid hormone with MSDC-0602 in vitro. Line "A" is MSDC-0602 added to the concentrations of T3 as shown on the x-axis (from 0 to 30 nM). Line "B" is the effect of the same T3 doses without MSDC-0602. The data clearly show that MSDC-0602K is synergistic with thyroid hormone both in terms of the sensitivity and the magnitude of the response to increase the expression of UCP1 (uncoupling protein 1).

FIG. 14 provides data on the synergy of thyroid hormones with MSDC-0602 in vitro showing that the combination can lower the doses of each needed to differentiate brown adipose precursors. The addition of the thyroid agonist not only increases the maximum response. Line "A" at X=0 is MSDC-0602 itself without T3; Line "B" is T3 doses without MSDC-0602. Following the Line A extension shows both synergy (much larger response) and increased sensitivity to the thyroid hormone effect since it maxes out at a 100-fold lower dose of T3 than the response without 0602). The response measured here is increased expression of the uncoupling protein 1 (UCP1) on Western blot—a measure of differentiation of brown adipose cells. The synergy will allow greater therapeutic efficacy and also using lower doses of each drug will also reduce off-target effects for a superior therapeutic outcome.

Example 4. Randomized, Double-Blinded Study of Three Doses of MSDC-0602K or Placebo Given Orally Once Daily to Subjects with Biopsy Proven NASH with Fibrosis and No Cirrhosis Detailed Description: This is a randomized, double-blinded study of three doses of MSDC-0602K or placebo given orally once daily to subjects with biopsy proven NASH with fibrosis and no cirrhosis. Visits to the clinic will be at baseline, 1, 2, 3, 6, 9, and 12 months, with one 2-week follow-up visit. Safety will be assessed by monitoring of vital signs, 12 lead electrocardiogram (ECG), physical examinations, safety labs, and adverse events (AEs).

Descriptive Information

A study to evaluate the safety, tolerability & efficacy of MSDC 0602K in patients with NASH. A phase 2, randomized, double-blind, placebo-controlled, 12-month, multiple-dose study to evaluate the safety, tolerability and efficacy of three dose levels of MSDC 0602K in patients with NASH (EMMINENCE™).

Brief Summary This is a randomized, double-blinded study of three doses of MSDC-0602K or placebo given orally once daily to subjects with biopsy proven NASH with fibrosis and no cirrhosis.

| | |
|---|---|
| Study Type | Interventional |
| Study Phase | Phase 2 |
| Study Design | <ul><li>Allocation: Randomized</li><li>Intervention Model: Parallel Assignment</li><li>Masking: Quadruple (Participant, Care Provider, Investigator, Outcomes Assessor)</li><li>Primary Purpose: Treatment</li></ul> |
| Condition | <ul><li>Non-alcoholic Fatty Liver Disease</li><li>Non-alcoholic Steatohepatitis</li><li>NASH - Nonalcoholic Steatohepatitis</li></ul> |
| Intervention | <ul><li>Drug: MSDC-0602K</li><li>MSDC-0602K capsules</li><li>Drug: Placebo</li><li>Placebo capsules</li></ul> |
| Study Arms | <ul><li>Active Comparator: MSDC-0602K Dose 1 capsules</li><li>MSDC-0602K Dose 1 capsule taken once daily for 360 days</li><li>Intervention: Drug: MSDC-0602K</li><li>Active Comparator: MSDC-0602K Dose 2 capsules</li><li>MSDC-0602K Dose 2 capsules taken once daily for 360 days</li><li>Intervention: Drug: MSDC-0602K</li><li>Active Comparator: MSDC-0602K Dose 3 capsules</li><li>MSDC-0602K Dose 3 capsules taken once daily for 360 days</li><li>Intervention: Drug: MSDC-0602K</li><li>Placebo Comparator: Placebo capsules</li><li>Matching Placebo capsule taken once daily for 360 days</li><li>Intervention: Drug: Placebo</li></ul> |
| Eligibility Criteria | Selected Inclusion Criteria:<ul><li>Adult subjects 18 years of age or greater</li><li>Histological evidence of NASH, based on biopsy, with a NAS (NASH CRN scoring) ≥ 4 with a score of at least 1 in each component of NAS.</li><li>Histological evidence of liver fibrosis defined as NASH CRN System fibrosis score F1 to F3.</li><li>Subjects with type 2 diabetes mellitus (DM) must be under stable and reasonable control.</li><li>Male and female subjects who are taking Vitamin E should be on a stable dose of Vitamin E (if ≥ 400 IU) for a period of at least 3 months prior to randomization.</li><li>Females should be either postmenopausal (at least 12 months since last menses) or surgically sterilized (bilateral tubal ligation or hysterectomy). Males with female partners of child-bearing potential must agree to use adequate contraceptive methods (including a condom, plus one other form of contraception) if engaging in sexual intercourse.</li></ul> |

| | |
|---|---|
| | - Willing and able to sign an informed consent document indicating understanding the purpose of and procedures required for the study and willingness to participate in the study.<br>- Selected Exclusion Criteria:<br>- Known history of HIV.<br>- Prior liver transplantation.<br>- Other well-documented causes of active chronic liver disease.<br>- History of cirrhosis and/or hepatic decompensation including ascites, hepatic encephalopathy or variceal bleeding.<br>- History of alcohol abuse or drug abuse within 6 months of Screening.<br>- Type 1 diabetes mellitus.<br>- Current or history of recent ($\leq$ 6 months) use of ursodeoxycholic acid.<br>- Use of concomitant medications with a known significant metabolism by CYP2C8 or CPY2C9.<br>- History of diabetic ketoacidosis or hyperosmolar non-ketotic coma within 6 months prior to randomization.<br>- History of heart failure (including CHF) or previous cardiovascular event (myocardial infarct, by-pass surgery, or PTCA) within the past 6 months prior to randomization.<br>- Blood pressure greater than 160/100 mmHg.<br>- Participation in an investigational study or received an investigational drug within 30 days or 5 half-lives (whichever is longer) prior to study drug administration.<br>- Malignancy, including leukemia and lymphoma (excluding basal cell and squamous skin cell cancers and localized prostate cancer) treated within the last 2 years. |
| Current Primary Outcome Measures | Hepatic histological improvement in NAS defined as a decrease of at least 2 points with no worsening of fibrosis stage at 12 months. [ Time Frame: 12 months (360 days) ] |
| Original Primary Outcome Measures | Hepatic histological improvement in NASH defined as a decrease in the NAS (NASH CRN scoring) by at least 2 points with no concurrent worsening of fibrosis at 12 months [ Time Frame: 12 months (360 days) ]<br><br>The reduction in NAS must include either a 1 point reduction in ballooning or inflammation. Worsening of fibrosis is evaluated using the NASH Clinical Research Network (CRN) fibrosis staging system and defined as progression of at least one stage. |
| Current Secondary Outcome Measures | Proportion of subjects with resolution of NASH with no worsening of fibrosis at 12 months. [ Time Frame: 12 months (360 days) ]<br><br>Proportion of subjects with improvement of fibrosis (CRN staging score) by at least 1 stage with no worsening of NASH at 12 months. [ Time Frame: 12 months (360 days) ]<br><br>Mean change from baseline in NAFLD activity score (NAS) and each one of its components (steatosis, inflammation and ballooning) at 12 months.<br>[ Time Frame: 12 months (360 days) ] |

| | |
|---|---|
| Original Secondary Outcome Measures | Mean change from baseline in fibrosis score at 12 months. [ Time Frame: 12 months (360 days) ]

Number of participants with treatment-related adverse events as assessed by CTCAE v4.0 [ Time Frame: 12 months (360 days) ]

Proportion of patients that achieve resolution of NASH by hepatic histology at 12 months. [ Time Frame: 12 months (360 days) ]

Resolution of NASH is defined as a ballooning score of 0 and an inflammation score of 0-1 without worsening of fibrosis.

Proportion of patients that achieve an improvement in liver fibrosis, determined by a reduction from baseline of at least one point by NASH CRN scoring at 12 months. [ Time Frame: 12 months (360 days) ]

Mean changes in the NAFLD activity score and each one of its components (steatosis, inflammation and ballooning) at 12 months. [ Time Frame: 12 months (360 days) ]

Mean changes from baseline in fibrosis score (NASH CRN scoring) at 12 months. [ Time Frame: 12 months (360 days) ] |

Example 5. A Study to Assess Pharmacodynamics, Safety and Tolerability of MSDC 0602K and EXENATIDE Co-Administered for 6 Weeks in Adults with Non-Alcoholic Fatty Liver Disease Detailed Description: This study is to assess the effect of MSDC 0602K alone, exenatide alone, the co-administration of MSDC 0602K and exenatide, or placebo on whole liver fat in subjects with NAFLD. In addition, this study will evaluate the safety and tolerability of co administration of MSDC 0602K and exenatide along with the effects on selected pharmacodynamics (PD)/exploratory parameters, compared to administration of MSDC 0602K alone, exenatide alone, and placebo in adults with NAFLD.

| | |
|---|---|
| Primary Outcome Measures | Relative change in whole liver fat as assessed by magnetic resonance imaging proton density fat fraction (MRI-PDFF). [ Time Frame: Baseline up to Day 42 ]<br><br>Mean relative changes between placebo and each active drug arm (MSDC 0602K monotherapy, exenatide monotherapy and MSDC 0602K plus exenatide combination) will be evaluated. |
| Secondary Outcome Measures | • Percentage of Participants With Treatment-Emergent Adverse Events (AEs) or Serious Adverse Events (SAEs) [ Time Frame: Baseline up to 14 Days after last dose ]<br>• An AE was any untoward medical occurrence in a participant who received study drug without regard to possibility of causal relationship.<br>• Number of Participants With Change From Baseline in Electrocardiogram (ECG) Findings [ Time Frame: Baseline up to 14 Days after last dose ]<br>• Clinically significant ECG findings included: QT interval, heart rate, QTcF | interval, PR interval, and QRS interval.

- Percentage of Participants With Clinically Significant Change From Baseline in Vital Signs [ Time Frame: Baseline up to 14 Days after last dose ]
- Changes from baseline in systolic blood pressure, diastolic blood pressure and pulse rate.
- Number of Participants With Clinically Significant Change From Baseline in Laboratory Abnormalities [ Time Frame: Baseline up to 14 Days after last dose ]
- Laboratory parameters included: hematology, chemistry, and urinalysis Clinical significance of laboratory parameters was determined at the investigator's discretion.

Descriptive Information

| | |
|---|---|
| Brief Title | A study to assess pharmacodynamics, safety and tolerability of MSDC 0602K and exenatide co-administered for 6 weeks in adults with non-alcoholic fatty liver disease. |
| Official Title | A phase 2a, randomized, double blind (sponsor-open), placebo controlled, parallel group study to assess the pharmacodynamics, safety and tolerability of MSDC 0602K and exenatide co-administered for 6 weeks in adults with non-alcoholic fatty liver disease (NAFLD) |
| Brief Summary | This study is to assess the effect of MSDC 0602K alone, exenatide alone, the co-administration of MSDC 0602K and exenatide, or placebo on whole liver fat in subjects with NAFLD. In addition, this study will evaluate the safety and tolerability of co administration of MSDC 0602K and exenatide along with the effects on selected pharmacodynamics (PD)/exploratory parameters, compared to administration of MSDC 0602K alone, exenatide alone, and placebo in adults with NAFLD. |
| Study Type | Interventional |
| Study Phase | Phase 2 |
| Study Design | Allocation: Randomized<br>Intervention Model: Parallel Assignment<br>Masking: Triple (Participant, Care Provider, Investigator)<br>Primary Purpose: Treatment |
| Condition | Non-Alcoholic Fatty Liver Disease (NAFLD) |
| Intervention | • Drug: MSDC 0602K Monotherapy<br>• Participants enrolled in this Arm will receive 62.5 mg dose of MSDC 0602K and Placebo for exenatide, each to be taken once daily for 41 days and once on Day 42.<br>• Other Name: Arm B<br>• Drug: exenatide Monotherapy<br>• Participants enrolled in this Arm will receive 250 μg/mL dose of exenatide |

| | |
|---|---|
| Study Arms | and one tablet of Placebo for MSDC 0602K, all to be taken once daily for 41 days and once on Day 42.<br>- Other Name: Arm C<br><br>- Drug: Placebo<br>- Participants enrolled in this Arm will receive one tablet for Placebo of MSDC 0602K and Placebo of exenatide, to be taken once daily for 41 days and once on Day 42.<br>- Other Name: Arm A<br><br>- Drug: MSDC 0602K and exenatide Combination<br>- Participants enrolled in this Arm will receive 62.5 mg dose of MSDC 0602K and 250 µg/mL of exenatide, each to be taken once daily for 41 days and once on Day 42.<br>- Other Name: Arm D<br><br>- Placebo Comparator: Placebo<br>- Placebo (MSDC 0602K) QD Placebo (exenatide) QD<br>- Intervention: Drug: Placebo<br><br>- Experimental: MSDC 0602K Monotherapy<br>- 62.5 mg MSDC 0602K QD Placebo (exenatide) QD<br>- Interventions:<br>  - Drug: MSDC 0602K Monotherapy<br>  - Drug: Placebo<br><br>- Experimental: exenatide Monotherapy<br>- Placebo (MSDC 0602K) QD 250 µg/mL exenatide QD<br>- Interventions:<br>  - Drug: exenatide Monotherapy<br>  - Drug: Placebo<br><br>- Experimental: MSDC 0602K and exenatide Combination<br>- 62.5 mg MSDC 0602K QD 250 µg/mL exenatide QD<br>- Interventions:<br>  - Drug: MSDC 0602K Monotherapy<br>  - Drug: exenatide Monotherapy<br>  - Drug: MSDC 0602K and exenatide Combination<br><br>Recruitment Information |
| Eligibility Criteria | Inclusion Criteria:<br>Male subjects or female subjects of non childbearing potential<br>Total body weight of >50 kg (110 lbs) and a BMI greater than or equal to 25 kg/m2<br>Medical diagnosis of Type 2 Diabetes Mellitus (T2DM) being treated with no more than 1 acceptable oral antidiabetic drug OR Subjects without a diagnosis of T2DM that meet 2 or more of the following 5 criteria commonly associated with metabolic syndrome<br>Fasting Plasma Glucose (FPG) greater than or equal to 100 mg/dL; |

Documentation of at least stage 1 hypertension or medical history of hypertension;

Fasting serum HDL C <40 mg/dL for males and <50 mg/dL for females, or on pharmacological agents with explicit purpose to increase HDL-C;

Fasting serum triglyceride (TG) greater than or equal to 150 mg/dL or on pharmacological agents with explicit purpose to decrease TG;

Waist circumference greater than or equal to 40 inches (102 cm) for males and 35 inches (89 cm) for females.

Liver fat greater than or equal to 8% measured by MRI PDFF

Exclusion Criteria:

Subjects with acute or chronic medical or psychiatric condition.

Subjects with any of the following clinical laboratory abnormalities:

Fasting TG >400 mg/dL;

AST, ALT, or GGT >2.0x ULN;

Hemoglobin A1c (HbA1c) >7.0%;

Fasting plasma glucose >270 mg/dL;

Total bilirubin >1.5x ULN;

Albumin < lower limit of normal (LLN);

Platelet count <0.95x LLN;

International normalized ratio (INR) greater than or equal to 1.3.

A positive urine test for illicit drugs.

History of regular alcohol consumption.

Seated systolic BP>=160 mmHg and/or diastolic BP>=100 mmHg.

Supine 12 lead ECG demonstrating a corrected QT (QTcF) interval >450 msec or a QRS interval >120 msec.

Subjects with an estimated GFR <60 mL/min/1.73m2.

Evidence or diagnosis of other forms of chronic liver diseases.

Subjects with any of the following medical conditions:

Any condition possibly affecting drug absorption (eg prior bariatric surgery, gastrectomy, ileal resection);

Diagnosis of type 1 diabetes mellitus;

History of congestive heart failure, unstable angina, myocardial infarction, stroke, or transient ischemic attack;

Any malignancy not considered cured (except basal cell carcinoma and squamous cell carcinoma of the skin);

Active placement of medical devices in/on thoracic or abdominal cavities such as pacemakers, defibrillators;

Subjects with any anatomical or pathological abnormality that would either preclude or tend to confound the analysis of study data.

Blood donation of approximately 1 pint or more within 60 days prior to dosing.

Subjects taking prohibited concomitant medication(s) or those unwilling/unable to switch to permitted concomitant medication(s)

Weight loss of greater than or equal to 5% within 1 month prior to Screening.

Unwilling or unable to comply with the Lifestyle Requirements criteria of the protocol.

Pregnant female subjects; breastfeeding female subjects; female subjects of childbearing potential; fertile male subjects who are unwilling or unable to use highly effective

|  |  |
|---|---|
|  | method(s) of contraception. |
|  | Investigator site staff members or Pfizer employees, including their family members, directly involved in the conduct of the study. |
|  | Subjects with known prior treatment with or participation in a clinical trial involving any of the IPs |
| Sex/Gender | Sexes Eligible for Study: All |
| Ages | 18 Years to 70 Years (Adult, Older Adult) |
| Accepts Healthy Volunteers | No |

What is claimed is:

1. A method of treating non-alcoholic fatty liver disease (NAFLD), non-alcoholic steatohepatitis (NASH), diabetes mellitus, and/or metabolic syndrome, comprising:
   (i) administering to a subject in need thereof a daily dosage of from about 62.5 mg to about 250 mg of a compound of structural formula:

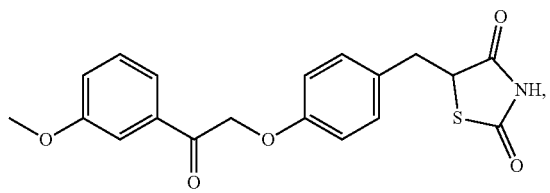 [SMILES: COc1cccc(C(=O)COc2ccc(CC3SC(=O)NC3=O)cc2)c1]

or a pharmaceutically acceptable salt thereof; and
   (ii) administering to the subject a GLP1 agonist,
wherein the daily dosage of step (i) is administered in single or multiple doses.

2. The method of claim 1, wherein the GLP1 agonist is exenatide, liraglutide, semaglutide, or dulaglutide.

3. The method of claim 1, wherein the daily dosage of the compound or pharmaceutically acceptable salt of step (i) is administered as 1 to 4 doses per day.

4. The method of claim 1, further comprising administering a potassium salt of the compound of step (i).

5. The method of claim 1, wherein the subject has type 2 diabetes mellitus.

6. The method of claim 1, wherein the compound or pharmaceutically acceptable salt of step (i) is administered orally.

7. The method of claim 1, wherein the GLP1 agonist is administered by orally, by injection, or by an implantable mini-pump.

8. The method of claim 7, wherein the GLP1 agonist is administered by injection, and wherein the GLP1 agonist is injected approximately once monthly or approximately once weekly.

9. The method of claim 1, wherein the subject has NAFLD or diabetes mellitus.

10. The method of claim 1, wherein the subject has NASH.

11. The method of claim 1, wherein the subject has NASH with fibrosis.

12. A method of treating non-alcoholic fatty liver disease (NAFLD), non-alcoholic steatohepatitis (NASH), diabetes mellitus, and/or metabolic syndrome, comprising:
   (i) administering to a subject in need thereof a daily dosage of from about 62.5 mg to about 250 mg of a potassium salt of compound of structural formula:

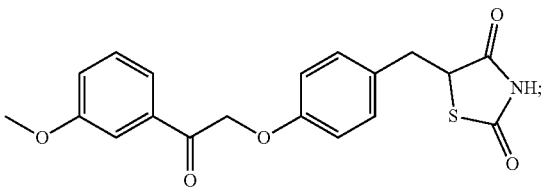 [SMILES: COc1cccc(C(=O)COc2ccc(CC3SC(=O)NC3=O)cc2)c1]

and
   (ii) administering to the subject a GLP1 agonist selected from exenatide, liraglutide, semaglutide, or dulaglutide,
wherein the potassium salt of step (i) is administered orally.

13. The method of claim 12, wherein the subject has NAFLD or diabetes mellitus.

14. The method of claim 12, wherein the subject has NASH.

15. The method of claim 12, wherein the subject has NASH with fibrosis.

16. A method of treating non-alcoholic fatty liver disease (NAFLD), non-alcoholic steatohepatitis (NASH), diabetes mellitus, and/or metabolic syndrome, comprising:
   (i) administering to a subject in need thereof a pharmaceutical composition comprising from about 62.5 mg to about 250 mg of a compound of structural formula:

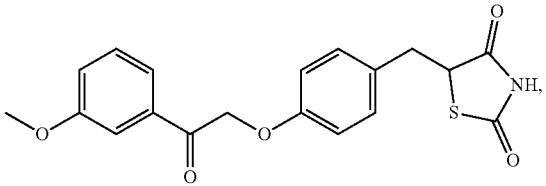 [SMILES: COc1cccc(C(=O)COc2ccc(CC3SC(=O)NC3=O)cc2)c1]

or a pharmaceutically acceptable salt thereof, and a pharmaceutically acceptable excipient; and
   (ii) administering to the subject a GLP1 agonist selected from exenatide, liraglutide, semaglutide, and dulaglutide.

17. The method of claim 16, wherein the pharmaceutical composition of step (i) is administered orally.

18. The method of claim 16, wherein the pharmaceutical composition of step (i) comprises a tablet or capsule.

19. The method of claim 18, wherein the pharmaceutical composition comprises a potassium salt of the compound of step (i).

20. The method of claim 16, wherein the pharmaceutical composition is administered once daily.

21. The method of claim 16, wherein the subject has NAFLD or diabetes mellitus.

22. The method of claim 16, wherein the subject has NASH.

23. The method of claim 22, wherein the subject has NASH with fibrosis.

24. The method of claim 21, wherein the subject has type 2 diabetes mellitus.

25. The method of claim 16, wherein the GLP1 agonist is administered by orally, by injection, or by an implantable mini-pump.

26. The method of claim 16, wherein the GLP1 agonist is administered by injection, wherein the GLP1 agonist is injected approximately once monthly or approximately once weekly.

* * * * *